United States Patent [19]

Austel et al.

[11] Patent Number: 5,434,150

[45] Date of Patent: Jul. 18, 1995

[54] CONDENSED 5-MEMBERED HETEROCYCLIC COMPOUNDS, PROCESSES FOR PREPARING THEM AND PHARMACEUTICAL PREPARATIONS CONTAINING THESE COMPOUNDS

[75] Inventors: Volhard Austel; Helmut Pieper, both of Biberach; Frank Himmelsbach; Guenter Linz, both of Mittelbiberach; Thomas Mueller, Biberach; Johannes Weisenberger, Biberach; Elke Seewaldt-Becker, Biberach, all of Germany

[73] Assignee: Dr. Karl Thomae GmbH, Biberach an der Riss, Germany

[21] Appl. No.: 937,914

[22] Filed: Aug. 28, 1992

[30] Foreign Application Priority Data

Sep. 6, 1991 [DE] Germany .................. 41 29 603.6

[51] Int. Cl.$^6$ ................. A61K 31/505; A61K 31/415; C07D 413/14; C07D 403/14
[52] U.S. Cl. ..................... 514/228.5; 514/253; 514/322; 514/318; 514/233.2; 514/233.5; 514/233.8; 514/234.2; 514/234.5; 514/234.8; 514/300; 514/394; 514/303; 514/248; 514/249; 514/263; 514/262; 514/266; 548/306.1; 548/309.7; 548/310.1; 548/310.7; 546/121; 546/118; 544/244; 544/337; 544/350; 544/277; 544/232; 544/236; 544/267; 544/268; 544/269; 544/270; 544/271; 544/276
[58] Field of Search ............ 544/271, 244, 337, 350, 544/277, 232, 236, 267, 268, 269, 270, 271, 276; 546/118, 121; 548/310.7, 306.1, 309.7, 310.1, 310.7; 514/263, 303, 394, 228.5, 253, 322, 318, 233.2, 233.5, 233.8, 234.2, 234.5, 234.8, 300, 394, 303, 248, 249, 263, 262, 266

[56] References Cited

U.S. PATENT DOCUMENTS 3,516,999 6/1970 Kano et al. .................. 260/247.5
4,563,526 1/1986 Dewhirst ..................... 546/152
4,581,457 4/1986 Musser et al. ................ 548/179

FOREIGN PATENT DOCUMENTS 0010063 4/1980 European Pat. Off. .
0151824 8/1985 European Pat. Off. .
0172631 2/1986 European Pat. Off. .
0184738 6/1986 European Pat. Off. .
0203721 12/1986 European Pat. Off. .
0215736 3/1987 European Pat. Off. .
0258191 3/1988 European Pat. Off. .
0267607 5/1988 European Pat. Off. .
0287971 10/1988 European Pat. Off. .
0412898 2/1991 European Pat. Off. .
0470543 2/1992 European Pat. Off. .

*Primary Examiner*—Mukund J. Shah
*Assistant Examiner*—Matthew V. Grumbling
*Attorney, Agent, or Firm*—Robert P. Raymond; Alan R. Stempel; Mary-Ellen M. Devlin

[57] ABSTRACT

The invention relates to cyclic imino derivatives of general formula

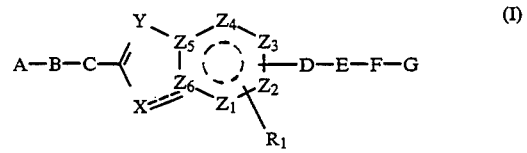

(I)

wherein

A to G, $R_1$, $Z_1$ to $Z_6$, X and Y are defined as in claim 1, the tautomers, stereoisomers and mixtures thereof and the salts thereof, particularly the physiologically acceptable salts thereof with inorganic or organic acids or bases, which have valuable pharmacological properties, preferably aggregation-inhibiting properties, pharmaceutical compositions which contain these compounds and processes for preparing them.

8 Claims, No Drawings

CONDENSED 5-MEMBERED HETEROCYCLIC COMPOUNDS, PROCESSES FOR PREPARING THEM AND PHARMACEUTICAL PREPARATIONS CONTAINING THESE COMPOUNDS

The invention relates to condensed 5-membered heterocyclic groups of the general formula

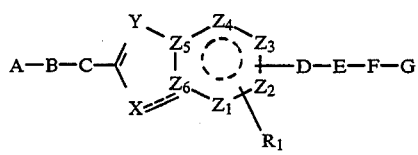

the tautomers, the stereoisomers including the mixtures thereof, and the salts thereof, especially the physiologically acceptable salts thereof with inorganic or organic acids or bases which have, inter alia, valuable pharmacological properties, preferably aggregation-inhibiting effects, pharmaceutical compositions which contain these compounds and processes for preparing them.

In general formula I above $R_1$ represents a hydrogen, fluorine, chlorine or bromine atom, an alkyl, aralkyl, aryl, heteroaryl, $R_3O$—, $(R_3)_2N$—, $R_4CO$—$NR_3$—, alkylsulphonyl-$NR_3$—, arylsulphonyl-$NR_3$—, $R_3S$—, $R_3SO$—, $R_3SO_2$— or $R_5$ group, wherein $R_3$ represents a hydrogen atom, a $C_{1-6}$-alkyl group, an aryl, heteroaryl, aralkyl, carboxyalkyl or alkoxycarbonylalkyl group, $R_4$ represents a hydrogen atom, an alkyl or alkoxy group each having 1 to 6 carbon atoms, an aryl, heteroaryl or aralkyl group having 1 to 6 carbon atoms in the alkyl moiety and $R_5$ represents an azetidino, pyrrolidino, hexamethyleneimino or heptamethyleneimino group or a piperidino group in which the methylene group in the 4-position may be replaced by an oxygen atom, a sulphenyl, sulphinyl or sulphonyl group or by an imino group substituted by an $R_3$, $R_4CO$—, alkylsulphonyl or arylsulphonyl group, wherein $R_3$ and $R_4$ are as hereinbefore defined, X represents an oxygen, sulphur or nitrogen atom or an —$NR_2$ group, wherein $R_2$ represents a hydrogen atom, a straight-chained or branched $C_{1-15}$-alkyl group, a straight-chained or branched $C_{3-10}$-alkenyl or alkynyl group in which the double or triple bond cannot be directly joined to the nitrogen atom, a cycloalkyl or cycloalkylalkyl group each having 3 to 7 carbon atoms in the cycloalkyl moiety, an aryl or heteroaryl group, a $C_{2-6}$-alkyl group which is substituted from the β-position to the nitrogen atom of the —$NR_2$ group by an $R_3O$—, $(R_3)_2N$—, $R_4CO$—$NR_3$—, alkylsulphonyl-$NR_3$—, arylsulphonyl-$NR_3$—, alkylsulphenyl, alkylsulphinyl, alkylsulphonyl or $R_5$ group, or a $C_{1-6}$-alkyl group which is substituted by one or two aryl groups, by a heteroaryl, $R_6OCO$—, $(R_3)_2NCO$—, $R_5CO$—, $R_3O$—CO-alkylene-$NR_3$—CO—, $(R_3)_2N$—CO-alkylene-$NR_3$—CO— or $R_5CO$-alkylene-$NR_3$—CO— group wherein $R_3$ and $R_5$ are as hereinbefore defined and $R_6$ represents a hydrogen atom, a $C_{1-6}$-alkyl group, a $C_{5-7}$-cycloalkyl group or an aralkyl group, Y represents an NO group, a nitrogen atom or an optionally alkyl-substituted methine group, $Z_1$, $Z_2$, $Z_3$ and $Z_4$, which may be identical or different, represent methine groups, carbon atoms, imino groups or nitrogen atoms, whilst at least one of the groups $Z_1$ to $Z_4$ must contain a carbon atom and one or two methine groups adjacent to a nitrogen atom may be replaced by carbonyl groups, $Z_5$ and $Z_6$ each represent a carbon atom or one of the groups $Z_5$ or $Z_6$ represents a nitrogen atom and the other of the groups $Z_5$ or $Z_6$ represents a carbon atom, A represents a cyano group, an amino group, a straight-chained or branched $C_{1-4}$-aminoalkyl group, an amidino, guanidino or guanidinoalkyl group, whilst in the above-mentioned amino, aminoalkyl, amidino, guanidino or guanidinoalkyl groups, at one of the nitrogen atoms one or two hydrogen atoms may be replaced by one or two $C_{1-4}$-alkyl groups or a hydrogen atom may be replaced by a $C_{2-5}$-(alkoxycarbonyl) group, by a $C_{4-6}$-(alkenyloxycarbonyl) group, by a $C_{2-5}$-(alkylcarbonyl) group, by an arylcarbonyl, aryloxycarbonyl, aralkoxycarbonyl, alkanoyloxymethoxy-carbonyl, cycloalkanoyloxymethoxycarbonyl, aralkanoyloxymethoxycarbonyl, aroyloxymethoxycarbonyl, phosphono, dialkylphosphoryl or O-alkyl-phosphono group in which each alkanoyl moiety contains 2 to 7 carbon atoms and each cycloalkanoyl moiety contains a total of 4 to 8 carbon atoms and each methoxy moiety may be substituted by a $C_{3-6}$-cycloalkyl group, by an aralkyl, aryl or alkyl group or by two alkyl groups, which may also form a 5- or 6-membered ring together with the methylene carbon atom, or, if B denotes a cyclic imine having 4 to 7 ring members, A may also denote a hydrogen atom or an alkyl group, each of which is bound to the imino nitrogen, B represents a phenylene group which may be mono- or disubstituted by fluorine, chlorine or bromine atoms, by alkyl, hydroxy, alkoxy, alkylsulphenyl, alkylsulphinyl, alkylsulphonyl, nitro, amino, alkylamino, dialkylamino, alkylcarbonylamino, alkylsulphonylamino or trifluoromethyl groups, wherein the substituents may be identical or different and at the same time one or two methine groups in the abovementioned phenylene groups may be replaced by one or two nitrogen atoms, or B represents a $C_{3-7}$-cycloalkylene group, whilst in a 4- or 5-membered cycloalkylene ring one ring member may denote a nitrogen atom and in a 6- or 7-membered cycloalkylene ring one or two ring members may each denote a nitrogen atom and at the same time linkage to carbon atoms of adjacent groups may be effected by means of such optionally present nitrogen atoms, an indanylene or 1,2,3,4-tetrahydronaphthylene group wherein the saturated ring is bound to the group A and the aromatic ring is bound to the group C or to the condensed 5-membered heterocyclic group, C denotes a bond, an alkylene, arylene, —O-alkylene, —S-alkylene, —NH-alkylene, —N(alkyl)-alkylene, —alkylene-NH—, -alkylene-N(alkyl)-, —SO-alkylene or —$SO_2$-alkylene group, D denotes a bond or an alkylene group, E denotes a $C_{1-7}$-alkylene group, an alkenylene or alkynylene group each having 2 to 7 carbon atoms, whilst the double or triple bond may not be bound directly to a nitrogen atom of the -$Z_1$-$Z_2$-$Z_3$-$Z_4$- group, or, if E is not directly bound to a nitrogen atom of the -$Z_1$-$Z_2$-$Z_3$-$Z_4$- group, E may represent an —O—, —S—, —SO—, —SO$_2$—, —NR$_3$—, —N(-COR$_4$)—, —CO—, —NR$_3$—CO—, —CO—NR$_3$—, —SO$_2$—NR$_3$13, alkylsulphonylimino or arylsulphonylimino group, wherein $R_3$ and $R_4$ are defined as hereinbefore, or a $C_{4-7}$-cycloalkylene group, whilst in a 4- or 5-membered cycloalkylene ring one ring member may denote a nitrogen atom and in a 6- or 7-membered cycloalkylene ring one or two ring members may each denote a nitrogen atom and additionally a methylene group adjacent to a nitrogen atom may be replaced by a carbonyl group, whilst at the same time linkage to carbon atoms of adjacent groups may be effected via any nitrogen atoms present, F denotes a bond, a straight-chained or branched $C_{1-6}$-alkylene group, a straight-chained or branched alkenylene or alkynylene group each having 2 to 6 carbon atoms, wherein the double or triple bond may not directly adjoin a heteroatom or a triple bond of group E, and the above-mentioned alkylene, alkenylene and alkynylene groups may each be substituted by an aryl, —COOR$_6$, —CON(R$_3$)$_2$ or —CO—N(R$_3$)— alkyl group, whilst the groups $R_3$ and $R_6$ are defined as hereinbefore and the alkyl moiety of the —CO—N(R$_3$)— alkyl group, which may contain 1 to 6 carbon atoms, may additionally be substituted by the groups $R_7$ and $R_8$, whilst $R_7$ and $R_8$, which may be identical or different, each represent a hydrogen atom, an aryl or a —COOR$_6$ group, wherein $R_6$ is defined as hereinbefore, a cycloalkylene, alkylene-cycloalkylene or cycloalkylene-alkylene group each having 4 to 6 carbon atoms in the cycloalkylene moiety, wherein a CH group located in the ring is replaced by a nitrogen atom and the linking to the adjacent group E may be effected via the nitrogen atom, if the bond is effected via a carbon atom of group E, whilst if D denotes a bond, E denotes an oxygen atom and F is an alkyl group, A cannot be an amino or acylamino group directly bound to a phenyl ring, and if at the same time X is a sulphur atom and Y is a nitrogen atom, the group A-B-C cannot be a 4-acetamino-piperazino group, and G denotes a carbonyl group not bound to a heteroatom of group E, which may be substituted by a hydroxy group, by an arylalkenyloxy group having 3 to 4 carbon atoms in the alkenyl moiety, by a $C_{1-8}$-alkoxy group (wherein a $C_{1-5}$-alkoxy group may be substituted by an aryl group or an alkoxy group having 1 to 3 carbon atoms may be substituted in the 1-, 2- or 3-position by a heteroaryl or cycloalkyl group having 4 to 8 carbon atoms or, in the 2- or 3-position, by a pyrrolidin-2-on-1-yl, morpholino, thiomorpholino or 1-oxido-thiomorpholino group), by a $C_{4-8}$-cycloalkoxy group optionally substituted by 1 to 3 alkyl groups, by a benzocycloalkoxy, benzocycloalkyl-alkoxy, bicycloalkoxy or bicycloalkylalkoxy group, (having 4 to 8 carbon atoms in the cycloalkyl moiety and 6 to 8 carbon atoms in the bicycloalkyl moiety and optionally substituted by 1 to 3 methyl groups), by an alkanoyloxymethoxy group having a total of 2 to 7 carbon atoms in the alkanoyl moiety, by a cycloalkanoyloxy-methoxy group having a total of 4 to 8 carbon atoms in the cycloalkanoyl moiety, by an alkoxycarbonyloxymethoxy group having 1 to 6 carbon atoms in the alkyl moiety, or by a cycloalkoxycarbonyloxymethoxy group having 3 to 7 carbon atoms in the cycloalkyl moiety, or by an aroyloxymethoxy, aralkanoyloxymethoxy, aryloxycarbonyloxymethoxy or aralkoxycarbonyloxymethoxy group (wherein the methoxy moiety in each case may be substituted by a $C_{1-6}$-alkyl group, by a $C_{3-7}$-cycloalkyl group or by an aralkyl or aryl group), or G represents a sulpho-, phosphono-, O-alkylphosphono- or tetrazol-5-yl group, whilst unless otherwise specified, the above-mentioned alkyl, alkylene or alkoxy moieties may each contain 1 to 3 carbon atoms, and the term "aryl group" denotes a phenyl group optionally mono-, di- or trisubstituted by fluorine, chlorine, bromine or iodine atoms, by alkyl, trifluoromethyl, nitro, amino, alkylamino, dialkylamino, alkanoylamino, alkylsulphonylamino, aminosulphonyl, alkylaminosulphonyl, dialkylaminosulphonyl, hydroxy, alkoxy, aralkoxy, carboxy, alkoxycarbonyl, aminocarbonyl, alkylaminocarbonyl, dialkylaminocarbonyl, alkylsulphenyl, alkylsulphinyl or alkylsulphonyl groups, wherein the substituents may be identical or different, or a naphthyl group, and the term "heteroaryl group" denotes a 5-membered heteroaromatic ring which contains an imino group, an oxygen or sulphur atom, one to two nitrogen atoms and an oxygen or sulphur atom or an imino group and one to three nitrogen atoms, or a 6-membered heteroaromatic ring which contains 1, 2 or 3 nitrogen atoms, whilst fused on to the above-mentioned rings may be a phenyl ring and additionally the above-mentioned rings may be mono- or disubstituted by a fluorine, chlorine or bromine atom, by an alkyl, alkoxy, hydroxy, amino, dialkylamino, alkylcarbonylamino, alkylsulphonylamino or trifluoromethyl group or by a $C_{1-4}$-alkylamino group.

Preferred compounds of general formula I above are those wherein $R_1$ denotes a hydrogen, fluorine, chlorine or bromine atom, an alkoxycarbonylamino or N-alkoxycarbonyl-alkylamino group having 1 to 4 carbon atoms in the alkoxy moiety, an alkyl, hydroxy, alkoxy, phenylalkoxy, amino, alkylamino, dialkylamino, pyrrolidino, piperidino, alkylcarbonylamino or alkylsulphonylamino group, whilst unless otherwise specified the alkyl and alkoxy moiety may each contain 1 to 3 carbon atoms, and additionally the alkyl moieties of the alkylamino and dialkylamino groups may be substituted by a carboxy or alkoxycarbonyl group having 1 to 3 carbon atoms in the alkyl moiety, X denotes an oxygen, sulphur or nitrogen atom or an —NR$_2$ group, whilst $R_2$ denotes a hydrogen atom, a straight-chained or branched $C_{1-14}$-alkyl, an alkenyl or alkynyl group each having 3 or 4 carbon atoms, wherein the double or triple bond may not directly adjoin the nitrogen atom, a $C_{1-5}$-alkyl group which may be substituted by a carboxy, alkoxycarbonyl, aminocarbonyl, alkylaminocarbonyl, dialkylaminocarbonyl, phenylalkylaminocarbonyl, pyrrolidinocarbonyl, carboxyalkylaminocarbonyl, alkoxycarbonylalkylaminocarbonyl, 2- or 4-imidazolyl or pyridyl group, by a piperidinocarbonyl group (in which the methylene group in the 4-position may be replaced by an oxygen atom or by a sulphenyl, sulphinyl, sulphonyl, imino, alkylimino or phenylalkylimino group), by a phenyl group optionally mono- or disubstituted by chlorine or bromine atoms or by amino, hydroxy, alkoxy or alkyl groups, or by two phenyl groups, a $C_{3-7}$-cycloalkyl group, a pyridyl group, a phenyl group optionally mono- or disubstituted by fluorine, chlorine or bromine atoms or by alkyl, alkoxy, alkylsulphenyl, alkylsulphinyl or alkylsulphonyl groups, wherein the substituents may be identical or different, or $R_2$ represents a $C_{2-4}$-alkyl group which is substituted in the 2-, 3- or 4-position by a hydroxy, alkoxy, alkylsulphenyl, alkylsulphinyl, alkylsulphonyl, 1-imidazolyl or pyrrolidino group or by a piperidino group, wherein the methylene group in the 4-position may be replaced by an oxygen atom, or by a sulphenyl, sulphinyl, sulphonyl, imino, alkylimino or phenylalkylimino group, or $R_2$ represents a $C_{2-6}$-alkyl group substituted in the 2-, 3-, 4-, 5- or 6-position by an amino, alkylamino or dialkylamino group, whilst unless otherwise specified the above-mentioned alkyl and alkoxy moieties may each contain 1 to 3 carbon atoms, Y represents an NO group, a nitrogen atom or a methine group optionally substituted by a $C_{1-3}$-alkyl group, $Z_1$, $Z_2$, $Z_3$ and $Z_4$, which may be identical or different, represent methine groups, carbon atoms, imino groups or nitrogen atoms, whilst at least one of the groups $Z_1$ to $Z_4$ must comprise a carbon atom and one or two methine groups adjacent to a nitrogen atom may be replaced by carbonyl groups, $Z_5$ and $Z_6$ each represent a carbon atom or one of the groups $Z_5$ or $Z_6$ represents a nitrogen atom and the other group $Z_5$ or $Z_6$ represents a carbon atom, A represents a cyano group, an amino group, a straight-chained or branched $C_{1-4}$-aminoalkyl group, an amidino, guanidino or guanidinoalkyl group, whilst in the above-mentioned amino, aminoalkyl, amidino, guanidino or guanidinoalkyl groups, at one of the nitrogen atoms a hydrogen atom may be replaced by a $C_{1-4}$-alkyl group, by a $C_{2-5}$-(alkoxycarbonyl) group, by a phenylalkoxycarbonyl, phenyloxycarbonyloxy or benzoyl group or by an alkanoyloxymethoxycarbonyl group wherein the alkanoyl moiety may contain a total of 2 to 4 carbon atoms, or by a phosphono, dialkylphosphoryl or O-alkyl-phosphono group, or, if B denotes a cyclic imine, A may also represent a hydrogen atom or a $C_{1-3}$-alkyl group, each of which is bound to the imino nitrogen, B denotes a phenylene group which may be mono- or disubstituted by fluorine, chlorine or bromine atoms, by alkyl, hydroxy, alkoxy, alkylsulphenyl, alkylsulphinyl, alkylsulphonyl, nitro, amino, alkylamino, dialkylamino, alkylcarbonylamino, alkylsulphonylamino or trifluoromethyl groups, wherein the substituents may be identical or different, and the alkyl and alkoxy moieties may each contain 1 to 3 carbon atoms, or B represents a pyridinylene or cycloalkylene group having 3 to 6 carbon atoms, a piperidinylene or piperazinylene group which may also be bound via the nitrogen atoms to carbon atoms of the adjacent groups, an indanylene or 1,2,3,4-tetrahydronaphthylene group wherein the saturated ring is bound to the group A and the aromatic ring is bound to the group C or the condensed 5-membered heterocyclic group, C represents a bond, a methylene, ethylene, phenylene, O-methylene, S-methylene, SO-methylene, $SO_2$-methylene or N-(alkyl)-methylene group each of which is bound by the heteroatom to the group B, or a methylene-N(alkyl)-group, wherein each alkyl moiety may contain 1 to 3 carbon atoms, D denotes a bond or a methylene or ethylene group, E denotes a $C_{1-5}$-alkylene group, an alkenylene or alkynylene group each having 3 to 5 carbon atoms, whilst the double or triple bond cannot be bound directly to a nitrogen atom of the -$Z_1$-$Z_2$-$Z_3$-$Z_4$- group, or, if E is not directly bound to a nitrogen atom of the -$Z_1$-$Z_2$-$Z_3$-$Z_4$-group, it may represent an —O—, —S—, —SO—, —$SO_2$—, —NH—, —N-(alkyl)-, —N(COalkyl)-, —CO—, —NH—SO—, —N(alkyl)-CO—, —CO—NH—, —CO—N(alkyl)-, —$SO_2$—NH—, —$SO_2$—N(alkyl)- or alkylsulphonylimino group, whilst each alkyl moiety may contain 1 to 3 carbon atoms, a cyclohexylene group, a piperidinylene or piperazinylene group wherein, in addition, a methylene group adjacent to a nitrogen atom may be replaced by a carbonyl group, whilst at the same time linkage to carbon atoms of the adjacent groups may be effected via the nitrogen atoms, F denotes a bond, a $C_{1-4}$-alkylene group which may be substituted by a phenyl, carboxy, alkoxycarbonyl, phenylalkoxycarbonyl or alkylaminocarbonyl group, whilst the alkylaminocarbonyl group may be substituted in the alkyl moiety (which may contain 1 to 5 carbon atoms) by a phenyl, hydroxyphenyl, methoxyphenyl, benzyloxyphenyl, carboxy, alkoxycarbonyl or phenylalkoxycarbonyl group or additionally by another carboxy, alkoxycarbonyl or phenylalkoxycarbonyl group, a cyclohexylene, cyclohexylene-alkylene or alkylene-cyclohexylene group each having 1 to 3 carbon atoms in the alkyl, alkylene and alkoxy moieties, a piperidinylene or pyrrolidinylene group, which may also be bound to the adjacent group E via the nitrogen atom if the bond is effected via a carbon atom of group E, whilst if D denotes a bond, E an oxygen atom and F an alkyl group, A cannot be an amino or acylamino group bound directly to a phenyl ring, and G represents a carbonyl group not bound to a heteroatom of group E, which may be substituted by a hydroxy group, by a cinnamyloxy group, by a $C_{1-6}$-alkoxy group (wherein a $C_{1-5}$-alkoxy group may be substituted by a phenyl group or a $C_{1-3}$-alkoxy group may be substituted in the 1-, 2- or 3-position by a naphthyl group, by a $C_{5-6}$-cycloalkyl group, by a pyridyl group or in the 2- or 3-position by a pyrrolidin-2-on-1-yl group), by a $C_{5-8}$-cycloalkoxy group, by an indanyloxy or 1,2,3,4-tetrahydronaphthyloxy group, by a bicycloheptyloxy or bicycloheptylmethoxy group (wherein the bicycloheptyl group may be substituted by 1 to 3 methyl groups) by an alkanoyloxymethoxy group having a total of 2 to 5 carbon atoms in the alkanoyl moiety, by an alkoxycarbonyloxymethoxy group having 1 to 2 carbon atoms in the alkyl moiety, or by a cycloalkoxycarbonyloxymethoxy group having 5 or 6 carbon atoms in the cycloalkyl moiety, wherein each methoxy moiety may be replaced by an alkyl group, or G may represent an O-alkylphosphono group having 1 to 3 carbon atoms or a sulpho-, phosphono- or tetrazol-5-yl group, the tautomers, the stereoisomers including the mixtures thereof and the salts thereof, particularly the physiologically acceptable salts thereof with inorganic or organic acids or bases.

Particularly preferred compounds of general formula I above, however, are those wherein $R_1$ represents a hydrogen, fluorine, chlorine or bromine atom, an alkoxy or phenylalkoxy group each having 1 to 3 carbon atoms in the alkoxy moiety, an alkoxycarbonylamino or N-alkoxycarbonylmethylamino group each having 1 to 4 carbon atoms in the alkoxy moiety, a methyl, hydroxy, amino, methylamino, dimethylamino, N-carboxymethyl-amino, N-carboxymethyl-methylamino, N-methoxycarbonylmethyl-methylamino, acetylamino, piperidino or methylsulphonylamino group, X represents an oxygen, sulphur or nitrogen atom or an —$NR_2$ group wherein $R_2$ represents a hydrogen atom, a straight-chained or branched $C_{1-14}$-alkyl group, an allyl or propargyl group, a $C_{1-3}$-alkyl group substituted by a carboxy, methoxycarbonyl, ethoxycarbonyl, aminocarbonyl, methylaminocarbonyl, dimethylaminocarbonyl, benzylaminocarbonyl, phenylethylaminocarbonyl, carboxymethylaminocarbonyl, methoxycarbonylmethylaminocarbonyl or pyridyl group or by a piperidinocarbonyl group wherein the methylene group in the 4-position may be replaced by an oxygen atom or by a sulphenyl, sulphinyl, sulphonyl, imino or benzylimino group, or $R_2$ represents a $C_{1-4}$-alkyl group which is substituted by a phenyl group optionally mono- or disubstituted by bromine or chlorine atoms or by amino, hydroxy, methoxy or methyl groups, or which is substituted by two phenyl groups, or $R_2$ represents a $C_{3-6}$-cycloalkyl group, a pyridyl group, a phenyl group optionally mono- or disubstituted by chlorine atoms or by methyl, methoxy, methylsulphenyl, methylsulphinyl or methylsulphonyl groups, wherein the substituents may be identical or different, or $R_2$ represents a $C_{2-3}$-alkyl group which is substituted in the 2- or 3-position by a hydroxy, methoxy, methylsulphenyl, methylsulphinyl, methylsulphonyl, imidazolyl or pyrrolidino group or by a piperidino group in which the methylene group in the 4-position may be replaced by an oxygen atom or by a sulphenyl, sulphinyl, sulphonyl, imino or benzylimino group, or $R_2$ represents a $C_{2-6}$-alkyl group substituted by an amino group in the 2-, 3-, 4-, 5- or 6-position, Y represents an NO group, a nitrogen atom or an optionally methyl substituted methine group, $Z_1$, $Z_2$, $Z_3$ and $Z_4$, which may be identical or different, represent methine groups, carbon atoms, imino groups or nitrogen atoms, whilst at least one of the groups $Z_1$ to $Z_4$ must comprise a carbon atom and one or two methine groups adjacent to a nitrogen atom may be replaced by carbonyl groups, $Z_5$ and $Z_6$ each represent a carbon atom or one of the groups $Z_5$ or $Z_6$ represents a nitrogen atom and the other group $Z_5$ or $Z_6$ represents a carbon atom, A represents an amino group, a straight-chained or branched $C_{1-3}$-aminoalkyl group, an amidino, guanidino or guanidinomethyl group, whilst in the above-mentioned amino, aminoalkyl, amidino, guanidino or guanidinomethyl groups, at one of the nitrogen atoms, a hydrogen atom may be replaced by a $C_{1-4}$-alkyl group, by an alkoxycarbonyl group having a total of 2 to 5 carbon atoms or by a benzoyloxycarbonyl, acetyloxymethoxycarbonyl, dimethylphosphoryl or diethylphosphoryl group, B represents a phenylene group which may be substituted by a fluorine, chlorine or bromine atom or by a methyl, hydroxy or methoxy group, a pyridinylene group or a $C_{3-6}$-cycloalkylene group, an indanylene or 1,2,3,4-tetrahydronaphthylene group wherein, in each case, the saturated ring is bound to the group A and the aromatic ring is bound to the group C or to the condensed 5-membered heterocyclic group, or B represents a piperidinylene or piperazinylene group which may also be bound via the nitrogen atoms to carbon atoms of the adjacent groups, C denotes a bond, a phenylene or an O-methylene group, D represents a bond or a methylene group, E denotes a $C_{3-5}$-alkylene group, a $C_{3-5}$-alkenylene group, in which the double bond may not be directly bound to a nitrogen atom of the $Z_1$-$Z_2$-$Z_3$-$Z_4$ group, or, if E is not directly bound to a nitrogen atom of the $Z_1$-$Z_2$-$Z_3$-$Z_4$ group, E may represent an —O—, —S—, —SO—, —$SO_2$—, —NH—, —N(methyl)-, —N(acetyl)-, —N($SO_2CH_3$)—, —CO—, —NH—CO—, —($CH_3$)—CO—, —CO—NH—, —CO—N($CH_3$)—, —$SO_2$—NH— or —$SO_2$—N($CH_3$) group, or E represents a piperidinylene, piperazinylene or oxo-piperazinylene group, whilst the nitrogen atoms may also be bound to carbon atoms of the adjacent groups, F denotes a bond, a $C_{1-4}$-alkylene group which may be substituted by a phenyl, carboxy, methoxycarbonyl, benzyloxycarbonyl, phenylethylaminocarbonyl, (methoxyphenyl)ethylaminocarbonyl or alkylaminocarbonyl group, whilst the alkylaminocarbonyl group may be substituted in the alkyl moiety, which may contain 1 to 4 carbon atoms, by a phenyl, hydroxyphenyl, methoxyphenyl, carboxy or benzyloxycarbonyl group or may additionally be substituted by a further carboxy or benzyloxycarbonyl group, a piperidinylene or pyrrolidinylene group, each of which may be bound to the adjacent group E via the nitrogen atom, provided that the bonding is effected via a nitrogen atom of the group E, or a cyclohexylene or cyclohexylene-methylene group, whilst if D denotes a bond, E denotes an oxygen atom and F denotes an alkyl group, A cannot be an amino or acylamino group bound directly to a phenyl ring, G represents a carbonyl group not bound to a heteroatom of group E, which is substituted by a hydroxy group, by a $C_{1-6}$-alkoxy group (which may be substituted in the 1-to 5-position by a phenyl group or in the 1- or 2-position by a cyclohexyl, naphthyl or pyridyl group or in the 2-position by a pyrrolidin-2-on-1-yl group), by a cinnamyloxy group, by a $C_{6-8}$-cycloalkoxy group, by an indanyloxy, norbornyloxy or norbornylmethyloxy group, by an alkanoyloxymethoxy group having a total of 2 to 5 carbon atoms in the alkanoyl moiety, by an alkoxycarbonyloxymethoxy group having 1 to 3 carbon atoms in the alkoxy moiety or by a cyclohexyloxycarbonyloxymethoxy group, wherein the methoxy part may be substituted by a methyl group, or G may represent a sulpho, phosphono, O-methyl-phosphono or tetrazol-5-yl group, particularly those compounds wherein $R_1$ is a hydrogen atom or a methyl, methoxy, methylamino, dimethylamino, N-butyloxycarbonyl-methylamino, N-isobutyloxycarbonyl-methylamino, N-carboxymethyl-amino, N-carboxymethyl-methylamino, N-methoxycarbonylmethyl-amino or N-methoxycarbonylmethyl-methylamino group, X is an oxygen or nitrogen atom or an $-NR_2$ group, wherein $R_2$ is a hydrogen atom, a straight-chained or branched $C_{1-14}$-alkyl group, a $C_{1-3}$-alkyl group which is substituted by a carboxy or methoxycarbonyl group, a $C_{1-4}$-alkyl group which is substituted by a phenyl group optionally mono- or disubstituted by bromine atoms, amino or methoxy groups, or which is substituted by two phenyl groups or by a pyridyl group, a $C_{2-3}$-alkyl group substituted in the 2- or 3-position by an amino or piperidino group in which the methylene group in the 4-position is replaced by an imino, benzylimino, sulphenyl, sulphinyl or sulphonyl group, Y represents an NO group, a nitrogen atom or a methine group, $Z_1$, $Z_2$, $Z_3$ and $Z_4$, which may be identical or different, represent methine groups, carbon atoms, imino groups or nitrogen atoms, whilst at least two of the groups $Z_1$ to $Z_4$ must comprise a carbon atom and one or two methine groups adjacent to a nitrogen atom may each be replaced by carbonyl groups, $Z_5$ and $Z_6$ each represent a carbon atom or one of the groups $Z_5$ or $Z_6$ represents a nitrogen atom and the other group $Z_5$ or $Z_6$ represents a carbon atom, A represents an aminomethyl or amidino group, wherein, at one of the nitrogen atoms, a hydrogen atom may be replaced by a methoxycarbonyl group, B denotes a phenylene group, C denotes a bond or an —O-methylene group, D denotes a bond, E denotes a $C_{3-4}$-alkylene group, or, if E is not directly bound to a nitrogen atom of the -$Z_1$-$Z_2$-$Z_3$-$Z_4$- group, E may represent an —O—, —NH—CO— or —CO—NH—group, F denotes a bond or a $C_{1-3}$-alkylene group and G denotes a carboxy group, an alkoxycarbonyl group having a total of 2 to 5 carbon atoms or a cyclohexyloxy group, the tautomers thereof, the stereoisomers thereof including the mixtures and the salts thereof, particularly the physiologically acceptable salts thereof with inorganic or organic acids or bases.

According to the invention, the new compounds of general formula I may, for example, be obtained by the following methods known per se:

a) In order to prepare compounds of general formula I wherein G denotes a carboxyl group:

Converting a compound of general formula

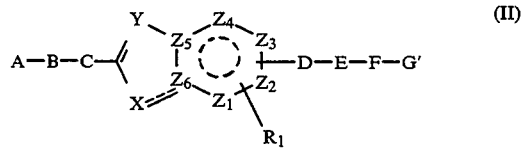

wherein

A to F, $R_1$, $Z_1$ to $Z_6$, X and Y are as hereinbefore defined and

G', which is bound to a carbon atom, denotes a group which may be converted into a carboxyl group by hydrolysis, treatment with acids, thermolysis or hydrogenolysis.

For example, functional derivatives of the carboxyl group such as unsubstituted or substituted amides, esters, thioesters, trimethylsilylesters, orthoesters, iminoesters, amidines or anhydrides, or a nitrile group may be converted by hydrolysis into a carboxyl group, esters with tertiary alcohols, e.g. tert.butylesters, may be converted by treatment with an acid or thermolysis into a carboxyl group, esters with aralkanols, e.g. benzylesters, may be converted by hydrogenolysis into a carboxyl group, and bis(alkoxycarbonyl)methyl groups may be converted by hydrolysis or treatment with an acid into a bis(hydroxy-carbonyl)methyl group which is subsequently decarboxylated.

The hydrolysis is appropriately carried out either in the presence of an acid such as hydrochloric acid, sulphuric acid, phosphoric acid, trichloroacetic acid or trifluoroacetic acid, in the presence of a base such as lithium hydroxide, sodium hydroxide or potassium hydroxide in a suitable solvent such as water, methanol, water/methanol, ethanol, water/ethanol, water/isopropanol, water/tetra-hydrofuran or water/dioxane at temperatures between $-10°$ C. and 120° C., e.g. at temperatures between ambient temperature and the boiling temperature of the reaction mixture. When treating with an organic acid such as trichloroacetic acid or trifluoroacetic acid, any alcoholic hydroxy groups present may simultaneously be converted into a corresponding acyloxy group such as a trifluoroacetoxy group.

If G' in a compound of formula II represents a cyano or aminocarbonyl group, these groups may also be converted into a carboxyl group with a nitrite, e.g. sodium nitrite, in the presence of an acid such as sulphuric acid, which may appropriately be used as the solvent at the same time, at temperatures between 0° and 50° C.

If G' in a compound of formula II represents a tert.butyloxycarbonyl group, for example, the tert.butyl group may also be cleaved by treating with an acid such as trifluoroacetic acid, formic acid, p-toluenesulphonic acid, sulphuric acid, phosphoric acid or polyphosphoric acid, optionally in an inert solvent such as methylene chloride, chloroform, benzene, toluene, tetrahydrofuran or dioxane, preferably at temperatures between $-10°$ C. and 120° C., e.g. at temperatures between 0° and 60° C., or thermally, optionally in an inert solvent such as methylene chloride, chloroform, benzene, toluene, tetrahydrofuran or dioxane and preferably in the presence of a catalytic amount of an acid such as p-toluenesulphonic acid, sulphuric acid, phosphoric acid or polyphosphoric acid, preferably at the boiling temperature of the solvent used, e.g. at temperatures between 40° C. and 100° C.

If G' in a compound of formula II represents a benzyloxycarbonyl group, for example, the benzyl group may also be hydrogenolytically cleaved in the presence of a hydrogenation catalyst such as palladium/charcoal in a suitable solvent such as methanol, ethanol, ethanol/water, glacial acetic acid, ethyl acetate, dioxane or dimethylformamide, preferably at temperatures between 0° and 50° C., e.g. at ambient temperature, under a hydrogen pressure of 1 to 10 bar. During hydrogenolysis, other groups may also be reduced at the same time, e.g. a nitro group may be reduced to an amino group or a benzyloxy group to a hydroxy group.

b) In order to prepare benzimidazoles of general formula I:
Cyclising a compound of general formula

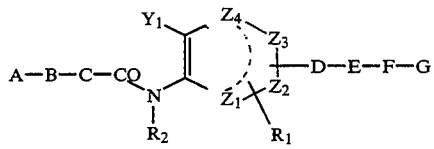

wherein
A to G, $R_1$, $R_2$ and $Z_1$ to $Z_4$ are as hereinbefore defined and
$Y_1$ represents an amino group.

The cyclising is conveniently carried out in a solvent or mixture of solvents such as methanol, ethanol, isopropanol, glacial acetic acid, benzene, chlorobenzene, toluene, xylene, glycol, glycolmonomethylether, diethyleneglycoldimethylether, sulpholane, dimethylformamide, tetraline or in an excess of the acylating agent used to prepare the compound of general formula III, e.g. in the corresponding acid or the corresponding nitrile, anhydride, acid halide, ester or amide, e.g. at temperatures between 0° and 250° C., but preferably at the boiling temperature of the reaction mixture, optionally in the presence of a condensing agent such as phosphorusoxychloride, thionylchloride, sulphurylchloride, sulphuric acid, p-toluenesulphonic acid, methanesulphonic acid, hydrochloric acid, phosphoric acid, polyphosphoric acid, acetic anhydride or optionally in the presence of a base such as potassium ethoxide or potassium tert.butoxide. However, the cyclisation may also be carried out without a solvent and/or condensing agent.

It is, however, particularly advantageous to perform the reaction by preparing a compound of general formula III in the reaction mixture by acylating a corresponding diamino compound or by reducing a corresponding o-nitro-acylamino compound. When the reduction of the nitro group is broken off at the hydroxylamine stage, the subsequent cyclisation yields the N-oxide of a compound of general formula I. The N-oxide thus obtained can subsequently be converted by reduction into a corresponding compound of general formula I.

The subsequent reduction of the resulting N-oxide of formula I is preferably carried out in a solvent such as water, water/ethanol, methanol, glacial acetic acid, ethylacetate or dimethylformamide with hydrogen in the presence of a hydrogenation catalyst such as Raney nickel, platinum or palladium/charcoal, with metals such as iron, tin or zinc in the presence of an acid such as acetic acid, hydrochloric acid or sulphuric acid, with salts such as iron(II)sulphate, tin(II)chloride or sodium dithionite, with derivatives of trivalent phosphorus such as triphenylphosphine, triethylphosphite or phosphorustrichloride, or with hydrazine in the presence of Raney nickel at temperatures between 0° and 50° C., but preferably at ambient temperature.

c) In order to prepare compounds of general formula I wherein A represents an amidino group optionally substituted by an alkyl group:
Reacting a compound of general formula

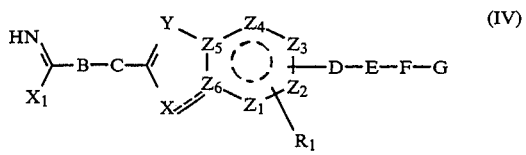

optionally formed in the reaction mixture, wherein B to G, $R_1$, $Z_1$ to $Z_6$, X and Y are as hereinbefore defined and
$X_1$ represents an alkoxy or aralkoxy group such as the methoxy, ethoxy, n-propoxy, isopropoxy or benzyloxy group or an alkylthio or aralkylthio group such as the methylthio, ethylthio, n-propylthio or benzylthio group or an amino group, with an amine of general formula $$R_a\text{---}NH_2 \qquad (V)$$

wherein
$R_a$ denotes a hydrogen atom or a $C_{1-4}$-alkyl group, or with the acid addition salts thereof. The reaction is expediently carried out in a solvent such as methanol, ethanol, n-propanol, water, methanol/water, tetrahydrofuran or dioxane at temperatures between 0° and 150° C., preferably at temperatures between 20° and 120° C., with a corresponding free amine or with a corresponding acid addition salt such as for example ammonium carbonate or acetate. A compound of general formula IV may be obtained, for example, by reacting a corresponding nitrile with a suitable alcohol such as methanol, ethanol, n-propanol, isopropanol or benzyl alcohol in the presence of an acid such as hydrochloric acid or in the presence of a corresponding alkoxide such as sodium methoxide or sodium ethoxide or by reacting a corresponding amide with a trialkyloxonium salt such as triethyloxonium-tetrafluoroborate in a solvent such as methylene chloride, tetrahydrofuran or dioxane at temperatures between −10° and 50° C., but preferably at temperatures between 0° and 20° C., or a corresponding nitrile with hydrogen sulphide, appropriately in a solvent such as pyridine or dimethylformamide and in the presence of a base such as triethylamine with subsequent alkylation of the resulting thioamide with a corresponding alkyl or aralkyl halide.

d) In order to prepare compounds of general formula I wherein A denotes an aminoalkyl group:
Reducing a compound of general formula

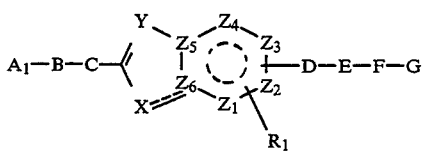

(VI)

wherein

B to G, $R_1$, $Z_1$ to $Z_6$, X and Y are as hereinbefore defined and $A_1$ denotes a cyano or cyanoalkyl group.

The reduction is preferably carried out in a suitable solvent such as methanol, methanol/water, methanol/ammonia, methanol/water/ammonia, methanol/hydrochloric acid, ethanol, ether, tetrahydrofuran, dioxane, dimethylformamide or glacial acetic acid in the presence of catalytically activated hydrogen, e.g. hydrogen in the presence of Raney nickel, platinum or palladium/charcoal or in the presence of a metal hydride such as sodium borohydride, lithium borohydride or lithium aluminium hydride at temperatures between 0° and 100° C., preferably at temperatures between 20° and 80° C.

e) In order to prepare compounds of general formula I which contain a sulphinyl or a sulphonyl group not linked to a nitrogen atom:

Oxidising a compound of general formula

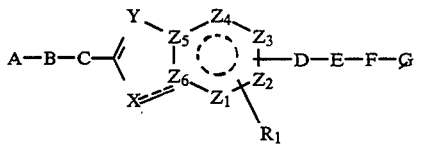

(VII)

wherein A to G, $R_1$, $Z_1$ to $Z_6$, X and Y are as hereinbefore defined, with the proviso that at least one of the groups $R_1$, B, C, E, G or X contains a sulphenyl or sulphinyl group which is not linked to a nitrogen atom.

The oxidation is preferably carried out in a solvent or mixture of solvents, e.g. in water, water/pyridine, acetone, methylene chloride, glacial acetic acid, glacial acetic acid/aceticanhydride, dilute sulphuric acid or trifluoroacetic acid, at temperatures between −80° and 100° C., depending on the oxidising agent used.

In order to prepare a corresponding S-oxide compound of general formula I oxidation is appropriately carried out with one equivalent of the oxidising agent used, e.g. with hydrogen peroxide in glacial acetic acid, trifluoroacetic acid or formic acid at 0° to 20° C. or in acetone at 0° to 60° C., with a peracid such as performic acid in glacial acetic acid or trifluoroacetic acid at 0° to 50° C. or with m-chloroperbenzoic acid in methylene chloride or chloroform at −20° to 60° C., with sodium metaperiodate in aqueous methanol or ethanol at −15° to 25° C., with bromine in glacial acetic acid or aqueous acetic acid, optionally in the presence of a weak base such as sodium acetate, with N-bromo-succinimide in ethanol, with tert.butyl-hypochlorite in methanol at −80° to −30° C., with iodobenzodichloride in aqueous pyridine at 0° to 50° C., with nitric acid in glacial acetic acid at 0° to 20° C., with chromic acid in glacial acetic acid or in acetone at 0° to 20° C. and with sulphurylchloride in methylene chloride at −70° C. and the resulting thioetherchlorine complex is conveniently hydrolysed with aqueous ethanol.

In order to prepare an S,S-dioxide compound of general formula I, oxidation is expediently carried out, starting from a corresponding alkylsulphinyl compound, with one or more equivalents of the oxidising agent used, or starting from a corresponding alkylsulphenyl compound with two or more equivalents of the oxidising agent used, e.g. with hydrogen peroxide in glacial acetic acid/aceticanhydride, trifluoroacetic acid or in formic acid at 20° to 100° C. or in acetone at 0° to 60° C., with a peracid such as performic acid or m-chloroperbenzoic acid in glacial acetic acid, trifluoroacetic acid, methylene chloride or chloroform at temperatures between 0° and 60° C., with nitric acid in glacial acetic acid at 0° to 20° C., with chromic acid or potassium permanganate in glacial acetic acid, water/sulphuric acid or in acetone at 0° to 20° C.

f) In order to prepare compounds of general formula I wherein A represents an amino, aminoalkyl, amidino, guanidino or guanidinoalkyl group substituted by an alkoxycarbonyl group having a total of 2 to 5 carbon atoms or by an arylmethoxycarbonyl, arylethoxycarbonyl, aryloxycarbonyl, alkylcarbonyl, aralkylcarbonyl or arylcarbonyl group:

Reacting a compound of general formula

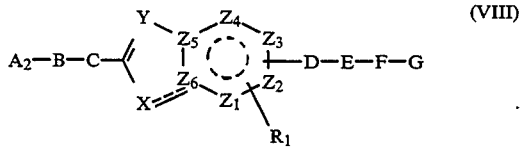

(VIII)

wherein

B to G, $R_1$, $Z_1$ to $Z_6$, X and Y are as hereinbefore defined and $A_2$ represents an amino, aminoalkyl, amidino, guanidino or guanidinoalkyl group, with a compound of general formula $$X_2-COR_b \qquad (IX)$$

wherein $R_b$ represents a $C_{1-4}$-alkoxy group, an arylmethoxy, arylethoxy, aryloxy, alkyl, aralkyl or aryl group and $X_2$ denotes a nucleophilic leaving group such as a halogen atom, e.g. a chlorine or bromine atom.

The reaction is conveniently carried out in a solvent such as tetrahydrofuran, methylene chloride, chloroform or dimethylformamide, expediently in the presence of a base such as sodium carbonate, potassium carbonate or sodium hydroxide solution or in the presence of a tertiary organic base such as triethylamine, N-ethyl-diisopropylamine, N-methyl-morpholine or pyridine, which may simultaneously serve as solvent, at temperatures between −30° and 100° C., but preferably at temperatures between −10° and 80° C.

g) In order to prepare compounds of general formula I wherein G represents a carbonyl group not bound to a heteroatom of group E, which is substituted by a cinnamyloxy group, by a $C_{1-6}$-alkoxy group (wherein a $C_{1-5}$-alkoxy group may be substituted by a phenyl group or a $C_{1-3}$-alkoxy group may be substituted in the 1-, 2- or 3-position by a naphthyl group, by a $C_{5-6}$-cycloalkyl group, by a pyridyl group or in the 2- or 3-position by a pyrrolidin-2-on-1-yl group), by a $C_{5-8}$-cycloalkoxy group, by an indanyloxy, 1,2,3,4-tetrahydronaphthyloxy, bicycloheptyloxy or bicycloheptylmethoxy group, by an alkanoyloxymethoxy group having a total of 2 to 5 carbon atoms in the alkanoyl moiety, by an alkoxycarbonyloxy-methoxy group having 1 to 2 carbon atoms in the alkyl moiety, or by a cycloalkoxycarbonyloxymethoxy group having 5 or 6 carbon atoms in the cycloalkyl moiety, wherein the methoxy moiety may in each case be substituted by an alkyl group:

Reacting a compound of general formula

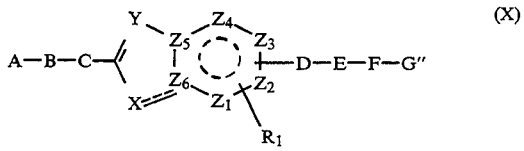

(X)

wherein

A to F, R$_1$, Z$_1$ to Z$_6$, X and Y are as hereinbefore defined and

G' represents a carboxy or alkoxycarbonyl group, with an alcohol of general formula $$X_3-R_c \quad (XI)$$

wherein

X$_3$ represents a hydroxy group or a nucleophilic leaving group such as a halogen atom, e.g. a chlorine, bromine or iodine atom, and R$_c$ represents a cinnamyl group, a C$_{1-6}$-alkyl group (wherein a C$_{1-5}$-alkyl group may be substituted by a phenyl group or a C$_{1-3}$-alkyl group may be substituted in the 1-, 2- or 3-position by a naphthyl group, by a C$_{5-6}$-cycloalkyl group, by a pyridyl group or in the 2- or 3-position by a pyrrolidin-2-on-1-yl group), a C$_{5-8}$-cycloalkyl group, an indanyl, 1,2,3,4-tetrahydronaphthyl, bicycloheptyl or bicycloheptylmethyl group, an alkanoyloxymethyl group having a total of 2 to 5 carbon atoms in the alkanoyl moiety, an alkoxycarbonyloxymethyl group having 1 to 2 carbon atoms in the alkyl moiety, or a cycloalkoxycarbonyloxymethyl group having 5 or 6 carbon atoms in the cycloalkyl moiety, wherein each methyl moiety may be substituted by an alkyl group.

The reaction is conveniently carried out in a solvent or mixture of solvents such as methylene chloride, dimethylformamide, dimethylsulphoxide, toluene, chlorobenzene, tetrahydrofuran, toluene/tetrahydrofuran or dioxane, optionally in the presence of an acid such as hydrochloric acid or in the presence of a dehydrating agent, e.g. in the presence of isobutylchloroformate, thionylchloride, trimethylchlorosilane, titanium tetrachloride, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexyl-carbodiimide-/N-hydroxysuccinimide or 1-hydroxy-benzotriazole, N,N'-carbonyldiimidazole or N,N'-thionyldiimidazole or triphenylphosphine/carbon tetrachloride, or in the presence of a base such as sodium carbonate, potassium carbonate, sodium hydroxide solution, triethylamine, N-ethyl-diisopropylamine, N-methyl-morpholine, pyridine or 4-dimethylamino-pyridine, appropriately at temperatures between 0° and 150° C., preferably at temperatures between 0° and 50° C.

If X$_3$ denotes a nucleophilic leaving group, the reaction is conveniently carried out in a solvent such as methylene chloride, tetrahydrofuran, dioxane, dimethylsulphoxide or dimethylformamide, optionally in the presence of a reaction accelerator such as sodium or potassium iodide and preferably in the presence of a base such as sodium carbonate, potassium carbonate or sodium hydroxide solution or in the presence of a tertiary organic base such as N-ethyl-diisopropylamine or N-methyl-morpholine, which may simultaneously serve as solvent, or optionally in the presence of silver carbonate or silver oxide at temperatures between −30° and 100° C., but preferably at temperatures between −10° and 80° C.

If X$_3$ denotes a hydroxy group, the esterification is conveniently carried out in a solvent or mixture of solvents such as methylene chloride, dimethylformamide, dimethylsulphoxide, toluene, chlorobenzene, tetrahydrofuran, toluene/tetrahydrofuran or dioxane, optionally in the presence of an acid such as hydrochloric acid or in the presence of a dehydrating agent, e.g. in the presence of isobutylchloroformate, thionylchloride, trimethylchlorosilane, titanium tetrachloride, hydrochloric acid, sulphuric acid, methanesulphonic acid, p-toluenesulphonic acid, phosphorus trichloride, phosphorus pentoxide, N,N'-dicyclohexylcarbodiimide, N,N'-dicyclohexyl-carbodiimide/N-hydroxysuccinimide or 1-hydroxy-benzotriazole, N,N'-carbonyldiimidazole or N,N'-thionyldiimidazole or triphenylphosphine/carbon tetrachloride at temperatures between −30° and 100° C., but preferably at temperatures between −10° and 60° C.

h) In order to prepare compounds of general formula I wherein A denotes a guanidinoalkyl group or an amidino group bound to the nitrogen atom of a cyclic imino group:

Reacting a compound of general formula

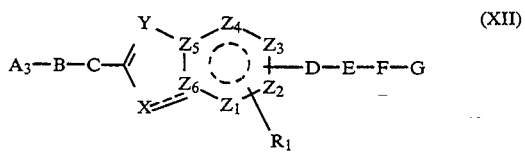

(XII)

wherein

B to G, R$_1$, Z$_1$ to Z$_6$, X and Y are as hereinbefore defined and

A$_3$ denotes an aminoalkyl group, or a compound of general formula

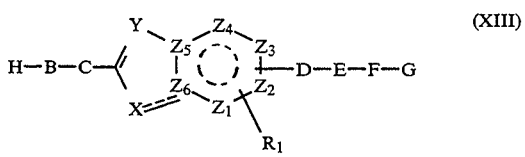

(XIII)

wherein

B to G, R$_1$, Z$_1$ to Z$_6$, X and Y are as hereinbefore defined, with the proviso that the group B contains a cyclic imino group, with an S-alkyl-isothiourea.

The reaction is conveniently carried out in a solvent such as dimethylformamide and preferably in the presence of a base such as sodium carbonate at elevated temperatures, e.g. at temperatures between 80° and 120° C.

i) In order to prepare compounds of general formula I wherein A represents a guanidino group bound to an aromatic ring:

Reacting a compound of general formula

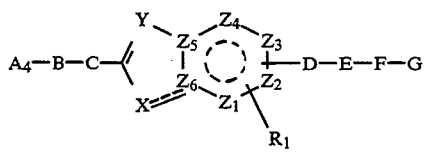
(XIV)

wherein
B to G, $R_1$, $Z_1$ to $Z_6$, X and Y are as hereinbefore defined, with the proviso that B denotes an aromatic or heteroaromatic ring, and
$A_4$ denotes an amino group, with cyanamide or an acid addition salt thereof.

The reaction is conveniently carried out in a solvent such as dioxane, dioxane/water or tetrahydrofuran, preferably at temperatures between 60° and 120° C., e.g. at the boiling temperature of the reaction mixture.

j) In order to prepare compounds of general formula I wherein D represents a bond and E denotes an —NR$_3$—CO—group:

Reacting a compound of general formula

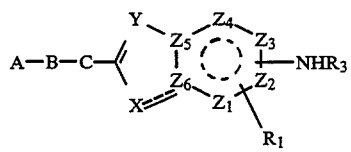
(XV)

wherein
A to C, $R_1$, $R_3$, $Z_1$ to $Z_6$, X and Y are as hereinbefore defined, with a compound of general formula

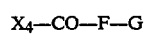
$X_4$—CO—F—G (XVI)

wherein
F and G are as hereinbefore defined and
$X_4$ denotes a nucleophilic leaving group such as a hydroxy or alkoxy group or a halogen atom, e.g. a chlorine, bromine or iodine atom or a methoxy or ethoxy group, or with the reactive derivatives thereof.

The reaction is expediently carried out in a solvent such as methylene chloride, chloroform, carbon tetrachloride, ether, tetrahydrofuran, dioxane, benzene, toluene, acetonitrile or dimethylformamide, optionally in the presence of an acid-activating agent or a dehydrating agent, e.g. in the presence of ethylchloroformate, thionylchloride, phosphorus trichloride, phosphorus pentoxide, N,N'-dicyclohexylcarbodiimide, N,N'-dicyclohexylcarbodiimide/N-hydroxysuccinimide, N,N'-carbonyldiimidazole or N,N'-thionyldiimidazole or triphenylphosphine/carbon tetrachloride, optionally in the presence of an inorganic base such as sodium carbonate or a tertiary organic base such as triethylamine, pyridine or 4-dimethylamino-pyridine, which may simultaneously be used as solvent, at temperatures between —25° and 150° C., but preferably at temperatures between —10° C. and the boiling temperature of the solvent used. However, the acylation is carried out as described above, preferably with a corresponding acid halide or acid anhydride, but may also be carried out without a solvent.

k) In order to prepare compounds of general formula I wherein A denotes an amino or aminoalkyl group:

Reacting a compound of general formula

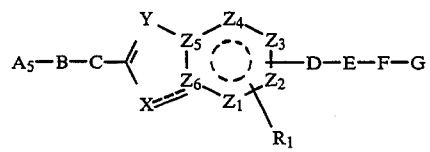
(XVII)

wherein
$R_1$, B to G, X, Y and $Z_1$ to $Z_6$ are as hereinbefore defined and
$A_5$ denotes an H$_2$N—CO—T group, wherein T denotes a bond or a $C_{1-4}$-alkylene group, with a phenyliodo(III) compound of general formula

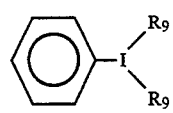
(XVIII)

wherein
$R_9$ denotes the acyl group of an organic carboxylic acid such as the acetoxy or trifluoroacetoxy group.

The reaction is preferably carried out in an aqueous solvent such as water or water/acetonitrile at temperatures between 0° and 50° C., but preferably at ambient temperature.

l) In order to prepare compounds of general formula I wherein A denotes an aminoalkyl group, in which the amino group is not bound to a quaternary carbon atom, or an amino group which is bound to a CH or CH$_2$ group of the group B or C:

Reducing a compound of general formula

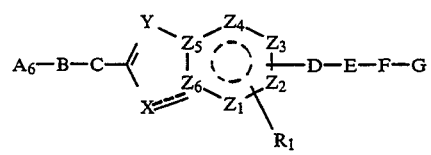
(XIX)

wherein
$R_1$, B to G, X, Y and $Z_1$ to $Z_6$ are as hereinbefore defined and
$A_6$ denotes a hydroxyimino or hydroxyiminoalkyl group having 1 to 4 carbon atoms.

The reduction is preferably carried out in a suitable solvent such as methanol, methanol/water, methanol/water/ammonia, ethanol, ether, tetrahydrofuran, dioxane or dimethylformamide, optionally with the addition of an acid such as hydrochloric acid, in the presence of catalytically activated hydrogen, e.g. hydrogen in the presence of Raney nickel, platinum or palladium/charcoal, at temperatures between 0° and 100° C., preferably at temperatures between 20° and 80° C.

m) In order to prepare compounds of general formula I wherein A denotes an amino, aminoalkyl, amidino, guanidino or guanidinoalkyl group substituted by a dialkylphosphoryl group having 1 to 3 carbon atoms in each alkyl moiety:

Reacting a compound of general formula

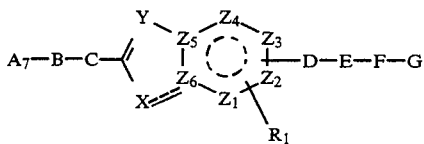 (XX)

wherein $R_1$, B to G, X, Y and $Z_1$ to $Z_6$ are as hereinbefore defined and $A_7$ denotes an amino group, a straight-chained or branched $C_{1-4}$-aminoalkyl group, an amidino, guanidino or guanidinoalkyl group having 1 to 3 carbon atoms in the alkyl moiety, with a compound of general formula $X_5$—PO(OR$_{10}$)$_2$ (XXI)

wherein $R_{10}$ denotes a $C_{1-3}$-alkyl group and $X_5$ represents a nucleophilic leaving group such as a cyano group or a chlorine or bromine atom.

The reaction is conveniently carried out in a solvent such as dimethylformamide at temperatures between 0° and 100° C., preferably at temperatures between 15° and 50° C.

n) In order to prepare compounds of general formula I wherein E denotes a —CO—NR$_3$— group:

Reacting a compound of general formula

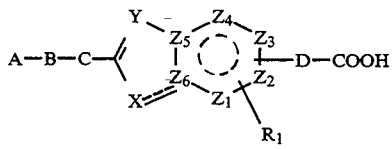 (XXII)

wherein

A to D, X, Y and $Z_1$ to $Z_6$ are as hereinbefore defined, with a compound of general formula

HNR$_3$—F—G (XXIII)

wherein

F, G and $R_3$ are as hereinbefore defined.

The reaction is expediently carried out in a solvent such as methylene chloride, chloroform, carbon tetrachloride, ether, tetrahydrofuran, dioxane, benzene, toluene, acetonitrile or dimethylformamide, optionally in the presence of an acid activating agent or a dehydrating agent, e.g. in the presence of ethylchloroformate, thionylchloride, phosphorus trichloride, phosphorus pentoxide, N,N'-dicyclohexyl-carbodiimide, N,N'-dicyclohexylcarbodiimide/N-hydroxysuccinimide, N,N'-dicyclohexylcarbodiimide/1-hydroxybenzotriazole, 2-(1H-benzotriazol-1-yl)-1,1,3,3-tetramethyluronium-tetrafluoroborate, N,N'-carbonyldiimidazole or N,N'-thionyldiimidazole or triphenylphosphine/carbon tetrachloride, optionally in the presence of an inorganic base such as sodium carbonate or a tertiary organic base such as triethylamine, N-methyl-morpholine, pyridine or 4-dimethylaminopyridine, which may simultaneously serve as solvents, at temperatures between —25° and 150° C., but preferably at temperatures between —10° C. and the boiling temperature of the solvent used.

If according to the invention a compound of general formula I is obtained wherein $R_1$ represents one of the amino or aminoalkyl groups mentioned hereinbefore, this may be converted by alkylation into a corresponding alkylamino or dialkylamino compound of general formula I.

The subsequent alkylation is conveniently carried out in a solvent or mixture of solvents such as methylene chloride, dimethylformamide, dimethylsulphoxide, toluene, chlorobenzene, tetrahydrofuran, toluene/tetrahydrofuran or dioxane, optionally in the presence of a base such as sodium carbonate, potassium carbonate, sodium hydroxide solution, potassium tert.butoxide or N-ethyl-diisopropylamine at temperatures between 0° and 150° C., preferably at temperatures between 0° and 50° C.

In the reactions described hereinbefore, any reactive groups present such as hydroxy, carboxy, phosphono, amino, alkylamino or imino groups may be protected during the reaction by means of conventional protecting groups which are cleaved again after the reaction. For example, the protective group for a hydroxy group may be a trimethylsilyl, acetyl, benzoyl, tert.butyl, trityl, benzyl or tetrahydropyranyl group, the protecting group for a carboxyl group may be a trimethylsilyl, methyl, ethyl, tert.butyl, benzyl or tetrahydropyranyl group, the protecting group for a phosphono group may be a trimethylsilyl, methyl, ethyl or benzyl group, and the protecting group for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and for the amino group a phthalyl group may also be considered.

The optional subsequent cleaving of a protecting group may, for example, be carried out hydrolytically in an aqueous solvent, e.g. in water, isopropanol/water, tetrahydrofuran/water or dioxane/water, in the presence of an acid such as trifluoroacetic acid, hydrochloric acid, hydrobromic acid or sulphuric acid or in the presence of an alkali metal base such as lithium hydroxide, sodium hydroxide or potassium hydroxide or by ether cleaving, e.g. in the presence of iodotrimethylsilane, at temperatures between 0° and 100° C., preferably at temperatures between 10° and 50° C.

However, a benzyl, methoxybenzyl or benzyloxycarbonyl group may be cleaved hydrogenolytically, for example, using hydrogen in the presence of a catalyst such as palladium/charcoal in a solvent such as methanol, ethanol, ethyl acetate or glacial acetic acid, optionally with the addition of an acid such as hydrochloric acid at temperatures between 0° and 50° C., but preferably at ambient temperature, under a hydrogen pressure of 1 to 7 bar, preferably 3 to 5 bar.

A methoxybenzyl group may also be cleaved in the presence of an oxidising agent such as cerium(IV)ammonium nitrate in a solvent such as methylene chloride, acetonitrile or acetonitrile/water at temperatures between 0° and 50° C., but preferably at ambient temperature.

However, a 2,4-dimethoxybenzyl group is preferably cleaved in trifluoroacetic acid in the presence of anisole.

The cleaving of only one alkyl group form an O,O'-dialkyl-phosphono group is preferably carried out using sodium iodide in a solvent such as acetone, ethylmethylketone, acetonitrile or dimethylformamide at temperatures between 40° and 150° C., but preferably at temperatures between 60° and 100° C.

The cleaving of both alkyl groups from an O,O'-dialkylphosphono group is carried out, for example, with iodotrimethylsilane, bromotrimethylsilane or chlorotrimethylsilane/sodium iodide in a solvent such as methylene chloride, chloroform or acetonitrile at temperatures between 0° C. and the boiling point of the reaction mixture, but preferably at temperatures between 20° and 60° C.

A tert.butyl or tert.butyloxycarbonyl group is preferably cleaved by treating with an acid such as trifluoroacetic acid or hydrochloric acid, optionally using a solvent such as methylene chloride, dioxane or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20° and 50° C.

Furthermore, the compounds of general formula I obtained may be resolved into their enantiomers and/or diastereomers as mentioned hereinbefore. Thus, for example, cis/trans mixtures may be resolved into their cis and trans isomers, and compounds having at least one optically active carbon atom may be resolved into their enantiomers.

Thus, for example, the cis/trans mixtures obtained may be resolved by chromatography into the cis and trans isomers thereof and the compounds of general formula I which occur in racemate form may be separated by methods known per se (cf. Allinger N. L. and Eliel E. L. in "Topics in Stereochemistry", Vol. 6, Wiley Interscience, 1971) into their optical antipodes and compounds of general formula I having at least 2 asymmetric carbon atoms may be separated on the basis of their physical-chemical differences using known methods, e.g. by chromatography and/or fractional crystallisation, into the diastereomers thereof which, if they occur in racemic form, may subsequently be separated into the enantiomers as mentioned above.

The separation of enantiomers is preferably effected by column separation on chiral phases or by recrystallisation from an optically active solvent or by reacting with an optically active substance which forms salts or derivatives such as esters or amides with the racemic compound, especially acids and the activated derivatives or alcohols thereof, and separation of the diastereomeric salt mixture or derivative thus obtained, e.g. on the basis of their different solubilities, whilst the free antipodes may be released from the pure diastereomeric salts or derivatives by the action of suitable agents. Particularly common, optically active acids include, for example, the D- and L-forms of tartaric acid or dibenzoyltartaric acid, di-o-tolyl tartaric acid, malic acid, mandelic acid, camphorsulphonic acid, glutamic acid, aspartic acid or quinic acid. The optically active alcohol may be (+)- or (−)-menthol, for example, and the optically active acyl group in amides may be, for example, (+)- or (−)-menthyloxycarbonyl.

Moreover, the compounds of formula I obtained may be converted into the salts thereof, particularly for pharmaceutical use into the physiologically acceptable salts thereof with inorganic or organic acids. Examples of suitable acids include hydrochloric acid, hydrobromic acid, sulphuric acid, phosphoric acid, acetic acid, fumaric acid, succinic acid, lactic acid, citric acid, tartaric acid or maleic acid.

In addition, the new compounds of formula I thus obtained, if they contain a carboxyl group, may subsequently, if desired, be converted into the addition salts thereof with inorganic or organic bases, more particularly, for pharmaceutical use, into the physiologically acceptable addition salts thereof. Examples of suitable bases include sodium hydroxide, potassium hydroxide, ammonia, cyclohexylamine, ethanolamine, diethanolamine and triethanolamine.

The compounds used as starting materials are known from the literature in some cases or may be obtained by methods known from the literature, as described in Examples I to XXIII.

As already mentioned, the new condensed 5-membered heterocylic compounds of general formula I and the addition salts thereof, particularly the physiologically acceptable addition salts thereof with inorganic or organic acids or bases, have valuable properties. Thus, the new compounds of general formula I, wherein A contains an amino, aminoalkyl, amidino, guanidino or guanidinoalkyl group optionally substituted at the nitrogen or a group which may optionally be converted in vivo into an amino, amidino or guanidino group optionally substituted at the nitrogen, e.g. an amino, aminoalkyl, amidino, guanidino or guanidinoalkyl group substituted at the nitrogen by an alkoxycarbonyl, alkenyloxycarbonyl, aralkoxycarbonyl, alkylcarbonyl, arylcarbonyl, aryloxycarbonyl, alkanoyloxymethoxycarbonyl, cycloalkanoyloxymethoxycarbonyl, aralkanoyloxymethoxycarbonyl, aryloxymethoxycarbonyl, phosphono, dialkylphosphoryl or O-alkylphosphono group, or B denotes a cyclic imino group optionally alkylated at the nitrogen atom and -D-E-F contains carboxyl, sulpho, phosphono, O-alkyl-phosphono or 5-tetrazolyl groups or groups which can be converted in vivo into carboxyl, sulpho, phosphono, O-alkyl-phosphono or tetrazolyl groups, e.g. carbonyl groups substituted by an alkoxy, aralkoxy, aralkenyloxy, cycloalkylalkoxy, heteroarylalkoxy, pyrrolidin-2-on-1-ylalkoxy, morpholinoalkoxy, thiomorpholinoalkoxy, 1-oxido-thiomorpholinoalkoxy, cycloalkoxy, benzocycloalkoxy, bicycloalkoxy, bicycloalkylalkoxy, alkanoyloxymethoxy, cycloalkylalkanoyloxymethoxy, alkoxycarbonyloxymethoxy, aroyloxymethoxy, aralkanoyloxymethoxy, aryloxycarbonyloxymethoxy or aralkoxycarbonyloxymethoxy group, have valuable pharmacological properties and in addition to having an inhibitory effect on inflammation and bone degradation, have, in particular, antithrombotic, antiaggregatory and tumour- or metastasis-inhibiting effects.

The compounds of general formula I wherein A denotes a cyano group are valuable intermediate products for preparing the corresponding aminomethyl and amidino compounds of general formula I.

By way of example, the compounds of general formula I were investigated for their biological effects as follows:

1. Fibrinogen Binding to Human Thrombocytes

The blood obtained by puncturing an antecubital vein is anticoagulated with trisodium citrate (final concentration: 13 mM) and centrifuged for 10 minutes at 170× g. The supernatant platelet-rich plasma is poured onto a Sepharose 2B column (Pharmacia) and eluted with a solution of 90 mM common salt, 14 mM trisodium citrate, 5 mM glucose and 50 mM tris(hydroxymethyl)aminomethane, adjusted to pH 7.4. The gel-filtered platelets (GFP) appearing before the plasma proteins are used for the binding experiments.

50 μl of a 60 mM calcium chloride solution, 50 μl of a 0.6 mM adenosine diphosphate solution, 100 μl of substance solution or solvent and 50 μl of fibrinogen solution (containing 3 μg of $^{125}$fibrinogen) are added to 750 μl of GFP and incubated for 20 minutes at ambient temperature. The non-specific binding is determined in the presence of 3 mg/ml of cold fibrinogen.

900 μl of the incubated material are carefully pipetted onto 250 μl of silicon oil (AP 38: AR 20, 1:2 v/v, Wacker Chemie) in Eppendorf tubes and centrifuged for 2 minutes at 10,000× g. The aqueous supernatant and some of the oil are drawn off, the tips of the tubes are cut off together with the platelet pellet and the quantity of bound fibrinogen is determined in a gamma counter. The concentration of substance which brings about a 50% inhibition in fibrinogen binding is determined from a series of concentrations and is given as the $IC_{50}$ value.

2. Antithrombotic Activity

Method

The thrombocyte aggregation is measured using the Born and Cross method (*J. Physiol.* 170:397 (1964)) in platelet-rich plasma taken from healthy volunteers. To inhibit coagulation the blood is mixed with 3.14% sodium citrate in a ratio by volume of 1:10.

Collagen-induced aggregation

The pattern of the decrease in optical density of the platelet suspension is photometrically measured and recorded after the addition of aggregation-triggering substance. The rate of aggregation is concluded from the angle of inclination of the density curve. The point on the curve where there is maximum light transmittance is used to calculate the optical density.

The amount of collagen used is as small as possible but sufficient to produce an irreversible reaction curve. Standard commercial collagen produced by Hormonchemie of Munich is used. Before the addition of the collagen the plasma is incubated for 10 minutes with the substance at 7° C.

From the measurements obtained an $EC_{50}$ is determined graphically, indicating a 50% change in the optical density in terms of the inhibition of aggregation.

The Table which follows contains the results found:

| Substance (Example No.) | Fibrinogen binding test $IC_{50}[nM]$ | Inhibition of platelet aggregation $EC_{50}[nM]$ |
|---|---|---|
| 1 | 33,000 | 27,000 |
| 1(1) | 600 | 6,600 |
| 1(2) | 720* | 3,300 |
| 1(3) | 37 | 70 |
| 1(62) | 38* | |
| 1(73) | 49* | 160 |
| 1(74) | 120* | 310 |
| 1(75) | 230* | 1,100 |
| 1(76) | 28 | 1,150 |
| 1(79) | 41 | 80 |
| 1(135) | 800 | 7,600 |
| 1(136) | 30 | 80 |
| 1(137) | 1,800* | 7,000 |
| 1(138) | 1,500* | 3,600 |
| 1(139) | 410* | 1,500 |
| 1(140) | 220* | 750 |
| 1(160) | 7.5* | 70 |
| 3 | | 1,200 |
| 3(19) | 280* | 330 |
| 3(48) | 7,000* | 6,400 |
| 3(52) | 4,800* | 9,500 |
| 3(59) | 2,000* | 3,800 |
| 3(119) | 4,600* | 39,000 |
| 3(120) | 1,300* | 2,000 |
| 3(121) | 15,000* | 13,000 |
| 3(122) | 4,000* | 8,600 |
| 3(123) | 25,000* | 12,000 |
| 3(124) | 17,000* | 2,800 |
| 3(125) | 2,000 | 250 |
| 3(126) | 2,200 | 9,900 |
| 3(130) | 14,000 | 160 |
| 3(141) | 140 | 80 |
| 5 | 15,000* | 43,000 |
| 5(6) | 5,500* | 18,000 |
| 6 | 4,000 | 3,700 |
| 13 | 1,700* | 5,700 |
| 13(3) | 1,400* | 4,300 |
| 13(6) | 130* | 980 |
| 15 | 28 | 40 |
| 15(1) | 2,500* | 4,100 |
| 17 | 1,000 | 3,800 |
| 17(1) | 700 | 1,530 |
| 17(2) | 22* | 80 |
| 17(3) | 170* | 430 |
| 17(4) | 1,900* | >100,000 |
| 17(5) | 370* | 2,130 |
| 17(6) | 1,800* | 30,000 |
| 17(7) | 5.4* | 290 |
| 17(8) | 47* | 350 |
| 17(9) | 9.5* | 1,140 |
| 17(10) | 26,000 | 27,000 |
| 17(13) | 20* | 40 |

*$^{125}$I fibrogen was replaced by 3H-(3S,5S)-5-[(4'-amidino-4-biphenylyl)-oxymethyl]-3-carboxymethyl-2-pyrrolidone.

The compounds according to the invention are well tolerated because after intravenous administration of 30 mg/kg of the compound of Example 1(3) to three mice, no animals died.

In the light of their inhibitory effect on cell-cell or cell-matrix interactions, the new condensed 5-membered heterocyclic compounds of general formula I and the physiologically acceptable addition salts thereof are suitable for combating or preventing diseases in which smaller or greater cell aggregates occur or in which cell-matrix interactions play a part, e.g. in treating or preventing venous and arterial thrombosis, cerebrovascular diseases, lung embolism, cardiac infarction, arteriosclerosis, osteoporosis and the metastasis of tumours and the treatment of genetically caused or acquired disorders of cell interactions with one another or with solid structures. They are also suitable for parallel therapy in thrombolysis with fibrinolytics or vascular interventions such as transluminal angioplasty or in the treatment of shock, psoriasis, diabetes and inflammation.

For treating or preventing the diseases mentioned above the dosage is between 0.1 μg and 30 mg/kg of body weight, preferably 1 μg to 15 mg/kg of body weight, given in up to 4 doses per day. For this purpose the compounds of formula I produced according to the invention, optionally in conjunction with other active substances such as thromboxane receptor antagonists and thromboxane synthesis inhibitors or combinations thereof, serotonin antagonists, α-receptor antagonists, alkylnitrates such as glycerol trinitrate, phosphodiesterase inhibitors, prostacyclin and the analogues thereof, fibrinolytics such as tPA, prourokinase, urokinase, streptokinase, or anticoagulants such as heparin, dermatane sulphate, activated protein C, vitamin K antagonists, hirudine, inhibitors of thrombin or other activated clotting factors, may be incorporated together with one or more inert conventional carriers and/or diluents, e.g. corn starch, lactose, glucose, microcrystalline cellulose, magnesium stearate, polyvinylpyrrolidone, citric acid, tartaric acid, water, water/ethanol, water/glycerol, water/sorbitol, water/polyethylene-glycol, propyleneglycol, stearylalcohol, carboxymethylcellulose or fatty substances such as hard fat or suitable mixtures thereof, into conventional galenic preparations such as plain or coated tablets, capsules, powders, suspensions, solutions, sprays or suppositories.

The Examples which follow are intended to illustrate the invention:

EXAMPLE I

4-[N-(4-Amidino-benzoyl)-methylamino]-3-nitro-benzoic acid-[N-(3-methoxycarbonyl-propyl)-amide]

Prepared analogously to Example 3 from 4-[4-[N-(4-cyano-benzoyl)-methylamino]-3-nitro-benzoic acid-[N-(3-methoxycarbonyl-propyl)-amide].

$R_f$-value: 0.11 (silica gel; ethyl acetate/ethanol=7:3).

The following compound is obtained analogously:
(1) 4-[N-(4-amidino-benzoyl)-methylamino]-3-nitro-benzoic acid-[N-(2-methoxycarbonyl-ethyl)-amide]

$R_f$-value: 0.11 (silica gel; ethyl acetate/ethanol=7:3).

EXAMPLE II

4-[N-(4-Cyano-benzoyl)-methylamino]-3-nitro-benzoic acid-[N-(3-methoxycarbonyl-propyl)-amide]

2.84 g of N-ethyl-diisopropylamine are added, with cooling to 0° C., to a mixture of 3.2 g of 4-[N-(4-cyano-benzoyl)-methylamino]-3-nitro-benzoylchloride, 1.68 g of methyl 4-aminobutyrate-hydrochloride and 50 ml of methylene chloride. The mixture is stirred for 64 hours and allowed to return to ambient temperature. The methylene chloride is evaporated off and the residue is purified over silica gel (eluant:ethyl acetate/ethanol=200:1). Yield: 3.9 g (100% of theory), $R_f$-value: 0.62 (silica gel; ethyl acetate/ethanol=9:1)

The following compounds are obtained analogously:
(1) 4-[N-(4-cyano-benzoyl)-methylamino]-3-nitro-benzoic acid-[N-(2-methoxycarbonyl-ethyl)-amide]

$R_f$-value: 0.75 (silica gel; ethyl acetate/ethanol=9:1)
(2) ethyl 4-[(4-cyano-phenyl)-oxymethylcarbonylamino]-3-nitro-phenoxy]-acetate 4-dimethylamino-pyridine is used as the base.

Melting point: 151°–153° C.
(3) 4-[2-(4-benzyl-piperazino)-ethylamino]-3-(4-cyano-benzoyl-amino)-benzoic acid-[N-(2-methoxycarbonyl-ethyl)-amide]

The work is done in pyridine at ambient temperature. $R_f$-value: 0.73 (silica gel; methylene chloride/methanol=9:1, after developing twice)
(4) 5-(4-cyano-benzoylamino)-2,4-bis-methylamino-benzoic acid-[N-(2-methoxycarbonyl-ethyl)-amide]

The work is done with 4-dimethylamino-pyridine as base.

Melting point: 208°–210° C. $R_f$-value: 0.71 (silica gel; methylene chloride/methanol/conc. ammonia=9:1:0.1, after developing three times)
(5) 4-chloro-2-methoxy-5-nitro-benzoic acid-[N-(2-methoxycarbonyl-ethyl)-amide]

A mixture of 4-chloro-2-methoxy-5-nitro-benzoylchloride, β-alanine-methylester-hydrochloride and toluene is refluxed for 48 hours.

Melting point: 74°–76° C. $R_f$-value: 0.43 (silica gel; methylene chloride/methanol=30:1)
(6) 6-methylamino-5-nitro-nicotinic acid-[N-(2-carboxyethyl)-amide]

This work is done with 1N NaOH at room temperature, whereby 6-methylamino-5-nitro-nicotinic acid chloride (prepared from the acid and thionyl chloride) dissolved in methylene chloride was added. $R_f$ value: 0.47 (Reversed-Phase-Plate RP18; methanol/5% sodium chloride solution=6:4)
(7) 4-chloro-3-nitro-benzoic acid-(2-carboxy-pyrrolidide)

The same procedure is used as in (6). $R_f$-value: 0.43 (silica gel; ethyl acetate/ethanol/glacial acetic acid=8:2:0.1)
(8) 4-chloro-3-nitro-benzoic acid-(3-carboxy-piperidide)

The same procedure is used as in (6).

melting point: 211°–213° C. $R_f$-value: 0.69 (silica gel; ethyl acetate/ethanol/glacial acetic acid=8:2:0.1)

EXAMPLE III

4-[N-(4-Cyano-benzoyl)-methylamino]-3-nitro-benzoylchloride

A mixture consisting of 6.2 g of 4-[N-(4-cyano-benzoyl)-methylamino]-3-nitro-benzoic acid and 20 ml of thionylchloride is refluxed until a clear solution has formed. Excess thionylchloride is evaporated off in vacuo and the residue is used further without any additional purification.

The following compound is obtained analogously:
(1) 4-chloro-2-methoxy-5-nitro-benzoylchloride The mixture is refluxed for 18 hours. The product is further used without purification.

EXAMPLE IV

4-[N-(4-Cyano-benzoyl)-methylamino]-3-nitro-benzoic acid 9.9 g of methyl 4-[N-(4-cyano-benzoyl)-methylamino]-3-nitro-benzoate are dissolved, with gentle heating, in a mixture of 290 ml of tetrahydrofuran and 290 ml of water and 29 ml of 1N lithium hydroxide solution are then added with stirring at ambient temperature. The mixture is stirred for a further 25 minutes, 29 ml of 1N hydrochloric acid are added and the tetrahydrofuran is distilled off in vacuo, whereupon the product is partially precipitated. The aqueous phase remaining is acidified with hydrochloric acid and extracted with ethyl acetate, a further fraction being obtained after evaporation of the ethyl acetate. The product is purified by taking up in hot tetrahydrofuran and precipitating with petroleum ether. Yield: 7.5 g (79% of theory), Melting point: 220°–222 C. $R_f$-value: 0.22 (silica gel; ethyl acetate/ethanol=9:1)

EXAMPLE V

Methyl 4-[N-(4-cyano-benzoyl)-methylamino]-3-nitro-benzoate

A mixture of 13.1 g of methyl 4-methylamino-3-nitro-benzoate, 10.3 g of 4-cyano-benzoylchloride and 75 ml of phosphorusoxychloride is stirred for 8 hours at 100° C. After cooling, the mixture is decomposed with water and the aqueous phase is extracted with ethyl acetate. The ethyl acetate phases are washed with soda solution and concentrated by evaporation. The residue is dissolved in a little acetone and ether is slowly added. The quantities precipitated initially (about 1.2 g) are discarded. After further ether has been added the desired substance is precipitated. Yield: 10.2 g (48% of theory), $R_f$-value: 0.54 (silica gel; ethyl acetate/petroleum ether=7:3)

EXAMPLE VI 5 (6)-Amino-2 -(4 -cyano-phenyl)-benzimidazole 4.8 g of 2-(4-cyano-phenyl)-5(6)-nitro-benzimidazole are dissolved in a mixture of 150 ml of ethanol and 20 ml of dimethylformamide, 1 g of 5% palladium/charcoal is added and the mixture is treated with hydrogen at a pressure of 5 bars at ambient temperature. After 4 and 21 hours, 1 g of catalyst is added. After a total of 24 hours the catalyst is filtered off, the filtrate is evaporated down, the residue is taken up in ethyl acetate and extracted with 0.1N hydrochloric acid. The aqueous phases are made alkaline with sodium bicarbonate and extracted with ethyl acetate. The residue remaining after evaporation of the ethyl acetate phases is triturated with water to produce crystals. Yield: 1.6 g (40% of theory), Melting point: 128°-130° C. (sintering from 118° C.)

The following compounds are obtained analogously:
(1) ethyl 3-amino-4-[(4-cyano-phenyl)-oxymethylcarbonylamino]-phenoxy-acetate The solvent used is a 1:3.5 mixture of ethyl acetate and tetrahydrofuran. $R_f$ value: 0.59 (silica gel; methylene chloride/methanol/glacial acetic acid: 50:1:0.1 after developing twice)

(2) 3-amino-4-(3-thiomorpholino-propylamino)-benzoic acid-[N-(2-methoxycarbonyl-ethyl)-amide]-hydrochloride The work is done in methanol with 10% palladium/charcoal. $R_f$ value: 0.67 (silica gel; methylene chloride/methanol/conc. ammonia=9:1:0.1, after developing twice)

(3) 3-amino-4-(3-amino-propylamino)-benzoic acid-[N-(2-methoxycarbonyl-ethyl)-amide]-hydrochloride-hydrogen acetate The work is done in glacial acetic acid with 10% palladium/charcoal. $R_f$ value: 0.23 (silica gel; methylene chloride/methanol/glacial acetic acid= 2:1:0.1, after developing twice)

(4) 3-amino-4-methylamino-benzoic acid-[N-(2-methoxycarbonylethyl)-amide]

The same procedure is used as in (2). $R_f$ value: 0.28 (silica gel; ethyl acetate/ethanol=50:2)

(5) 3-amino-4-[2-(3,4-dimethoxy-phenyl)-ethylamino]-benzoic acid-[N-(2-methoxycarbonyl-ethyl)-amide]

The same procedure is used as in (2). $R_f$ value: 0.53 (silica gel; ethyl acetate/ethanol=50:2)

(6) 3-amino-4-(3-pyridylmethylamino)-benzoic acid-[N-(2-methoxycarbonyl-ethyl)-amide]

The same procedure is used as in (2). $R_f$ value: 0.07 (silica gel; ethyl acetate/ethanol=9:1)

(7) 3-amino-4-n-tetradecylamino-benzoic acid-[N-(2-methoxycarbonyl-ethyl)-amide]

The same procedure is used as in (2). $R_f$ value: 0.55 (silica gel; ethyl acetate/ethanol=50:2)

(8) 3-amino-4-(3-methoxycarbonyl-propylamino)-benzoic acid-[N-(2-methoxycarbonyl-ethyl)-amide]-hydrochloride The same procedure is used as in (2) with the addition of ethereal hydrochloric acid. $R_f$ value: 0.65 (silica gel; methylene chloride/Methanol=9:1)

(9) 3-amino-4-(4-phenyl-butylamino)-benzoic acid-[N-(2-methoxycarbonyl-ethyl)-amide]

The same procedure is used as in (2). $R_f$ value: 0.68 (silica gel; ethyl acetate/ethanol=9:1)

(10) 5-amino-2,4-bis-methylamino-benzoic acid-[N-(2-methoxycarbonyl-ethyl)-amide]-hydrochloride The work is done in tetrahydrofuran with 10% palladium/charcoal.

Melting point: 138°-140° C. (decomp.) $R_f$ value: 0.40 (silica gel; methylene chloride/methanol/conc. ammonia=19:1:0.1, after developing twice)

(11) 3-amino-4-[(3,3-diphenyl-propyl)-amino]-benzoic acid-[N-(2-methoxycarbonyl-ethyl)-amide]

The same procedure is used as in (2). $R_f$ value: 0.69 (silica gel; ethyl acetate/ethanol=9:1)

(12) 5-amino-6-methylamino-nicotinic acid-[N-(2-methoxycarbonyl-ethyl)-amide]

The same procedure is used as in (2). $R_f$ value: 0.77 (Reversed-Phase-Plate RP18; methanol/5% sodium chloride solution=6:4)

(13) 3-amino-4-methylamino-benzoic acid-(2-methoxycarbonyl-pyrrolidide)

The same procedure is used as in (2). $R_f$ value: 0.41 (silica gel; ethyl acetate/ethanol=9:1)

(14) 3-amino-4-methylamino-benzoic acid-(3-methoxycarbonyl-piperidide)

The same procedure is used as in (2). $R_f$ value: 0.48 (silica gel; ethyl acetate/ethanol=7:3)

EXAMPLE VII 2-(4-Cyano-phenyl)-5(6)-nitro-benzimidazole 21.9 g of 3,4-diamino-nitrobenzene are added in batches to 400 ml of phosphorusoxychloride, with stirring, at ambient temperature. Then 23.7 g of 4-cyanobenzoylchloride are added. The mixture is first heated to 90° C. for 30 minutes and then to 100° C. for 6 hours. The majority of the excess phosphorusoxychloride is evaporated off in vacuo, the residue is treated with water and the precipitate formed is taken up in ethyl acetate/water. The mixture is made alkaline with sodium bicarbonate and the organic phase is finally evaporated down. Yield: 4.8 g (13% of theory), Melting point: above 200° C. $R_f$ value: 0.74 (silica gel; ethyl acetate/ethanol=50:2)

EXAMPLE VIII

Ethyl 4-amino-3-nitro-phenoxy-acetate 25 g of 4-amino-3-nitro-phenol are dissolved in 250 ml of dimethylformamide and 18.5 g of potassium tert-.butoxide are added in batches whilst cooling with ice. The mixture is stirred for a further 1.5 hours, then 18.5 ml of ethylbromoacetate are added dropwise, whilst cooling with water, and the mixture is stirred for a further 16 hours at ambient temperature. The solvent is evaporated off in vacuo and the residue is taken up with a mixture of 500 ml of ethyl acetate, 250 ml of tetrahydrofuran and 750 ml of water and the organic phase is washed with saturated saline solution. The aqueous phases are extracted with ethyl acetate, the organic phases are combined and evaporated down and the residue is purified by column chromatography (neutral aluminium oxide; eluant:methylene chloride). Yield: 29 g (75% of theory), Melting point: 110°-113° C.

EXAMPLE IX

3-Amino-4-[2-(4-benzyl-piperazino)-ethylamino]-benzoic acid-[N-(2-methoxycarbonyl-ethyl)-amide]

6.3 g of 4-[2-(4-benzyl-piperazino)-ethylamino]-3-nitro-benzoic acid-[N-(2-methoxycarbonyl-ethyl)-amide]-dihydrochloride are dissolved in a mixture of 100 ml of glacial acetic acid and 25 ml of water over a vapour bath and within 10 minutes 4 g of iron powder are added. The mixture is heated for a further 30 minutes, filtered over charcoal and the filtrate is evaporated down. The residue is taken up in 100 ml of tetrahydrofuran and run through a silica gel column, with secondary elution with tetrahydrofuran. The fractions containing the product are evaporated to dryness and triturated with water. The crystalline residue is filtered off and washed with water, methanol and ether. The product is processed further without any additional purification. Yield: 1.2 g (20% of theory), Melting point: 132°-134 C. (decomp.) $R_f$ value: 0.63 (silica gel; methylene chloride/methanol=8:2)

EXAMPLE X

4-[2-(4-Benzyl-piperazino)-ethylamino]-3-nitro-benzoic acid-[N-(2-methoxycarbonyl-ethyl)-amide]-dihydrochloride 9.2 g of 4-[2-(4-benzyl-piperazino)-ethylamino]-3-nitro-benzoic acid-[N-(2-carboxy-ethyl)-amide] are suspended in 1.5 l of methanol with heating, cooled to −20° C., mixed with 1.7 ml of thionylchloride, kept at −10° C. for 2 hours and then stirred for 16 hours at ambient temperature. The mixture is evaporated down to 150 ml in vacuo, the crystals are filtered off and washed with methanol and ether. Yield: 6.5 g (64% of theory), Melting point: 225°-227° C. (decomp.) $R_f$ value: 0.43 (silica gel; methylene chloride/methanol/conc. ammonia=9:1:0.1)

The following compounds are obtained analogously:
(1) 3-nitro-4-(3-thiomorpholino-propylamino)-benzoic acid-[N-(2-methoxycarbonyl-ethyl)-amide]-hydrochloride The work is done in methanol with the addition of ethereal hydrochloric acid at ambient temperature. $R_f$ value: 0.59 (silica gel; methylene chloride/methanol/conc. ammonia=19:1:0.1, after developing twice)
(2) 4-(3-amino-propylamino)-3-nitro-benzoic acid-[N-(2-methoxycarbonyl-ethyl)-amide]-hydrochloride The same procedure is used as in (1).

Melting point: 178°-180° C. (decomp.) $R_f$ value: 0.41 (silica gel; n-butanol/glacial acetic acid/water=4:1:1)
(3) 4-methylamino-3-nitro-benzoic acid-[N-(2-methoxycarbonyl-ethyl)-amide]

The same procedure is used as in (1).

Melting point: 125°-127° C. $R_f$ value: 0.35 (silica gel; ethyl acetate/ethanol=50:1)
(4) 4-[2-(3,4-dimethoxy-phenyl)-ethylamino]-3-nitro-benzoic acid-[N-(2-methoxycarbonyl-ethyl)-amide]

The same procedure is used as in (1).

Melting point: 112°-115° C. $R_f$ value: 0.71 (silica gel; ethyl acetate/ethanol=50:2)
(5) 3-nitro-4-(3-pyridylmethylamino)-benzoic acid-[N-(2-methoxycarbonyl-ethyl)-amide]

The same procedure is used as in (1). $R_f$ value: 0.59 (Reversed Phase Plate RP 18; methanol/5% sodium chloride solution=6:4)
(6) 3-nitro-4-n-tetradecylamino-benzoic acid-[N-(2-methoxycarbonyl-ethyl)-amide]

The same procedure is used as in (1). $R_f$ value: 0.78 (silica gel; ethyl acetate/ethanol=50:2)
(7) 4-(3-methoxycarbonyl-propylamino)-3-nitro-benzoic acid-[N-(2-methoxycarbonyl-ethyl)-amide]

The same procedure is used as in (1). $R_f$ value: 0.80 (silica gel; methylene chloride/methanol=9:1)
(8) 3-amino-2-benzylamino-benzoic acid-[N-(2-methoxycarbonyl-ethyl)-amide]

The same procedure is used as in (1). $R_f$ value: 0.69 (silica gel; methylene chloride/methanol=9:1)
(9) 3-nitro-4-(4-phenyl-butylamino)-benzoic acid-[N-(2-methoxycarbonyl-ethyl)-amide]

The same procedure is used as in (1). $R_f$ value: 0.84 (silica gel; ethyl acetate/ethanol=9:1)
(10) 2,4-bis-methylamino-5-nitro-benzoic acid-[N-(2-methoxycarbonyl-ethyl)-amide]-hydrochloride The same procedure is used as in (1). $R_f$ value: 0.51 (silica gel; methylene chloride/methanol=19:1)
(11) 3-amino-4-[2-(4-amino-3,5-dibromo-phenyl)-ethylamino]-benzoic acid-[N-(2-methoxycarbonyl-ethyl)-amide]-hydrochloride The same procedure is used as in (1).

Melting point: 135°-140° C. (decomp.) $R_f$ value: 0.73 (silica gel; ethyl acetate/ethanol=8:2)
(12) 4-[(3,3-diphenyl-propyl)-amino]-3-nitro-benzoic acid-[N-(2-methoxycarbonyl-ethyl)-amide]

The same procedure is used as in (1). $R_f$ value: 0.86 (silica gel; ethyl acetate/ethanol=9:1)
(13) 6-methylamino-5-nitro-nicotinic acid-[N-2-methoxycarbony-ethyl)-amide]

The same procedure is used as in (1). $R_f$ value: 0.30 (Reversed-Phase-Plate RP18; methanol/5% sodium chloride solution=6:4)
(14) 4-methylamino-3-nitro-benzoic acid-(2-methoxycarbonyl-pyrrolidide)

The same procedure is used as in (1). $R_f$ value: 0.57 (silica gel; ethyl acetate/ethanol=9:1)
(15) 4-methylamino-3-nitro-benzoic acid-(3-methoxycarbonyl-piperidide)

The same procedure is used as in (1). $R_f$ value: 0.67 (silica gel; ethyl acetate/ethanol=9:1)

EXAMPLE XI

4-[2-(4-Benzyl-piperazino)-ethylamino ]-3-nitro-benzoic acid-[N-(2-carboxy-ethyl)-amide]

8.2 g of 4-chloro-3-nitro-benzoic acid-[N-(2-carboxy-ethyl)-amide](prepared from 4-chloro-3-nitro-benzoyl-chloride and β-alanine-methylester and subsequent saponification with 48% hydrobromic acid), 6.6 g of 2-(4-benzyl-piperazino)-ethylamine (prepared from 1-benzyl-piperazine and 2-bromo-ethylamine-hydrobromide in ethanol with the addition of potassium tert.butoxide), 4.2 ml of triethylamine and 25 ml of water are heated over a steam bath for 8 hours. The mixture is evaporated down and purified by column chromatography (silica gel; methylene chloride/methanol/glacial acetic acid=8:2:0.1 to 2:1:0.1). Yield: 9.2 g (67% of theory), $R_f$ value: 0.47 (silica gel; methylene chloride/methanol/conc. ammonia=8:2:0.1)

The following compounds are obtained analogously:
(1) 3-nitro-4-(3-thiomorpholino-propylamino)-benzoic acid-[N-(2-carboxy-ethyl)-amide]

Melting point: 207°-211° C. (decomp.) $R_f$ value: 0.33 (silica gel; methylene chloride/methanol/conc. ammonia=8:2:0.1, after developing four times)
(2) 4-(3-amino-propylamino)-3-nitro-benzoic acid-[N-(2-carboxy-ethyl)-amide]

The work is done without an auxiliary base but with twice the molar amount of 1,3-diaminopropane Melting point: 136° C. (decomp., sintering from 118° C.) $R_f$ value: 0.35 (silica gel; isopropanol/water/conc. ammonia=7:2:1)

(3) 4-methylamino-3-nitro-benzoic acid-[N-(2-carboxy-ethyl)-amide]

The work is done with 40% methylamine solution as solvent and the mixture is heated to 50° C. for 8 hours in a bomb.

Melting point: 187°–190° C. $R_f$ value: 0.22 (silica gel; ethyl acetate/ethanol=50:1)

(4) 4-[2-(3,4-dimethoxy-phenyl)-ethylamino]-3-nitro-benzoic acid-[N-(2-carboxy-ethyl)-amide]-hydrochloride The work is done without a solvent or auxiliary base at a bath temperature of 90° C.

Melting point: 105°–107° C. $R_f$ value: 0.35 (silica gel; ethyl acetate/ethanol/glacial acetic acid=9:1:0.01)

(5) 3-nitro-4-(3-pyridylmethylamino)-benzoic acid-[N-(2-carboxy-ethyl)-amide]

The work is done without an auxiliary base with three times the amount of 3-picolylamine.

Melting point: 110° C. (sintering from 95° C.) $R_f$ value: 0.64 (Reversed Phase Plate RP18; methanol/5% sodium chloride solution=6:4)

(6) 3-nitro-4-n-tetradecylamino-benzoic acid-[N-(2-carboxy-ethyl)-amide]

The work is done without a solvent. $R_f$ value: 0.59 (silica gel; ethyl acetate/ethanol/glacial acetic acid=9:1:0.02)

(7) 4-(3-carboxy-propylamino)-3-nitro-benzoic acid-[N-(2-carboxy-ethyl)-amide]

The work is done in water with the addition of potassium hydrogen carbonate. $R_f$ value: 0.42 (silica gel; methylene chloride/methanol=9:1)

(8) 4-benzylamino-3-nitro-benzoic acid-[N-(2-carboxy-ethyl)-amide]

The work is done without a solvent. $R_f$ value: 0.76 (silica gel; methylene chloride/methanol=9:1)

(9) 3-nitro-4-(4-phenyl-butylamino)-benzoic acid-[N-(2-carboxy-ethyl)-amide]

The work is done without a solvent with N-ethyldiisopropylamine as auxiliary base. $R_f$ value: 0.42 (silica gel; ethyl acetate/ethanol/glacial acetic acid=9:1:0.02)

(10) 2,4-bis-methylamino-5-nitro-benzoic acid-[N-(2-carboxy-ethyl)-amide]-methylamine salt The work is done as in (3) with the reaction lasting 12 hours, using 4-chloro-2-methoxy-5-nitro-benzoic acid-[N-(2-carboxy-ethyl)-amide] as starting material.

Melting point: 180°–189° C. (decomp.) $R_f$ value: 0.62 (silica gel; methylene chloride/methanol/glacial acetic acid=19:1:0.1)

(11) 4-[2-(4-amino-3,5-dibromo-phenyl)-ethylamino]-3-nitro-benzoic acid-[N-(2-carboxy-ethyl)-amide]

The same procedure is used as in (7).

Melting point: 110°–115° C. $R_f$ value: 0.65 (silica gel; ethyl acetate/ethanol/glacial acetic acid=7:3:0.02)

(12) 4-[(3,3-diphenyl-propyl)-amino]-3-nitro-benzoic acid-[N-(2-carboxy-ethyl)-amide]

The same procedure is used as in (9).

Melting point: 185° C. (sintering from 165° C.) $R_f$ value: 0.59 (silica gel; ethyl acetate/ethanol/glacial acetic acid=9:1:0.02)

(13) 4-methylamino-3-nitro-benzoic acid-(2-carboxy-pyrrolidide)

The same procedure is used as in (3). $R_f$ value: 0.12 (silica gel; ethyl acetate/ethanol=9:1)

(14) 4-methylamino-3-nitro-benzoic acid-(3-carboxy-piperidide)

The same procedure is used as in (3). $R_f$ value: 0.33 (silica gel; ethyl acetate/ethanol=9:1)

EXAMPLE XII

3-Amino-4-benzylamino-benzoic acid-[N-(2-carboxy-ethyl)-amide]

4.0 g of 4-benzylamino-3-nitro-benzoic acid-[N-(2-carboxy-ethyl)-amide] are dissolved hot in 40 ml of 5% sodium hydroxide solution and 5.0 g of sodium dithionite are added in batches. After the solution has decolorised it is stirred for a further 15 minutes, allowed to cool and the precipitate formed is filtered off. The filtrate is made weakly acidic with 2N hydrochloric acid, whereupon the product is precipitated. It is suction filtered and washed with water. Yield: 1.6 g (52% of theory), $R_f$ value: 0.26 (silica gel; methylene chloride/methanol=9:1)

The following compound is obtained analogously:

(1) 3-amino-4-[2-(4-amino-3,5-dibromo-phenyl)-ethylamino]-benzoic acid-[N-(2-carboxy-ethyl)-amide]-hydrochloride Melting point: 150°–155° C. $R_f$ value: 0.22 (silica gel; ethyl acetate/ethanol=8:2)

EXAMPLE XIII

4-Chloro-2-methoxy-5-nitro-benzoic acid-[N-(2-carboxy-ethyl)-amide]

The same procedure is used as in Example 17.

Melting point: 170°–172° C. $R_f$ value: 0.38 (silica gel; methylene chloride/methanol/glacial acetic acid=30:1:0.1, after developing twice)

EXAMPLE 1

2-(4-Amidino-phenyl)-5-[(3-carboxy-propyl)-aminocarbonyl]-1-methyl-benzimidazole A mixture of 2.0 g of 2-(4-amidino-phenyl)-5-[(3-methoxy-carbonyl-propyl)-aminocarbonyl]-1-methyl-benzimidazole, 20 ml of methanol and 15.8 ml of 1N sodium hydroxide solution is stirred for 16 hours at ambient temperature. It is evaporated down in vacuo, taken up with water and neutralised by the addition of ammonium chloride. The precipitate formed is filtered off. Yield: 1.3 g (68% of theory), Melting point: above 215° C. $R_f$ value: 0.75 (Reversed-Phase-Plate RP18; methanol/5% aqueous sodium chloride solution=6:4)

The following compounds are obtained analogously:

(1) 2-(4-amidino-phenyl)-5(6)-[(2-carboxy-ethyl)-carbonyl-amino]-benzimidazole

Melting point: above 200° C. $R_f$ value: 0.63 (Reversed-Phase-Plate RP18; methanol/5% aqueous sodium chloride solution=6:4)

| | C | H | N |
|---|---|---|---|
| Calc. × 3 H₂O: | 53.46 | 5.73 | 17.31 |
| Found: | 53.67 | 5.54 | 17.29 |

(2) 2-(4-amidino-phenyl)-5(6)-[(2-carboxy-ethyl)-aminocarbonyl]-benzimidazole-hydrochloride Lithium hydroxide is used $R_f$ value: 0.26 (silica gel; methylene chloride/methanol=7:3)

(3) 2-(4-amidino-phenyl)-5-[(2-carboxy-ethyl)-aminocarbonyl]-1-methyl-benzimidazole Melting point: 247°–249° C. $R_f$ value: 0.70 (Reversed-Phase-Plate RP18; methanol/5% aqueous sodium chloride solution=6:4)

(4) 2-(4-amidino-phenyl)-5 (6)-[(3-carboxy-propyl)-carbonyl-amino]-benzimidazole (5) 2-(4-aminomethyl-phenyl)-5-[(3-carboxy-propyl)-aminocarbonyl]-1-methyl-benzimidazole
(6) 2-(4-aminomethyl-phenyl)-5(6)-[(2-carboxy-ethyl)-amino-carbonyl]-benzimidazole
(7) 2-(4-aminomethyl-phenyl)-5-[(2-carboxy-ethyl)-amino-carbonyl]-1-methyl-benzimidazole
(8) 2-(4-amidino-phenyl)-6-[(2-carboxy-ethyl)-aminocarbonyl]-1-methyl-benzimidazole
(9) 2-(4-amidino-phenyl)-5-[(3-carboxy-propyl)-carbonyl]-1-methyl-benzimidazole
(10) 2-(4-amidino-phenyl)-5-[(4-carboxy-butyl)-carbonyl]-1-methyl-benzimidazole
(11) 2-[4-(2-amino-ethyl)-phenyl]-5-[(3-carboxy-propyl)-carbonyl]-1-methyl-benzimidazole
(12) 2-(4-guanidinomethyl-phenyl)-5-[(2-carboxy-ethyl)-carbonyl]-1-methyl-benzimidazole
(13) 5-[(3-carboxy-propyl)-aminocarbonyl]-2-(3-guanidino-phenyl)-1-methyl-benzimidazole
(14) 2-[4-(2-amino-ethyl)-phenyl]-5-[(2-carboxy-ethyl)-carbonyl]-1-methyl-benzimidazole
(15) 2-(4-amidino-phenyl)-5 (6)-[(2-carboxy-ethyl)-thio]-benzimidazole
(16) 2-(4-amidino-phenyl)-5 (6)-[(2-carboxy-ethyl)-sulphinyl]-benzimidazole
(17) 2-(4-amidino-phenyl)-5 (6)-[(2-carboxy-ethyl)-sulphonyl]-benzimidazole
(18) 2-(4-amidino-phenyl)-5 (6)-[(3-carboxy-propyl)-thio]-benzimidazole
(19) 2-(4-amidino-phenyl)-5 (6)-[(3-carboxy-propyl)-sulphinyl]-benzimidazole
(20) 2-(4-amidino-phenyl)-5 (6)-[(3-carboxy-propyl)-sulphonyl ]-benzimidazole
(21) 2-(4-amidino-phenyl)-5 (6)-[(3-carboxy-propyl)-amino]-benzimidazole
(22) 5(6)-[N-acetyl-N-(3-carboxy-propyl)-amino]-2-(4-amidino-phenyl)-benzimidazole
(23) 2-(4-amidino-phenyl)-5 (6)-[(3-carboxy-propyl)-oxy]-benzimidazole
(24) 2-(4-amidino-phenyl)-5 (6)-(4-carboxy-butyl)-benzimidazole
(25) 2-(4-amidino-phenyl)-5 (6)-[(2-carboxy-ethyl)-aminomethyl]-benzimidazole
(26) 2-(4-amidino-phenyl)-5(6)-[(2-carboxy-ethyl)-thiomethyl]-benzimidazole
(27) 2-(4-amidino-phenyl)-5(6)-[(2-carboxy-ethyl)-sulphinyl-methyl]-benzimidazole
(28) 2-(4-amidino-phenyl)-5(6)-[(2-carboxy-ethyl)-sulphonyl-methyl]-benzimidazole
(29) 5(6)-[N-acetyl-N-(2-carboxy-ethyl)-aminomethyl]-2-(4-amidino-phenyl)-benzimidazole
(30) 2-(4-amidino-phenyl)-5(6)-(carboxymethylcarbonyl-amino-methyl)-benzimidazole
(31) 2-(4-amidino-phenyl)-5(6)-(4-carboxy-1-buten-1-yl)-benzimidazole
(32) 2-(4-amidino-phenyl)-6-[(2-carboxy-ethyl)-aminocarbonyl]-3-methyl-imidazo[4,5-b]pyridine R$_f$ value: 0.74 (Reversed-Phase-Plate RP18; methanol/5% aqueous sodium chloride solution=6:4)
(33) 2-(4-amidino-phenyl)-6-[(2-carboxy-ethyl)-aminocarbonyl]-imidazo [4,5-b]pyridine
(34) 2-(4-amidino-phenyl)-6-[(2-carboxy-ethyl)-aminocarbonyl]-imidazo [1,2-a]pyridine
(35) 2-(4-amidino-phenyl)-6-[(2-carboxy-ethyl)-aminocarbonyl]-3-methyl-imidazo [4,5-c]pyridine
(36) 2-(4-aminomethyl-phenyl)-6-[(2-carboxy-ethyl)-aminocarbonyl]-3-methyl-imidazo [4,5-b]pyridine
(37) 2-(4-amidino-phenyl)-6-[(2-carboxy-ethyl)-aminocarbonyl]-imidazo [4,5-c]pyridazine
(38) 2-(4-amidino-phenyl)-5-[(2-carboxy-ethyl)-aminocarbonyl]-imidazo [4,5-b]pyrazine
(39) 8-(4-amidino-phenyl)-2-[(2-carboxy-ethyl)-aminocarbonyl]-9-methyl-purine
(40) 8-(4-amidino-phenyl)-2-[(2-carboxy-ethyl)-aminocarbonyl]-6-chlor-9-methyl-purine
(41) 8-(4-amidino-phenyl)-2-[(2-carboxy-ethyl)-aminocarbonyl]-6-methoxy-9-methyl-purine
(42) 8-(4-amidino-phenyl)-2-[(2-carboxy-ethyl)-aminocarbonyl]-6-dimethylamino-9-methyl-purine
(43) 8-(4-amidino-phenyl)-6-amino-2-[(2-carboxy-ethyl)-aminocarbonyl]-9-methyl-purine
(44) 8-(4-amidino-phenyl)-2-[(2-carboxy-ethyl)-aminocarbonyl]-9-methyl-6-piperidino-purine
(45) 8-(4-amidino-phenyl)-2-[(2-carboxy-ethyl)-aminocarbonyl]-9-methyl-hypoxanthine
(46) 2-(4-amidino-phenyl)-6-[(2-carboxy-ethyl)-aminocarbonyl]-imidazo [1,2-a]pyrimidine
(47) 2-(4-amidino-phenyl)-5-[N-(2-carboxy-ethyl)-methyl-aminocarbonyl]-1-methyl-benzimidazole
(48) 2-(4-amidino-phenyl)-5-[(2-carboxy-ethyl)-aminocarbonyl]-7-fluoro-1-methyl-benzimidazole
(49) 2-(4-amidino-phenyl)-6-[(2-carboxy-ethyl)-aminocarbonyl]-4-chloro-benzimidazole
(50) 2-(4-amidino-phenyl)-4-brom-6-[(2-carboxy-ethyl)-aminocarbonyl]-benzimidazole
(51) 2-(4-amidino-phenyl)-5-[(2-carboxy-ethyl)-aminocarbonyl]-6-hydroxy-1-methyl-benzimidazole
(52) 2-(4-amidino-phenyl)-5-[(2-carboxy-ethyl)-aminocarbonyl]-6-methoxy-1-methyl-benzimidazole
(53) 2-(4-amidino-phenyl)-5-[(2-carboxy-ethyl)-aminocarbonyl]-1-methyl-6-propyloxy-benzimidazole
(54) 2-(4-amidino-phenyl)-6-[(2-carboxy-ethyl)-aminocarbonyl]-4-methyl-benzimidazole
(55) 2-(4-amidino-phenyl)-5-[(2-carboxy-ethyl)-aminocarbonyl]-1-methyl -6-methanesulphonylamino-benzimidazole
(56) 6-acetylamino-2-(4-amidino-phenyl)-5-[(2-carboxy-ethyl)-aminocarbonyl]-1-methyl-benzimidazole
(57) 2-(4-amidino-phenyl)-5-[(2-carboxy-ethyl)-aminocarbonyl]-6-dimethylamino-1-methyl -benzimidazole
(58) 2-(4-amidino-phenyl)-1-n-butyl-5-[(2-carboxy-ethyl)-aminocarbonyl]-benzimidazole
(59) 2-(4-amidino-phenyl)-5-[(2-carboxy-ethyl)-aminocarbonyl]-1-n-decyl -benzimidazole
(60) 2-(4-amidino-phenyl)-5-[(2-carboxy-ethyl)-aminocarbonyl]-1-cyclopropyl-benzimidazole
(61) 2-(4-amidino-phenyl)-5-[(2-carboxy-ethyl)-aminocarbonyl]-1-cyclohexyl-benzimidazole
(62) 2-(4-amidino-phenyl)-1-benzyl-5-[(2-carboxy-ethyl)-aminocarbonyl]-benzimidazole-hydrochloride
R$_f$ value: 0.25 (silica gel; methylene chloride/methanol=8:2)
(63) 2-(4-amidino-phenyl)-5-[(2-carboxy-ethyl)-aminocarbonyl]-1-(3-phenyl-propyl)-benzimidazole
(64) 2-(4-amidino-phenyl)-5-[(2-carboxy-ethyl)-aminocarbonyl]-1-[2-(3,4-dimethoxy-phenyl)-ethyl]-benzimidazole
(65) 2-(4-amidino-phenyl)-5-[(2-carboxy-ethyl)-aminocarbonyl]-1-[2-(2-pyridyl)-ethyl]-benzimidazole
(66) 2-(4-amidino-phenyl)-5-[(2-carboxy-ethyl)-aminocarbonyl]-1-(3-pyridyl-methyl)-benzimidazole
(67) 2-(4-amidino-phenyl)-5-[(2-carboxy-ethyl)-aminocarbonyl]-1-(4-pyridyl-methyl)-benzimidazole
(68) 2-(4-amidino-phenyl)-5-[(2-carboxy-ethyl)-aminocarbonyl]-1-[3-(1-imidazolyl)-propyl]-benzimidazole

(69) 2-(4-amidino-phenyl)-5-[(2-carboxy-ethyl)-aminocarbonyl]-1-[2-(4-imidazolyl)-ethyl]-benzimidazole
(70) 2-(4-amidino-phenyl)-5-[(2-carboxy-ethyl)-aminocarbonyl]-1-(2-piperazino-ethyl)-benzimidazole
(71) 2-(4-amidino-phenyl)-5-[(2-carboxy-ethyl)-aminocarbonyl]-1-(2-piperidino-ethyl)-benzimidazole
(72) 2-(4-amidino-phenyl)-5-[(2-carboxy-ethyl)-aminocarbonyl]-1-(3-morpholino-propyl)-benzimidazole
(73) 2-(4-amidino-phenyl)-5-[(2-carboxy-ethyl)-aminocarbonyl]-1-(3-thiomorpholino-propyl)-benzimidazole Lithium hydroxide in tetrahydrofuran/water is used. $R_f$ value: 0.06 (silica gel; methylene chloride/methanol/conc. ammonia=2:1:0.1 after developing twice)
(74) 2-(4-amidino-phenyl)-5-[(2-carboxy-ethyl)-aminocarbonyl]-1-[3-(S-oxido-thiomorpholino)-propyl]-benzimidazole Lithium hydroxide in tetrahydrofuran/water is used. $R_f$ value: 0.28 (silica gel; n-butanol/glacial acetic acid/water=4:1:2 after developing three times)
(75) 2-(4-amidino-phenyl)-5-[(2-carboxy-ethyl)-aminocarbonyl]-1-[3-(S,S-dioxido-thiomorpholino)-propyl]-benzimidazole Lithium hydroxide in tetrahydrofuran/water is used. $R_f$ value: 0.14 (silica gel; isopropanol/water/conc. ammonia=7:2:1 after developing twice)
(76) 2-(4-amidino-phenyl)-1-(3-amino-propyl)-5-[(2-carboxy-ethyl)-aminocarbonyl]-benzimidazole-diacetate Lithium hydroxide in tetrahydrofuran/water is used. Melting point: from 110° C. (decomp.) $R_f$ value: 0.13 (silica gel; isopropanol/water/conc. ammonia=7:2:1)
(77) 2-(4-amidino-phenyl)-5-[(2-carboxy-ethyl)-aminocarbonyl]-1-(2-hydroxy-ethyl)-benzimidazole
(78) 2-(4-amidino-phenyl)-5-[(2-carboxy-ethyl)-aminocarbonyl]-1-(2-methoxy-ethyl)-benzimidazole
(79) 2-(4-amidino-phenyl)-5-[(2-carboxy-ethyl)-aminocarbonyl]-1-methyl-benzimidazole-3-oxide Melting point: 263°-265° C. (decomp.) $R_f$ value: 0.79 (Reversed Phase Plate RP18; methanol/5% sodium chloride solution=6:4)
(80) 1-allyl-2-(4-amidino-phenyl)-5-[(2-carboxy-ethyl)-amino-carbonyl]-benzimidazole
(81) 2-(4-amidino-phenyl)-5-[(2-carboxy-ethyl)-aminocarbonyl]-1-phenyl-benzimidazole
(82) 2-(4-amidino-phenyl)-5-[(2-carboxy-ethyl)-aminocarbonyl]-1-(4-chloro-phenyl)-benzimidazole
(83) 2-(4-amidino-phenyl)-5-[(2-carboxy-ethyl)-aminocarbonyl]-1-(4-methoxy-phenyl)-benzimidazole
(84) 2-(4-amidino-phenyl)-5-[(2-carboxy-ethyl)-aminocarbonyl]-1-(3-methyl-phenyl)-benzimidazole
(85) 2-(4-amidino-phenyl)-5-[(2-carboxy-ethyl)-aminocarbonyl]-1-(3-pyridyl)-benzimidazole
(86) 2-(4-amidino-phenyl)-5-[(2-carboxy-ethyl)-aminocarbonyl]-1-(3-methylsulphenyl-phenyl)-benzimidazole
(87) 2-(4-amidino-phenyl)-5-[(2-carboxy-ethyl)-aminocarbonyl]-1-(3-methylsulphinyl-phenyl)-benzimidazole
(88) 2-(4-amidino-phenyl)-5-[(2-carboxy-ethyl)-aminocarbonyl]-1-(3-methylsulphonyl-phenyl)-benzimidazole
(89) 2-(4-amidino-phenyl)-5-[(2-carboxy-ethyl)-aminocarbonyl]-1-carboxymethyl-benzimidazole
(90) 2-(4-amidino-phenyl)-1-(2-carboxy-ethyl)-5-[(2-carboxy-ethyl)-aminocarbonyl]-benzimidazole
(91) 2-(4-amidino-phenyl)-1-(2-aminocarbonyl-ethyl)-5-[(2-carboxy-ethyl)-aminocarbonyl]-benzimidazole
(92) 2-(4-amidino-phenyl)-5-[(2-carboxy-ethyl)-aminocarbonyl]-1-(2-dimethylaminocarbonyl-ethyl)-benzimidazole
(93) 2-(4-amidino-phenyl)-5-[(2-carboxy-ethyl)-aminocarbonyl]-1-(2-morpholinocarbonyl-ethyl)-benzimidazole
(94) 2-(4-amidino-phenyl)-5-[(2-carboxy-ethyl)-aminocarbonyl]-1-(2-thiomorpholinocarbonyl-ethyl)-benzimidazole
(95) 2-(4-amidino-phenyl)-5-[(2-carboxy-ethyl)-aminocarbonyl]-1-[2-(S-oxido-thiomorpholinocarbonyl)-ethyl]-benzimidazole
(96) 2-(4-amidino-phenyl)-5-[(2-carboxy-ethyl)-aminocarbonyl]-1-[2-(S,S-dioxido-thiomorpholinocarbonyl)-ethyl]-benzimidazole
(97) 2-(4-amidino-phenyl)-5-[(2-carboxy-ethyl)-aminocarbonyl]-1-[2-(carboxymethyl-aminocarbonyl)-ethyl]-benzimidazole
(98) 2-(4-aminomethyl-cyclohexyl)-5-[(2-carboxy-ethyl)-aminocarbonyl]-1-methyl-benzimidazole
(99) 2-(1-amidino-4-piperidinyl)-5-[(2-carboxy-ethyl)-aminocarbonyl]-1-methyl-benzimidazole
(100) 2-(5-amidino-2-pyridyl)-5-[(2-carboxy-ethyl)-aminocarbonyl]-1-methyl-benzimidazole
(101) 2-(4-amidino-2-fluoro-phenyl)-5-[(2-carboxy-ethyl)-aminocarbonyl]-1-methyl-benzimidazole
(102) 2-(4-amidino-2-chloro-phenyl)-5(6)-[(2-carboxy-ethyl)-aminocarbonyl]-benzimidazole
(103) 2-(4-amidino-2-methoxy-phenyl)-5-[(2-carboxy-ethyl)-aminocarbonyl]-1-methyl-benzimidazole
(104) 2-(4-amidino-2-methyl-phenyl)-5-[(2-carboxy-ethyl)-aminocarbonyl]-1-methyl-benzimidazole
(105) 2-(4-amidino-phenyl)-5-(4-carboxy-1-piperidinyl)-3-methyl-imidazo[4,5-b]pyridine
(106) 2-(4-amidino-phenyl)-5-(4-carboxymethyl-1-piperidinyl)-3-methyl-imidazo[4,5-b]pyridine
(107) 2-(4-amidino-phenyl)-5-(4-carboxy-cyclohexylmethylamino)-3-methyl-imidazo[4,5-b]pyridine
(108) 2-(4-amidino-phenyl)-5-[(2-carboxy-ethyl)-aminocarbonyl]-benzoxazole
(109) 2-(4-amidino-phenyl)-6-[(2-carboxy-ethyl)-aminocarbonyl]-benzothiazole
(110) 2-(4-amidino-phenyl)-5-[(2-carboxy-ethyl)-aminocarbonyl]-oxazolo[5,4-b]pyridine
(111) 2-(4-amidino-phenyl)-5-(N-carboxymethyl-methylaminocarbonylmethyl)-5H-imidazo[4,5-c]pyridin-4-one
(112) 8-(4-amidino-phenyl)-1-(N-carboxymethyl-methylaminocarbonylmethyl)-hypoxanthine
(113) 8-(4-amidino-phenyl)-1-(N-carboxymethyl-methylaminocarbonylmethyl)-xanthine
(114) 2-(4-amidino-phenyl)-6-[(2-carboxy-ethyl)-aminocarbonyl]-3-methyl-imidazo [1,2-a]pyridine
(115) 2-(4-amidino-phenyl)-5-[(2-carboxy-ethyl)-aminocarbonyl]-1-(2-pyrrolidino-ethyl)-benzimidazole
(116) 2-(4-amidino-phenyl)-5-[(2-carboxy-ethyl)-aminocarbonyl]-1-(3-methylsulphenyl-propyl)-benzimidazole
(117) 2-(4-amidino-phenyl)-5-[(2-carboxy-ethyl)-aminocarbonyl]-1-(3-methylsulphinyl-propyl)-benzimidazole
(118) 2-(4-amidino-phenyl)-5-[(2-carboxy-ethyl)-aminocarbonyl]-1-(3-methylsulphonyl-propyl)-benzimidazole
(119) 2-(4-amidino-1-piperazinyl)-5-[(2-carboxy-ethyl)-aminocarbonyl]-1-methyl-benzimidazole (120) 2-(4-amidino-phenyl)-5-[(2-carboxy-ethyl)-aminocarbonyl]-1-propargyl-benzimidazole
(121) 2-(4-amidino-phenyl)-6-[N-(3-carboxy-propyl)-methanesulphonylamino]-3-methyl-imidazo[4,5-b]pyridine
(122) 2-(4-amidino-phenyl)-5-[(2-carboxy-ethyl)-aminosulphonyl]-1-methyl-benzimidazole
(123) 2-(4-amidino-phenyl)-5-(carboxymethyl-aminosulphonyl)-1-methyl-benzimidazole
(124) 2-(4-amidino-phenyl)-5-[N-[(4-carboxy-cyclohexyl)-methyl]-N-methyl-amino]-3-methyl-imidazo[4,5-b]pyridine
(125) 2-(4-amidino-phenyl)-5-(4-carboxymethyl-1-piperazinyl)-3-methyl-imidazo[4,5-b]pyridine
(126) 2-(4-amidino-phenyl)-5-(4-carboxymethyl-3-oxo-1-piperazinyl)-3-methyl-imidazo[4,5-b]pyridine
(127) 5-[(2-carboxy-ethyl)-aminocarbonyl]-1-methyl-2-(4-methylamidino-phenyl)-benzimidazole
(128) 2-(n-butylamidino-phenyl)-5-[(2-carboxy-ethyl)-aminocarbonyl]-1-methyl-benzimidazole
(129) 5-[(2-carboxy-ethyl)-aminocarbonyl]-1-methyl-2-(4-methylaminomethyl-phenyl)-benzimidazole
(130) 2-(4-amidino-phenyl)-5-[(4-carboxy-cyclohexyl)-amino]-3-methyl-imidazo[4,5-b]pyridine
(131) 2-(4-amidino-phenyl)-5-[N-(2-carboxy-ethyl)-methyl-aminosulphonyl]-1-methyl-benzimidazole
(132) 2-(4-amino-cyclohexyl)-5-[(2-carboxy-ethyl)-aminocarbonyl]-1-methyl-benzimidazole
(133) 8-(4-amidino-phenyl)-1-(N-carboxymethyl-methylaminocarbonylmethyl)-3-methyl-xanthine
(134) 2-(4-amidino-phenyl)-1-(6-amino-hexyl)-5-[(2-carboxy-ethyl)-aminocarbonyl]-benzimidazole
(135) 2-[(4-amidino-phenyl)-oxymethyl]-5(6)-carboxymethoxy-benzimidazole R$_f$ value: 0.07 (silica gel; n-butanol/glacial acetic acid/water=4:1:1, developed twice)

| Calc.: | C | 60.00 | H | 4.74 | N | 16.46 |
|---|---|---|---|---|---|---|
| Found: | | 59.60 | | 4.82 | | 16.52 |

(136) 2-(4-amidino-phenyl)-1-[2-(4-benzyl-piperazino)-ethyl]-5-[(2-carboxy-ethyl)-aminocarbonyl]-benzimidazole Lithium hydroxide in tetrahydrofuran/water is used.
Melting point: 82° C. (decomp.) R$_f$ value: 0.51 (silica gel; isopropanol/water/conc. ammonia=7:2:1)

(137) 2-(4-aminomethyl-phenyl)-5-[(2-carboxy-ethyl)-aminocarbonyl]-1-(3-thiomorpholino-propyl)-benzimidazole Lithium hydroxide in tetrahydrofuran/water is used.
R$_f$ value: 0.50 (Reversed Phase Plate RP18; methanol/5% sodium chloride solution=6:10)

(138) 2-(4-amidino-phenyl)-5-[(2-carboxy-ethyl)-aminocarbonyl]-1-(3-carboxy-propyl)-benzimidazole R$_f$ value: 0.10 (silica gel; methylene chloride/methanol=8:2)

(139) 2-(4-amidino-phenyl)-5-[(2-carboxy-ethyl)-aminocarbonyl]-1-methyl-6-methylamino-benzimidazole Lithium hydroxide is used.
Melting point: 265°-266° C. (decomp.) R$_f$ value: 0.35 (silica gel; n-butanol/glacial acetic acid/water=4:1:2)

(140) 2-(4-amidino-phenyl)-5-[(2-carboxy-ethyl)-aminocarbonyl]-6-(N-carboxymethyl-methylamino)-1-methyl-benzimidazole Lithium hydroxide is used. R$_f$ value: 0.62 (Reversed Phase Plate RP18; methanol/5% sodium chloride solution 6:4, after developing twice)

(141) 2-(4-amidino-phenyl)-5-[(2-carboxy-ethyl)-aminocarbonyl]-1-(3,3-diphenyl-propyl)-benzimidazole
(142) 2-[4-(2-amino-2-propyl)-phenyl]-5-[(2-carboxy-ethyl)-aminocarbonyl]-1-methyl-benzimidazole
(143) 2-(1-amino-5-indanyl)-5-[(2-carboxy-ethyl)-aminocarbonyl]-1-methyl-benzimidazole
(144) 2-(1-amino-1,2,3,4-tetrahydro-6-naphthyl)-5-[(2-carboxy-ethyl)-aminocarbonyl]-1-methyl-benzimidazole
(145) 2-[4-(1-amino-cyclopropyl)-phenyl]-5-[(2-carboxy-ethyl)-aminocarbonyl]-1-methyl-benzimidazole
(146) 2-[4-(1-amino-cyclopentyl)-phenyl]-5-[(2-carboxy-ethyl)-aminocarbonyl]-1-methyl-benzimidazole
(147) 2-(4-amidino-phenyl)-5-[(2-carboxy-2-methyl-propyl)-aminocarbonyl]-1-methyl-benzimidazole
(148) 2-(4-amidino-phenyl)-5-[(2-carboxy-propyl)-aminocarbonyl]-1-methyl-benzimidazole
(149) 2-(4-amidino-phenyl)-5-[(2-carboxy-4-phenyl-butyl)-aminocarbonyl]-1-methyl-benzimidazole
(150) 8-(4-amidino-phenyl)-2-[(2-carboxy-ethyl)-aminocarbonyl]-7-methyl-purine
(151) 8-(4-amidino-phenyl)-2-[(2-carboxy-ethyl)-aminocarbonyl]-6-methoxy-7-methyl-purine
(152) 8-(4-amidino-phenyl)-2-[(2-carboxy-ethyl)-aminocarbonyl]-6-dimethylamino-7-methyl-purine
(153) 8-(4-amidino-phenyl)-6-amino-2-[(2-carboxy-ethyl)-aminocarbonyl]-7-methyl-purine
(154) 8-(4-amidino-phenyl)-2-[(2-carboxy-ethyl)-aminocarbonyl]-7-methyl-6-piperidino-purine
(155) 8-(4-amidino-phenyl)-2-[(2-carboxy-ethyl)-aminocarbonyl]-7-methyl-hypoxanthine
(156) 2-(4-amidino-phenyl)-7-[(2-carboxy-ethyl)-aminocarbonyl]-imidazo[1,2-a]pyridine
(157) 2-(4-amidino-phenyl)-7-[(2-carboxy-ethyl)-aminocarbonyl]-imidazo[1,2-a]pyrimidine
(158) 2-(4-amidino-phenyl)-7-[(2-carboxy-ethyl)-aminocarbonyl]-imidazo[1,2-c]pyrimidine
(159) 2-(4-amidino-phenyl)-5-[(2-carboxy-ethyl)-aminocarbonyl]-benzothiazole
(160) 8-(4-amidino-phenyl)-1-(4-carboxy-butyl)-3,9-dimethyl-xanthine Melting point: 263°-265° C.(decomp.) R$_f$ value: 0.48 (silica gel; n-butanol/glacial acetic acid/water=4:1:1.5)
(161) 2-(4-amidino-phenyl)-7-[(2-carboxy-ethyl)-aminocarbonyl]-3-methyl-imidazo[1,2-a]pyridine
(162) 2-(4-amidino-phenyl)-5-[(2-carboxy-ethyl)-aminocarbonyl]-1-methyl-6-(3-phenyl-propyloxy)-benzimidazole
(163) 2-(4-amidino-phenyl)-5-[(2-carboxy-ethyl)-aminocarbonyl]-1-(4-methyl-benzyl)-benzimidazole
(164) 2-(4-amidino-phenyl)-5-[(2-carboxy-ethyl)-aminocarbonyl]-1-[2-(3,5-dichloro-4-hydroxy-phenyl)-ethyl]-benzimidazole
(165) 2-(4-amidino-phenyl)-5-[(2-carboxy-ethyl)-aminocarbonyl]-1-[(2-phenyl-ethyl)-aminocarbonylmethyl]-benzimidazole

EXAMPLE 2

2-(4-Amidino-phenyl)-5-[(3-methoxycarbonyl-propyl)-aminocarbonyl]-1-methyl-benzimidazole-hydrochloride 4.2 g of methyl 4-[4-[N-(4-amidino-benzoyl)-methylamino]-3-nitro-benzoylamino]-butyrate are dissolved in 100 ml of methanol, mixed with 10 ml of ethereal hydrochloric acid and 0.5 g of 10% palladium/-charcoal and treated at ambient temperature with 5 bars of hydrogen for 22 hours. A further 0.3 g of catalyst are added and the mixture is reacted for a further hour. The catalyst is filtered off, the filtrate is evaporated down and the residue is stirred with a mixture of 100 ml of ethyl acetate and 10 ml of methanol for one hour at ambient temperature, whereupon the substance is obtained in crystalline form. Yield: 3.7 g (100% of theory), Melting point: above 200° C. $R_f$ value: 0.65 (Reversed-Phase-Plate RP18; methanol/5% sodium chloride solution=6:4)

The following compounds are obtained analogously:
(1) 2-(4-amidino-phenyl)-5-[(2-methoxycarbonyl-ethyl)-aminocarbonyl]-1-methyl-benzimidazole $R_f$ value: 0.59 (Reversed-Phase-Plate RP18; methanol/5% sodium chloride solution=6:4)
(2) 2-(4-amidino-phenyl)-5-[(2-ethoxycarbonyl-ethyl)-aminocarbonyl]-1-methyl-benzimidazole
(3) 2-(4-amidino-phenyl)-5-[N-(2-methoxycarbonyl-ethyl)-N-methyl-aminocarbonyl]-1-methyl-benzimidazole
(4) 2-(4-amidino-phenyl)-5-[(2-methoxycarbonyl-ethyl)-aminocarbonyl] -1-methyl-benzimidazol-3-oxide The work is done without the addition of hydrochloric acid $R_f$ value: 0.63 (Reversed-Phase-Plate RP18; methanol/5% sodium chloride solution=6:4)

EXAMPLE 3

2-[(4-Amidino-phenyl)-oxymethyl]-5(6)-methoxycarbonyl-methoxy-benzimidazole-hydrochloride 2.4 g of 2-[(4-cyano-phenyl)-oxymethyl]-5(6)-methoxycarbonylmethoxy-benzimidazole are suspended in 300 ml of methanol. Hydrochloric acid gas is piped into the mixture for one hour at 0°-10° C. and the resulting mixture is stirred for 4 hours at 15°-20° C. The methanol is evaporated off in vacuo, the residue is mixed with 75 ml of methanol and this is in turn distilled off in vacuo. The residue is suspended in 300 ml of methanol, after which 16.3 g of ammonium carbonate are added in batches with stirring and the mixture is stirred for a further 16 hours. The reaction mixture is adjusted to pH 4 with a mixture of three parts methanol and one part concentrated hydrochloric acid. It is evaporated to dryness and the residue is purified over silica gel (eluant:methylene chloride/methanol=3:1 to 0:1). Yield: 0.9 g (32% of theory), Melting point: 250° C. (decomp.) $R_f$ value: 0.64 (silica gel; methylene chloride/methanol/glacial acetic acid=3:1:0.1)

| | | | | | | | | |
|---|---|---|---|---|---|---|---|---|
| Calc. × H$_2$O × HCl: | C | 52.87 | H | 5.18 | N | 13.70 | Cl | 8.67 |
| Found: | | 53.07 | | 5.02 | | 13.81 | | 8.80 |

The following compounds are obtained analogously:
(1) 2-(4-amidino-phenyl)-5(6)-[(2-methoxycarbonyl-ethyl)-carbonylamino]-benzimidazole Melting point above 200° C. $R_f$ value: 0.11 (silica gel; ethyl acetate/ethanol=7:3)
(2) 2-(4-amidino-phenyl)-5 (6)-[(2-methoxycarbonyl-ethyl)-aminocarbonyl]-benzimidazole
(3) 2-(4-amidino-phenyl)-5-[(2-methoxycarbonyl-ethyl)-aminocarbonyl]-1-methyl-benzimidazole
(4) 2-(4-amidino-phenyl)-5-[(2-ethoxycarbonyl-ethyl)-aminocarbonyl]-1-methyl-benzimidazole Ethanolic hydrochloric acid is used.

(5) 2-(4-amidino-phenyl)-5(6)-[(3-methoxycarbonyl-propyl)-carbonylamino]-benzimidazole
(6) 2-(4-amidino-phenyl)-6-[(2-methoxycarbonyl-ethyl)-aminocarbonyl]-1-methyl-benzimidazole
(7) 2-(4-amidino-phenyl)-5-[(3-methoxycarbonyl-propyl)-carbonyl]-1-methyl-benzimidazole
(8) 2-(4-amidino-phenyl)-5-[(4-methoxycarbonyl-butyl)-carbonyl]-1-methyl-benzimidazole
(9) 2-(4-amidino-phenyl)-5 (6)-(2-methoxycarbonyl-ethyl-thio)-benzimidazole
(10) 2-(4-amidino-phenyl)-5 (6)-(3-methoxycarbonyl-propyl-thio)-benzimidazole
(11) 2-(4-amidino-phenyl)-5(6)-[(3-methoxycarbonyl-propyl)-amino]-benzimidazole
(12) 5(6)-[N-acetyl-N-(3-methoxycarbonyl-propyl)-amino]-2-(4-amidino-phenyl)-benzimidazole
(13) 2-(4-amidino-phenyl)-5(6)-[(3-methoxycarbonyl-propyl)-oxy]-benzimidazole
(14) 2-(4-amidino-phenyl)-5 (6)-(4-methoxycarbonyl-butyl)-benzimidazole
(15) 2-(4-amidino-phenyl)-5 (6)-[(2-methoxycarbonyl-ethyl)-aminomethyl]-benzimidazole
(16) 2-(4-amidino-phenyl)-5 (6)-[(2-methoxycarbonyl-ethyl)-thiomethyl]-benzimidazole
(17) 2-(4-amidino-phenyl)-5 (6)-(methoxycarbonyl-methylcarbonyl-aminomethyl)-benzimidazole
(18) 2-(4-amidino-phenyl)-5 (6)-(4-methoxycarbonyl-1-buten-1-yl)-benzimidazole
(19) 2-(4-amidino-phenyl)-6-[(2-methoxycarbonyl-ethyl)-aminocarbonyl]-3-methyl-imidazo[4,5-b]pyridine $R_f$ value: 0.49 (Reversed-Phase-Plate RP18; methanol/5% sodium chloride solution=6:4)
(20) 2-(4-amidino-phenyl)-6-[(2-methoxycarbonyl-ethyl)-aminocarbonyl]-imidazo[4,5-b]pyridine
(21) 2-(4-amidino-phenyl)-6-[(2-methoxycarbonyl-ethyl)-aminocarbonyl]-imidazo[1,2-a]pyridine
(22) 2-(4-amidino-phenyl)-6-[(2-methoxycarbonyl-ethyl)-aminocarbonyl]-3-methyl-imidazo [4,5-c]pyridine
(23) 2-(4-amidino-phenyl)-6-[(2-methoxycarbonyl-ethyl)-aminocarbonyl]-imidazo [4,5-c]pyridazine
(24) 2-(4-amidino-phenyl)-5-[(2-methoxycarbonyl-ethyl)-aminocarbonyl]-imidazo [4,5-b]pyrazine
(25) 8-(4-amidino-phenyl)-2-[(2-methoxycarbonyl-ethyl)-aminocarbonyl]-9-methyl-purine
(26) 8-(4-amidino-phenyl)-6-chloro-2-[(2-methoxycarbonyl-ethyl)-aminocarbonyl]-9-methyl-purine
(27) 8-(4-amidino-phenyl)-6-methoxy-2-[(2-methoxycarbonyl-ethyl)-aminocarbonyl]-9-methyl-purine
(28) 8-(4-amidino-phenyl)-6-dimethylamino-2-[(2-methoxycarbonyl-ethyl)-aminocarbonyl]-9-methyl-purine
(29) 8-(4-amidino-phenyl)-6-amino-2-[(2-methoxycarbonyl-ethyl)-aminocarbonyl]-9-methyl-purine
(30) 8-(4-amidino-phenyl)-2-[(2-methoxycarbonyl-ethyl)-aminocarbonyl]-9-methyl-6-piperidino-purine
(31) 8-(4-amidino-phenyl)-2-[(2-methoxycarbonyl-ethyl)-aminocarbonyl]-9-methyl -hypoxanthine
(32) 2-(4-amidino-phenyl)-6-[(2-methoxycarbonyl-ethyl)-aminocarbonyl]-imidazo[1,2-a]pyrimidine
(33) 2-(4-amidino-phenyl)-5-[N-(2-methoxycarbonyl-ethyl)-methylaminocarbonyl]-1-methyl-benzimidazole
(34) 2-(4-amidino-phenyl)-7-fluor-5-[(2-methoxycarbonyl-ethyl)-aminocarbonyl]-1-methyl -benzimidazole
(35) 2-(4-amidino-phenyl)-4-chloro-6-[(2-methoxycarbonyl-ethyl)-aminocarbonyl]-benzimidazole
(36) 2-(4-amidino-phenyl)-4-bromo-6-[(2-methoxycarbonyl-ethyl)-aminocarbonyl]-benzimidazole

(37) 2-(4-amidino-phenyl)-6-hydroxy-5-[(2-methoxycarbonyl-ethyl)-aminocarbonyl]-1-methyl-benzimidazole

(38) 2-(4-amidino-phenyl)-6-methoxy-5-[(2-methoxycarbonyl-ethyl)-aminocarbonyl]-1-methyl-benzimidazole

(39) 2-(4-amidino-phenyl)-5-[(2-methoxycarbonyl-ethyl)-aminocarbonyl]-1-methyl-6-propyloxy-benzimidazole

(40) 2-(4-amidino-phenyl)-6-[(2-methoxycarbonyl-ethyl)-aminocarbonyl]-4-methyl-benzimidazole

(41) 2-(4-amidino-phenyl)-5-[(2-methoxycarbonyl-ethyl)-aminocarbonyl]-1-methyl-6-methanesulphonylamino-benzimidazole

(42) 6-acetylamino-2-(4-amidino-phenyl)-5-[(2-methoxycarbonyl-ethyl)-aminocarbonyl]-1-methyl-benzimidazole

(43) 2-(4-amidino-phenyl)-6-dimethylamino-5-[(2-methoxycarbonyl-ethyl)-aminocarbonyl]-1-methyl-benzimidazole

(44) 2-(4-amidino-phenyl)-1-n-butyl-5-[(2-methoxycarbonyl-ethyl)-aminocarbonyl]-benzimidazole

(45) 2-(4-amidino-phenyl)-1-n-decyl-5-[(2-methoxycarbonyl-ethyl)-aminocarbonyl]-benzimidazole

(46) 2-(4-amidino-phenyl)-1-cyclopropyl-5-[(2-methoxycarbonyl-ethyl)-aminocarbonyl]-benzimidazole

(47) 2-(4-amidino-phenyl)-1-cyclohexyl-5-[(2-methoxycarbonyl-ethyl)-aminocarbonyl]-benzimidazole

(48) 2-(4-amidino-phenyl)-1-benzyl-5-[(2-methoxycarbonyl-ethyl)-aminocarbonyl]-benzimidazole-hydrochloride $R_f$ value: 0.22 (silica gel; methylene chloride/methanol=7:3)

(49) 2-(4-amidino-phenyl)-5-[(2-methoxycarbonyl-ethyl)-aminocarbonyl]-1-(3-phenyl-propyl)-benzimidazole

(50) 2-(4-amidino-phenyl)-1-[2-(3,4-dimethoxy-phenyl)-ethyl]-5-[(2-methoxycarbonyl-ethyl)-aminocarbonyl]-benzimidazole-hydrochloride $R_f$ value: 0.20 (silica gel; ethyl acetate/ethanol=7:3)

(51) 2-(4-amidino-phenyl)-5-[(2-methoxycarbonyl-ethyl)-aminocarbonyl]-1-[2-(2-pyridyl)-ethyl]-benzimidazole

(52) 2-(4-amidino-phenyl)-5-[(2-methoxycarbonyl-ethyl)-aminocarbonyl]-1-(3-pyridylmethyl)-benzimidazole $R_f$ value: 0.60 (Reversed Phase Plate RP18; methanol/5% sodium chloride solution=6:4)

(53) 2-(4-amidino-phenyl)-5-[(2-methoxycarbonyl-ethyl)-aminocarbonyl]-1-(4-pyridylmethyl)-benzimidazole

(54) 2-(4-amidino-phenyl)-1-[3-(1-imidazolyl)-propyl]-5-[(2-methoxycarbonyl-ethyl)-aminocarbonyl]-benzimidazole

(55) 2-(4-amidino-phenyl)-1-[2-(4-imidazolyl)-ethyl]-5-[(2-methoxycarbonyl-ethyl)-aminocarbonyl]-benzimidazole

(56) 2-(4-amidino-phenyl)-5-[(2-methoxycarbonyl-ethyl)-aminocarbonyl]-1-(2-piperazino-ethyl)-benzimidazole

(57) 2-(4-amidino-phenyl)-5-[(2-methoxycarbonyl-ethyl)-aminocarbonyl]-1-(2-piperidino-ethyl)-benzimidazole

(58) 2-(4-amidino-phenyl)-5-[(2-methoxycarbonyl-ethyl)-aminocarbonyl]-1-(3-morpholino-propyl)-benzimidazole

(59) 2-(4-amidino-phenyl)-5-[(2-methoxycarbonyl-ethyl)-aminocarbonyl]-1-(3-thiomorpholino-propyl)-benzimidazole $R_f$ value: 0.18 (silica gel; methylene chloride/methanol/conc. ammonia=8:2:0.1)

(60) 2-(4-amidino-phenyl)-1-(3-amino-propyl)-5-[(2-methoxycarbonyl-ethyl)-aminocarbonyl]-benzimidazole $R_f$ value: 0.29 (silica gel; n-butanol/glacial acetic acid/water=4:1:1, after developing three times)

(61) 2-(4-amidino-phenyl)-1-(2-hydroxy-ethyl)-5-[(2-methoxycarbonyl-ethyl)-aminocarbonyl]-benzimidazole

(62) 2-(4-amidino-phenyl)-5-[(2-methoxycarbonyl-ethyl)-aminocarbonyl]-1-(2-methoxy-ethyl)-benzimidazole

(63) 1-allyl-2-(4-amidino-phenyl)-5-[(2-methoxycarbonyl-ethyl)-aminocarbonyl]-benzimidazole

(64) 2-(4-amidino-phenyl)-5-[(2-methoxycarbonyl-ethyl)-aminocarbonyl]-1-phenyl-benzimidazole

(65) 2-(4-amidino-phenyl)-1-(4-chloro-phenyl)-5-[(2-methoxycarbonyl-ethyl)-aminocarbonyl]-benzimidazole

(66) 2-(4-amidino-phenyl)-5-[(2-methoxycarbonyl-ethyl)-aminocarbonyl]-1-(4-methoxy-phenyl)-benzimidazole

(67) 2-(4-amidino-phenyl)-5-[(2-methoxycarbonyl-ethyl)-aminocarbonyl]-1-(3-methyl-phenyl)-benzimidazole

(68) 2-(4-amidino-phenyl)-5-[(2-methoxycarbonyl-ethyl)-aminocarbonyl]-1-(3-pyridyl)-benzimidazole

(69) 2-(4-amidino-phenyl)-5-[(2-methoxycarbonyl-ethyl)-aminocarbonyl]-1-(3-methylsulphenyl-phenyl)-benzimidazole

(70) 2-(4-amidino-phenyl)-5-[(2-methoxycarbonyl-ethyl)-aminocarbonyl]-1-methoxycarbonylmethyl-benzimidazole

(71) 2-(4-amidino-phenyl)-1-(2-methoxycarbonyl-ethyl)-5-[(2-methoxycarbonyl-ethyl)-aminocarbonyl]-benzimidazole

(72) 2-(4-amidino-phenyl)-1-(2-aminocarbonyl-ethyl)-5-[(2-methoxycarbonyl-ethyl)-aminocarbonyl]-benzimidazole

(73) 2-(4-amidino-phenyl)-1-(2-dimethylaminocarbonyl-ethyl)-5-[(2-methoxycarbonyl-ethyl)-aminocarbonyl]-benzimidazole

(74) 2-(4-amidino-phenyl)-5-[(2-methoxycarbonyl-ethyl)-aminocarbonyl]-1-(2-morpholinocarbonyl-ethyl)-benzimidazole

(75) 2-(4-amidino-phenyl)-5-[(2-methoxycarbonyl-ethyl)-aminocarbonyl]-1-(2-thiomorpholinocarbonyl-ethyl)-benzimidazole

(76) 2-(4-amidino-phenyl)-5-[(2-methoxycarbonyl-ethyl)-aminocarbonyl]-1-[2-(methoxycarbonylmethyl-aminocarbonyl)-ethyl]-benzimidazole

(77) 2-(5-amidino-2-pyridyl)-5-[(2-methoxycarbonyl-ethyl)-aminocarbonyl]-1-methyl-benzimidazole

(78) 2-(4-amidino-2-fluoro-phenyl)-5-[(2-methoxycarbonyl-ethyl)-aminocarbonyl]-1-methyl-benzimidazole

(79) 2-(4-amidino-2-chloro-phenyl)-5(6)-[(2-methoxycarbonyl-ethyl)-aminocarbonyl]-benzimidazole

(80) 2-(4-amidino-2-methoxy-phenyl)-5-[(2-methoxycarbonyl-ethyl)-aminocarbonyl]-1-methyl-benzimidazole

(81) 2-(4-amidino-2-methyl-phenyl)-5-[(2-methoxycarbonyl-ethyl)-aminocarbonyl]-1-methyl-benzimidazole

(82) 2-(4-amidino-phenyl)-5-(2-methoxycarbonyl-1-piperidinyl)-3-methyl-imidazo[4,5-b]pyridine

(83) 2-(4-amidino-phenyl)-5-(4-methoxycarbonylmethyl-1-piperidinyl)-3-methyl-imidazo[4,5-b]pyridine

(84) 2-(4-amidino-phenyl)-5-(4-methoxycarbonyl-cyclohexyl-methylamino)-3-methyl-imidazo[4,5-b]pyridine

(85) 2-(4-amidino-phenyl)-5-[(4-methoxycarbonyl-ethyl)-aminocarbonyl]-benzoxazole

(86) 2-(4-amidino-phenyl)-6-[(2-methoxycarbonyl-ethyl)-aminocarbonyl]-benzothiazole

(87) 2-(4-amidino-phenyl)-5-[(2-methoxycarbonyl-ethyl)-aminocarbonyl]-oxazolo[5,4-b]pyridine

(88) 2-(4-amidino-phenyl)-5-(N-methoxycarbonylmethyl-methylamino-carbonylmethyl)-5H-imidazo[4,5-c]pyridin-4-one

(89) 8-(4-amidino-phenyl)-1-(N-methoxycarbonylmethyl-methylamino-carbonylmethyl)-hypoxanthine

(90) 8-(4-amidino-phenyl)-1-(N-methoxycarbonylmethyl-methylamino-carbonylmethyl)-xanthine

(91) 2-(4-amidino-phenyl)-6-[(2-methoxycarbonyl-ethyl)-aminocarbonyl]-3-methyl-imidazo[1,2-a]pyridine

(92) 2-(4-amidino-phenyl)-5-[(2-methoxycarbonyl-ethyl)-aminocarbonyl]-1-(2-pyrrolidino-ethyl)-benzimidazole

(93) 2-(4-amidino-phenyl)-1-methyl-5-[[2-(5-tetrazolyl)-ethyl]-aminocarbonyl]-benzimidazole

(94) 2-(4-amidino-phenyl)-1-methyl -5-[(2-phosphono-ethyl)-aminocarbonyl]-benzimidazole

(95) 2-(4-amidino-phenyl)-1-methyl-5-[[2-(O-methyl-phosphono)-ethyl]-aminocarbonyl]-benzimidazole

(96) 2-(4-amidino-phenyl)-1-methyl-5-[(2-sulpho-ethyl)-aminocarbonyl]-benzimidazole

(97) 2-(4-amidino-phenyl)-5-[(2-methoxycarbonyl-ethyl)-aminocarbonyl]-1-(3-methylsulphenyl-propyl)-benzimidazole

(98) 2-(4-amidino-phenyl)-5-[(2-methoxycarbonyl-ethyl)-aminocarbonyl]-1-propargyl-benzimidazole

(99) 2-(4-amidino-phenyl)-6-[N-methanesulphonyl-N-(3-methoxycarbonyl-propyl)-amino]-3-methyl-imidazo[4,5-b]pyridine (100) 2-(4-amidino-phenyl)-5-[(2-methoxycarbonyl-ethyl)-aminosulphonyl]-1-methyl-benzimidazole (101) 2-(4-amidino-phenyl)-5-(methoxycarbonylmethyl-aminosulphonyl)-1-methyl-benzimidazole (102) 2-(4-amidino-phenyl)-5-[N-(4-methoxycarbonyl-cyclohexyl)-methyl-methylamino]-3-methyl-imidazo[4,5-b]pyridine (103) 2-(4-amidino-phenyl)-5-(4-methoxycarbonylmethyl-1-piperazinyl)-3-methyl-imidazo[4,5-b]pyridine (104) 2-(4-amidino-phenyl)-5-(4-methoxycarbonylmethyl-3-oxo-1-piperazinyl)-3-methyl-imidazo[4,5-b]pyridine (105) 5-[(2-methoxycarbonyl-ethyl)-aminocarbonyl]-1-methyl-2-(4-methylamidino-phenyl)-benzimidazole Concentrated aqueous methylamine solution is used (106) 2-(n-butylamidino-phenyl)-5-[(2-methoxycarbonyl-ethyl)-aminocarbonyl]-1-methyl-benzimidazole n-Butylamine is used.

(107) 2-(4-amidino-phenyl)-5-[(4-methoxycarbonyl-cyclohexyl)-amino]-3-methyl-imidazo[4,5-b]pyridine (108) 2-(4-amidino-phenyl)-5-[N-(2-methoxycarbonyl-ethyl)-methylaminosulphonyl]-1-methyl-benzimidazole (109) 8-(4-amidino-phenyl)-1-(N-methoxycarbonyl-methyl-methylaminocarbonylmethyl)-3-methyl-xanthine (110) 2-(4-amidino-phenyl)-1-(6-amino-hexyl)-5-[(2-methoxycarbonyl-ethyl)-aminocarbonyl]-benzimidazole (111) 2-(4-amidino-phenyl)-5 (6)-[(2-methoxycarbonyl-ethyl)-sulphonyl]-benzimidazole (112) 2-(4-amidino-phenyl)-5 (6)-[(3-methoxycarbonyl-propyl)-sulphonyl]-benzimidazole (113) 2-(4-amidino-phenyl)-5 (6)-[(2-methoxycarbonyl-ethyl)-sulphonylmethyl]-benzimidazole (114) 2-(4-amidino-phenyl)-1-[3-(S,S-dioxido-thiomorpholino)-propyl]-5-[(2-methoxycarbonyl-ethyl)-aminocarbonyl]-benzimidazole (115) 2-(4-amidino-phenyl)-5-[(2-methoxycarbonyl-ethyl)-aminocarbonyl]-1-(3-methylsulphonyl-phenyl)-benzimidazole (116) 2-(4-amidino-phenyl)-1-[2-(S,S-dioxido-thiomorpholinocarbonyl)-ethyl]-5-[(2-methoxycarbonyl-ethyl)-aminocarbonyl]-benzimidazole (117) 2-(4-amidino-phenyl)-5-[(2-methoxycarbonyl-ethyl)-aminocarbonyl]-1-(3-methylsulphonyl-propyl)-benzimidazole (118) 2-(4-amidino-phenyl)-1-[2-(4-benzyl-piperazino)-ethyl]-5-[(2-methoxycarbonyl-ethyl)-aminocarbonyl]-benzimidazole $R_f$ value: 0.49 (silica gel; methylene chloride/methanol=8:2)

(119) 2-(4-amidino-phenyl)-5-[(2-methoxycarbonyl-ethyl)-aminocarbonyl]-1-n-tetradecyl-benzimidazole $R_f$ value: 0.04 (silica gel; ethyl acetate/ethanol=8:2)

(120) 2-(4-amidino-phenyl)-5-[(2-methoxycarbonyl-ethyl)-aminocarbonyl]-1-(3-methoxycarbonyl-propyl)-benzimidazole-hydrochloride $R_f$ value: 0.45 (silica gel; methylene chloride/methanol=8:2)

(121) 2-(4-amidino-phenyl)-1-(3-carboxy-propyl)-5-[(2-methoxycarbonyl-ethyl)-aminocarbonyl]-benzimidazole Obtained as a by-product in (120) $R_f$ value: 0.19 (silica gel; methylene chloride/methanol=8:2)

(122) 2-(4-amidino-phenyl)-5-[(2-methoxycarbonyl-ethyl)-aminocarbonyl]-1-(4-phenyl-butyl)-benzimidazole Melting point: 184°–186° C. $R_f$ value: 0.13 (Reversed Phase Plate RP18; methanol/5% sodium chloride solution=6:4)

(123) 2-(4-amidino-phenyl)-5-[(2-methoxycarbonyl-ethyl)-aminocarbonyl]-1-methyl-6-methylamino-benzimidazole-hydrochloride-hydrogen acetate Melting point: 260°–268° C. (decomp.) $R_f$ value: 0.24 (silica gel; methylene chloride/methanol/conc. ammonia=8:2:0.1)

(124) 2-(4-amidino-phenyl)-5-[(2-methoxycarbonyl-ethyl)-aminocarbonyl]-6-(N-methoxycarbonylmethyl-methylamino)-1-methyl-benzimidazole-hydrochloride $R_f$ value: 0.42 (silica gel; methylene chloride/methanol/conc. ammonia=5:2:0.2)

(125) 2-(4-amidino-phenyl)-1-[2-(4-amino-3f5-dibromo-phenyl)-ethyl]-5-[(2-methoxycarbonyl-ethyl)-aminocarbonyl]-benzimidazole Melting point: 185° C. (sintering from 165° C.) $R_f$ value: 0.43 (Reversed Phase Plate RP18; methanol/5% sodium chloride solution=6:4)

(126) 2-(4-amidino-phenyl)-1-(3,3-diphenyl-propyl)-5-[(2-methoxycarbonyl-ethyl)-aminocarbonyl]-benzimidazole Melting point: above 200° C., $R_f$ value: 0.11 (Reversed Phase Plate RP18; methanol/5% sodium chloride solution=6:4)

(127) 2-(4-amidino-phenyl)-5-[(2-methoxycarbonyl-2-methylpropyl)-aminocarbonyl]-1-methyl-benzimidazole (128) 2-(4-amidino-phenyl)-5-[(2-methoxycarbonyl-propyl)-aminocarbonyl]-1-methyl-benzimidazole (129) 2-(4-amidino-phenyl)-5-[(2-methoxycarbonyl-4-phenyl-butyl)-aminocarbonyl]-1-methyl-benzimidazole
(130) 2-(4-amidino-phenyl)-6-(N-isobutyloxycarbonyl-N-methyl-amino)-5-[(2-methoxycarbonyl-ethyl)-aminocarbonyl]-1-methyl-benzimidazole Melting point: 104°–106° C. (decomp.) $R_f$ value: 0.76 (silica gel; methylene chloride/methanol/conc. ammonia=3:1:0.1)

(131) 8-(4-amidino-phenyl)-2-[(2-methoxycarbonyl-ethyl)-aminocarbonyl]-7-methyl-purine
(132) 8-(4-amidino-phenyl)-6-methoxy-2-[(2-methoxycarbonyl-ethyl)-aminocarbonyl]-7-methyl-purine
(133) 8-(4-amidino-phenyl)-6-dimethylamino-2-[(2-methoxycarbonyl-ethyl)-aminocarbonyl]-7-methyl-purine
(134) 8-(4-amidino-phenyl)-6-amino-2-[(2-methoxycarbonyl-ethyl)-aminocarbonyl]-7-methyl-purine
(135) 8-(4-amidino-phenyl)-2-[(2-methoxycarbonyl-ethyl)-aminocarbonyl]-7-methyl-6-piperidino-purine
(136) 8-(4-amidino-phenyl)-2-[(2-methoxycarbonyl-ethyl)-aminocarbonyl]-7-methyl-hypoxanthine
(137) 2-(4-amidino-phenyl)-7-[(2-methoxycarbonyl-ethyl)-aminocarbonyl]-imidazo[1,2-a]pyridine
(138) 2-(4-amidino-phenyl)-7-[(2-methoxycarbonyl-ethyl)-aminocarbonyl]-imidazo[1,2-a]pyrimidine
(139) 2-(4-amidino-phenyl)-7-[(2-methoxycarbonyl-ethyl)-aminocarbonyl]-imidazo[1,2-c]pyrimidine
(140) 2-(4-amidino-phenyl)-5-[(2-methoxycarbonyl-ethyl)-aminocarbonyl]-benzothiazole
(141) 8-(4-amidino-phenyl)-3,9-dimethyl-1-(4-methoxycarbonyl-butyl)-xanthine hydrochloride-hydroacetate Melting point: 224°–226° C. (decomp.) $R_f$ value: 0.58 (silica gel; n-butanol/glacial acetic acid/water=4:1:1.5)

(142) 2-(4-amidino-phenyl)-7-[(2-methoxycarbonyl-ethyl)-aminocarbonyl]-3-methyl-imidazo[1,2-a]pyridine
(143) 2-(4-amidino-phenyl)-5-[(2-methoxycarbonyl-ethyl)-aminocarbonyl]-1-methyl-6-(3-phenyl-propyloxy)-benzimidazole
(144) 2-(4-amidino-phenyl)-5-[(2-methoxycarbonyl-ethyl)-aminocarbonyl]-1-(4-methyl-benzyl)-benzimidazole
(145) 2-(4-amidino-phenyl)-1-[2-(3,5-dichloro-4-hydroxy-phenyl)-ethyl]-5-[(2-methoxycarbonyl-ethyl)-aminocarbonyl]-benzimidazole
(146) 2-(4-amidino-phenyl)-5-[(2-methoxycarbonyl-ethyl)-aminocarbonyl]-1-[(2-phenyl-ethyl)-aminocarbonylmethyl]-benzimidazole
(147) 2-(4-amidino-phenyl)-5-[(3-methoxycarbonyl-piperidino)-carbonyl]-1-methyl-benzimidazole $R_f$ value: 0.61 (Reversed-Phase-Plate RP18; methanol/5% sodium chloride solution=6:4)
(148) 2-(4-amidino-phenyl)-5-[(3-methoxycarbonyl-pyrrolidino)-carbonyl]-1-methyl-benzimidazole
(149) 2-(4-amidino-phenyl)-5-[(2-methoxycarbonyl-pyrrolidino)-carbonyl]-1-methyl-benzimidazole $R_f$ value: 0.26 (Reversed-Phase-Plate RP18; methanol/5% sodium chloride solution=6:4)

EXAMPLE 4

2-(4-Cyano-phenyl)-5(6)-[(2-methoxycarbonyl-ethyl)-carbonylamino]-benzimidazole

To a mixture of 1.5 g of 5(6)-amino-2-(4-cyano-phenyl)-benzimidazole, 0.84 g of N-ethyl-diisopropylamine, 20 ml of methylene chloride and 0.05 g of 4-dimethylamino-pyridine, 0.98 g of methylsuccinate chloride are added dropwise. The mixture is left to stand for 16 hours at ambient temperature and then slightly acidified water containing very little methanol is added thereto. The crystals obtained are taken up in a mixture of ethyl acetate, tetrahydrofuran and methanol, stirred with 0.1N hydrochloric acid, the organic solvents are distilled off in vacuo, and the precipitate obtained is filtered off. Yield: 1.4 g (63% of theory), Melting point: 154°–156° C.

EXAMPLE 5

2-(4-Amidino-phenyl)-5-[(2-methoxycarbonyl-ethyl)-aminocarbonyl]-1-[3-(S-oxido-thiomorpholino)-propyl]-benzimidazole-hydrochloride 2.2 g of 2-(4-amidino-phenyl)-5-[(2-methoxycarbonyl-ethyl)-aminocarbonyl]-1-(3-thiomorpholino-propyl)-benzimidazole-hydrochloride are dissolved in 45 ml of glacial acetic acid and a solution of 0.39 ml of 30% hydrogen peroxide in 5 ml of glacial acetate acid is added thereto whilst cooling with ice water. The mixture is stirred for 4 hours whilst cooling with ice and for 16 hours at ambient temperature, the solvent is evaporated off in vacuo and the residue is purified by column chromatography (silica gel; methylene chloride/methanol/water=1:1:0 to 1:1:0.1). Yield: 0.6 g (26% of theory), $R_f$ value: 0.46 (silica gel; methylene chloride/methanol/conc. ammonia=1:1:0.1)

The following compounds are obtained analogously:
(1) 2-(4-amidino-phenyl)-5(6)-[(2-methoxycarbonyl-ethyl)-sulphinyl]-benzimidazole
(2) 2-(4-amidino-phenyl)-5(6)-[(3-methoxycarbonyl-Propyl)-sulphinyl]-benzimidazole
(3) 2-(4-amidino-phenyl)-5(6)-[(2-methoxycarbonyl-ethyl)-sulphinylmethyl]-benzimidazole
(4) 2-(4-amidino-phenyl)-5-[(2-methoxycarbonyl-ethyl)-aminocarbonyl]-1-(3-methylsulphinyl-phenyl)-benzimidazole
(5) 2-(4-amidino-phenyl)-5-[(2-methoxycarbonyl-ethyl)-aminocarbonyl]-1-(3-methylsulphinyl-propyl)-benzimidazole
(6) 2-(4-amidino-phenyl)-1-[3-(S,S-dioxido-thiomorpholino)-propyl]-5-[(2-methoxycarbonyl-ethyl)-aminocarbonyl]-benzimidazole-hydrochloride The work is done with ten times the amount of hydrogen peroxide whilst heating to 50° C. for 7 hours $R_f$ value: 0.26 (silica gel; butanol/glacial acetic acid/water=4:1:2, after developing twice)

(7) 2-(4-amidino-phenyl)-5-[(2-methoxycarbonyl-ethyl)-aminocarbonyl]-1-[2-(S-oxido-thiomorpholinocarbonyl)-ethyl]-benzimidazole

EXAMPLE 6

2-(4-Aminomethyl-phenyl)-1-(3-amino-propyl)-5-[(2-methoxycarbonyl-ethyl)-aminocarbonyl]-benzimidazole 3 g of 1-(3-amino-propyl)-2-(4-cyano-phenyl)-5-[(2-methoxycarbonyl-ethyl)-aminocarbonyl]-benzimidazole are treated in a mixture of 50 ml of methanol and 10 ml of methanolic hydrochloric acid with 5 bars of hydrogen in the presence of 1 g of 10% palladium/charcoal for 20 hours at ambient temperature. After the catalyst has been filtered off the mixture is evaporated to dryness in vacuo and the residue is purified by chromatography on silica gel (eluant:methanol/2N ammonia=5:1.5 to 5:2). Yield: 1.5 g (55% of theory), $R_f$ value: 0.24 (silica gel; methanol/2N ammonia=5:1.5 after developing twice)

The following compounds are obtained analogously:

(1) 2-(4-aminomethyl-phenyl)-5(6)-[(2-methoxycarbonyl-ethyl)-aminocarbonyl]-benzimidazole-hydrochloride (2) 2-(4-aminomethyl-phenyl)-5-[(2-methoxycarbonyl-ethyl)-aminocarbonyl]-1-(3-thiomorpholino-propyl)-benzimidazole $R_f$ value: 0.40 (silica gel; methylene chloride/methanol/conc. ammonia=8:2:0.1)

(3) 2-(4-aminomethyl-phenyl)-5-[(3-methoxycarbonyl-Propyl)-aminocarbonyl]-1-methyl-benzimidazole (4) 2-(4-aminomethyl-phenyl)-5-[(2-methoxycarbonyl-ethyl)-aminocarbonyl]-1-methyl-benzimidazole-dihydrochloride Melting point: sintering from 185° C. $R_f$ value: 0.57 (Reversed Phase Plate RP18; methanol/5% sodium chloride solution=6:4)

(5) 2-(4-aminomethyl-phenyl)-6-[(2-methoxycarbonyl-ethyl)-aminocarbonyl]-imidazo[4,5-b]pyridine (6) 2-(4-aminomethyl-phenyl)-1-[2-(3,4-dimethoxy-Phenyl)-ethyl]-5-[(2-methoxycarbonyl-ethyl)-aminocarbonyl]-benzimidazole-dihydrochloride $R_f$ value: 0.03 (silica gel; ethyl acetate/ethanol/conc. ammonia=8:2:0.02)

(7) 2-(4-aminomethyl-phenyl)-5-[(2-methoxycarbonyl-ethyl)-aminocarbonyl]-1-n-tetradecyl-benzimidazole-dihydrochloride $R_f$ value: 0.03 (silica gel; ethyl acetate/ethanol/conc. ammonia=50:2:0.02)

EXAMPLE 7

2-(4-Aminomethyl-cyclohexyl)-5-[(2-carboxy-ethyl)-aminocarbonyl]-1-methyl-benzimidazole Prepared from 5-[(2-carboxy-ethyl)-aminocarbonyl]-1-methyl- 2-(4-phthalimidomethyl-cyclohexyl)-benzimidazole by treating for 20 hours with 40% aqueous methylamine solution at ambient temperature.

The following compounds are obtained analogously:
(1) 2-[4-(2-amino-ethyl)-phenyl]-5-[(3-carboxy-propyl)-carbonyl]-1-methyl-benzimidazole
(2) 2-[4-(2-amino-ethyl)-phenyl]-5-[(2-carboxy-ethyl)-carbonyl]-1-methyl-benzimidazole
(3) 2-(4-amino-cyclohexyl)-5-[(2-carboxy-ethyl)-aminocarbonyl]-1-methyl-benzimidazole

EXAMPLE 8

2-(4-Aminomethyl-cyclohexyl)-5-[(2-methoxycarbonyl-ethyl)-aminocarbonyl]-1-methyl-benzimidazole-dihydrochloride Prepared from 2-(4-aminomethyl-cyclohexyl)-5-[(2-carboxy-ethyl)-aminocarbonyl]-1-methyl-benzimidazole by treating with saturated methanolic hydrochloric acid at ambient temperature.

The following compounds are obtained analogously:
(1) 2-[4-(2-amino-ethyl)-phenyl]-5-[(3-methoxycarbonyl-propyl)-carbonyl]-1-methyl-benzimidazole-dihydrochloride
(2) 2-[4-(2-amino-ethyl)-phenyl]-5-[(2-methoxycarbonyl-ethyl)-carbonyl]-1-methyl-benzimidazole-dihydrochloride
(3) 5-[(2-methoxycarbonyl-ethyl)-aminocarbonyl]-1-methyl-2-(4-methylaminomethyl-phenyl)-benzimidazole-dihydrochloride
(4) 2-(4-amino-cyclohexyl)-5-[(2-methoxycarbonyl-ethyl)-aminocarbonyl]-1-methyl-benzimidazole-dihydrochloride

EXAMPLE 9

5-[(2-carboxy-ethyl)-aminocarbonyl]-1-methyl-2-(4-methylaminomethyl-phenyl)-benzimidazole Prepared from 5-[(2-carboxy-ethyl)-aminocarbonyl]-1-methyl-2-[4-(N-trifluoroacetyl-methylaminomethyl)-phenyl]-benzimidazole by treating with 2N sodium hydroxide solution.

EXAMPLE 10

2-(1-Amidino-4-piperidinyl)-5-[(2-methoxycarbonyl-ethyl)-aminocarbonyl]-1-methyl-benzimidazole Prepared from 5-[(2-methoxycarbonyl-ethyl)-aminocarbonyl]-1-methyl-2-(4-piperidinyl)-benzimidazole and S-ethylisothiourea-hydrobromide by heating to 100° C. for 4 hours in dimethylformamide in the presence of sodium carbonate.

The following compounds are obtained analogously:
(1) 2-(4-guanidinomethyl-phenyl)-5-[(2-methoxycarbonyl-ethyl)-carbonyl]-1-methyl-benzimidazole
(2) 2-(4-amidino-1-piperazinyl)-5-[(2-methoxycarbonyl-ethyl)-aminocarbonyl]-1-methyl-benzimidazole

EXAMPLE 11

2-(3-Guanidino-phenyl)-5-[(3-methoxycarbonyl-propyl)-aminocarbonyl]-1-methyl-benzimidazole Prepared from 2-(3-amino-phenyl)-5-[(3-methoxycarbonyl-propyl)-aminocarbonyl]-1-methyl-benzimidazole-hydrochloride by refluxing for 3 hours with cyanamide in dioxane.

EXAMPLE 12

2-(4-Methoxycarbonylamidino-phenyl)-5-[(2-methoxycarbonyl-ethyl)-aminocarbonyl]-1-methyl-benzimidazole 0.26 g of 2-(4-amidino-phenyl)-5-[(2-methoxycarbonyl-ethyl)-aminocarbonyl]-1-methyl-benzimidazole-hydrochloride are suspended in 50 ml of methylene chloride and, whilst cooling with ice, 0.5 ml of N-ethyl-diisopropylamine and 0,067 ml of methyl chloroformate are added. The mixture is stirred at ambient temperature, after half an hour a further 0.5 ml of N-ethyl-diisopropylamine and 0.03 ml of methyl chloroformate are added and, after another half hour, a further 0.1 ml of N-ethyl-diisopropylamine and 0.03 ml of methyl chloroformate. The mixture is stirred for a further half hour, evaporated down in vacuo and purified by column chromatography (silica gel; eluant:ethyl acetate/ethanol=100:2.5 to 100:12.5). Yield: 0.12 g (40% of theory), $R_f$ value: 0.41 (silica gel; ethyl acetate/ethanol=8:2)

The following compounds are obtained analogously:
(1) 2-(4-isobutyloxycarbonylamidino-phenyl)-5-[(2-methoxycarbonyl-ethyl)-aminocarbonyl]-1-methyl-benzimidazole
(2) 5-[(2-ethoxycarbonyl-ethyl)-aminocarbonyl]-2-(4-methoxycarbonylamidino-phenyl)-1-methyl-benzimidazole
(3) 5-[(2-isobutyloxycarbonyl-ethyl)-aminocarbonyl]-2-(4-methoxycarbonylamidino-phenyl)-1-(4-phenyl-butyl)-benzimidazole
(4) 2-(4-acetoxymethyloxycarbonylamidino-phenyl)-5-[(2-methoxycarbonyl-ethyl)-aminocarbonyl]-1-(4-phenyl-butyl)-benzimidazole (5) 2-(4-cyano-phenyl)-6-(N-isobutyloxycarbonyl-N-methyl-amino)-5-[(2-methoxycarbonyl-ethyl)-aminocarbonyl]-1-methyl-benzimidazole $R_f$ value: 0.63 (silica gel; methylene chloride/methanol/glacial acetic acid=25:1:0.1)

EXAMPLE 13

2-(4-Amidino-phenyl)-1-[2-(3,4-dimethoxy-phenyl)-ethyl]-5-[(2-isopropyloxycarbonyl-ethyl)-aminocarbonyl]-benzimidazole-dihydrochloride 0.6 g of 2-(4-amidino-phenyl)-1-[2-(3,4-dimethoxy-phenyl)-ethyl]-5-[(2-methoxycarbonyl-ethyl)-aminocarbonyl]-benzimidazole-hydrochloride are added to 50 ml of ice-cold saturated isopropanolic hydrochloric acid, petroleum ether is poured on top and stirred in carefully until the majority of the solid product has gone into solution. The mixture is left at ambient temperature for 16 hours, the precipitate is filtered off, the filtrate is evaporated down in vacuo and the residue is stirred with tetrahydrofuran. Yield: 0.5 g (76% of theory), Melting point: 210° C. (sintering from 180° C.)

The following compounds are obtained analogously:
(1) 2-(4-amidino-phenyl)-5-[(2-n-butyloxycarbonyl-ethyl)-aminocarbonyl]-1-methyl-benzimidazole dihydrochloride (2) 2-(4-amidino-phenyl)-5-[(2-isopropyloxycarbonyl-ethyl)-aminocarbonyl]-1-(4-phenyl-butyl)-benzimidazole dihydrochloride (3) 2-(4-amidino-phenyl)-5-[(2-cyclohexyloxycarbonyl-ethyl)-aminocarbonyl]-1-(4-phenyl-butyl)-benzimidazole dihydrochloride $R_f$ value: 0.69 (silica gel; n-butanol/glacial acetic acid/water=3:1:1)

(4) 2-(4-amidino-phenyl)-5-[(2-n-hexyloxycarbonyl-ethyl)-aminocarbonyl]-1-(4-phenyl-butyl)-benzimidazole dihydrochloride (5) 2-(4-amidino-phenyl)-5-[(2-isobutyloxycarbonyl-ethyl)-aminocarbonyl]-1-(4-phenyl-butyl)-benzimidazole dihydrochloride (6) 2-(4-amidino-phenyl)-5-[(2-cyclohexylmethyloxycarbonyl-ethyl)-aminocarbonyl]-1-(4-phenyl-butyl)-benzimidazole dihydrochloride $R_f$ value: 0.67 (silica gel; n-butanol/glacial acetic acid/water=3:1:1)

(7) 2-(4-amidino-phenyl)-5-[[2-(2-indanyloxycarbonyl)-ethyl]-aminocarbonyl]-1-methyl-benzimidazole-dihydrochloride The corresponding carboxylic acid is used as starting material and is heated in the presence of hydrogen chloride.

(8) 2-(4-amidino-phenyl)-1-methyl-5-[[2-[(1-naphthyl)-methyloxycarbonyl]-ethyl]-aminocarbonyl]-benzimidazole-dihydrochloride The same procedure is used as in (7)

(9) 2-(4-amidino-phenyl)-5-[(2-cinnamyloxycarbonyl-ethyl)-aminocarbonyl]-1-methyl-benzimidazole-dihydrochloride The same procedure is used as in (7)

(10) 2-(4-amidino-phenyl)-1-methyl-5-[[2-[(2-norbornyl)-methyloxycarbonyl]-ethyl]-aminocarbonyl]-benzimidazole-dihydrochloride $R_f$ value: 0.75 (silica gel; dichloromethane/methanol=2:1)

(11) 2-(4-amidino-phenyl)-1-methyl-5-[[2-(2-norbornyloxycarbonyl)-ethyl]-aminocarbonyl]-benzimidazole-dihydrochloride The same procedure is used as in (7)

(12) 2-(4-amidino-phenyl)-1-methyl-5-[[2-[(5-phenyl-butyl)-oxycarbonyl]-ethyl]-aminocarbonyl]-benzimidazole-dihydrochloride The same procedure is used as in (7)

(13) 2-(4-amidino-phenyl)-1-methyl-5-[[2-[(4-phenyl-butyl)-oxycarbonyl]-ethyl]-aminocarbonyl]-benzimidazole-dihydrochloride The same procedure is used as in (7)

(14) 2-(4-amidino-phenyl)-5-[(2-cyclooctyloxycarbonyl-ethyl)-aminocarbonyl]-1-methyl-benzimidazole-dihydrochloride $R_f$ value: 0.67 (silica gel; n-butanol/glacial acetic acid/water=3:1:1)

(15) 2-(4-amidino-phenyl)-1-(4-phenyl-butyl)-5-[[2-[(2-phenyl-ethyl)-oxycarbonyl]-aminocarbonyl]-benzimidazole-dihydrochloride $R_f$ value: 0.78 (silica gel; n-butanol/glacial acetic acid/water=3:1:1)

(16) 2-(4-amidino-phenyl)-1-[2-(4-amino-3,5-dibromo-phenyl)-ethyl]-5-[(2-isopropyloxycarbonyl-ethyl)-aminocarbonyl]-benzimidazole-dihydrochloride $R_f$ value: 0.18 (Reversed-Phase-Plate RP18; methanol/5% sodium chloride solution=6:4)

(17) 2-(4-amidino-phenyl)-1-[2-(2-bromo-4,5-dimethoxy-phenyl)-ethyl]-5-[[2-(2-norbornyloxycarbonyl)-ethyl]-aminocarbonyl]-benzimidazole-dihydroacetate 2-(4-Amidino-phenyl)-5-[(2-carboxy-ethyl)-aminocarbonyl]-1-[2-(3,4-dimethoxy-phenyl)-ethyl]-benzimidazole-dihydrobromide is heated with thionyl chloride for 2 hours and the resulting acid chloride is converted to the corresponding ester with norborneol.

The purification is done by chromatography over silica gel (eluant:n-butanol/glacial acetic acid/water=3:1:1). $R_f$ value: 0.72 (silica gel; n-butanol/glacial acetic acid/water=3:1:1)

(18) 2-(4-amidino-phenyl)-1-[2-(2-bromo-4,5-dimethoxy-phenyl)-ethyl]-5-[[2-(2-indanyloxycarbonyl)-ethyl]-aminocarbonyl]-benzimidazole-dihydroacetate The same procedure is used as in (17) $R_f$ value: 0.65 (silica gel; n-butanol/glacial acetic acid/water=3:1:1)

EXAMPLE 14

2-[(4-Cyano-phenyl)-oxymethyl]-5(6)-ethoxycarbonylmethoxy-benzimidazole 4.5 g of ethyl 3-amino-4-[(4-cyano-phenyl)-oxymethylcarbonylamino]-phenoxy-acetate are melted and kept at 200° C. for 15 minutes. The product is purified by column chromatography, initially over silica gel (eluant:methylene chloride/methanol/conc. ammonia=30:1:0.1) and subsequently over neutral aluminium oxide (eluant:methylene chloride/methanol=100:1) and crystallised from a 1:2 mixture of methylene chloride and ether. Yield: 2.5 g (58% of theory), Melting point: 111°-112° C. $R_f$ value: 0.22 (silica gel; methylene chloride/methanol/conc. ammonia=30:1:0.1)

The following compounds are obtained analogously:
(1) 1-[2-(4-benzyl-piperazino)-ethyl]-2-(4-cyano-phenyl)-5-[(2-methoxycarbonyl-ethyl)-aminocarbonyl]-benzimidazole $R_f$ value: 0.58 (silica gel; methylene chloride/methanol/conc. ammonia=19:1:0.1, after developing three times (2) 1-(3-amino-propyl)-2-(4-cyano-phenyl)-5-[(2-methoxycarbonyl-ethyl)-aminocarbonyl]-benzimidazole-hydrochloride 3-amino-4-(3-amino-propylamino)-benzoic acid-[N-(2-methoxycarbonyl-ethyl)-amide]-hydrochloride-hydrogen acetate is initially acylated by treating with 4-cyano-benzoyl chloride in chlorobenzene at a bath temperature of 140° C. and the chlorobenzene is distilled off simultaneously. The residue is heated to 190° C. for 10 minutes.

Melting point: 252° C. (decomp., sintering from 115° C.) $R_f$ value: 0.54 (silica gel; methylene chloride/methanol/conc. ammonia=9:1:0.2, after developing twice)

(3) 2-(4-cyano-phenyl)-5-[(2-methoxycarbonyl-ethyl)-aminocarbonyl]-1-methyl-6-methylamino-benzimidazole Heating is carried out for 35 minutes.

Melting point: 203°–205° C. $R_f$ value: 0.68 (silica gel; methylene chloride/methanol/conc. ammonia=30:1:0.1, after developing three times)

(4) 8-(4-cyan-phenyl)-3,9-dimethyl xanthine 5-amino-3-methyl-4-methylamino-pyrimidin-2,6-dione was acylated with 4-cyan-benzoyl chloride in the presence of 4-dimethylamino-pyridine in tetrahydrofurane and the evaporation residue was heated to 200°–205° C. for 45 minutes. $R_f$ value: 0.79 (silica gel; methylene chloride/methanol/glacial acetic acid=9:1:0.1, after developing two times)

EXAMPLE 15

2-(4-Amidino-phenyl)-5-[(2-carboxy-ethyl)-aminocarbonyl]-1-(2-piperazino-ethyl)-benzimidazole-hydrogen acetate 0.30 g of 2-(4-amidino-phenyl)-1-[2-(4-benzyl-piperazino)-ethyl]-5-[(2-carboxy-ethyl)-aminocarbonyl]-benzimidazole are dissolved in 100 ml of glacial acetic acid and treated with 5 bars of hydrogen in the presence of 1.8 g of palladium oxide at ambient temperature for 36 hours. After the catalyst has been filtered off the filtrate is evaporated down in vacuo and the residue is digested with acetone and then ether. Yield: 0.27 g (92% of theory), Melting point: 80° C. (decomp.) $R_f$ value: 0.14 (silica gel; isopropanol/water/conc. ammonia=7:2:1, after developing twice)

The following compounds are obtained analogously:
(1) 2-(4-amidino-phenyl)-5(6)-[(2-methoxycarbonyl-ethyl)-aminocarbonyl]-benzimidazole-hydrochloride The work is done in methanol with 10% palladium/charcoal. $R_f$ value: 0.65 (silica gel; methylene chloride/methanol=3:1)

(2) 2-(4-amidino-phenyl)-1-(4-phenyl-butyl)-5-[( 2-pivaloyloxymethyloxycarbonyl-ethyl)-aminocarbonyl]-benzimidazole (3) 2-(4-amidino-phenyl)-5-[[2-[(1-ethoxycarbonyloxy-ethyl)-oxycarbonyl]-ethyl]-aminocarbonyl]-1-(4-phenyl-butyl)-benzimidazole (4) 2-(4-amidino-phenyl)-5-[(2-cyclohexyloxycarbonyloxy-methyloxycarbonyl-ethyl)-aminocarbonyl]-1-(4-phenyl-butyl)-benzimidazole (5) 5-[(2-acetoxymethyloxycarbonyl-ethyl)-aminocarbonyl]-2-(4-amidino-phenyl)-1-(4-phenyl-butyl)-benzimidazole (6) 2-(4-amidino-phenyl)-5-[(1,2-bis-carboxy-ethyl)-aminocarbonyl]-1-methyl-benzimidazole (7) 2-(4-amidino-phenyl)-5-[[2-carboxy-1-[(1-carboxy-2-phenyl-ethyl)-aminocarbonyl]-ethyl]-aminocarbonyl]-1-methyl-benzimidazole (8) 2-(4-amidino-phenyl)-5-[[2-carboxy-1-[(1-carboxy-2-methyl-propyl)-aminocarbonyl]-ethyl]-aminocarbonyl]-1-methyl-benzimidazole (9) 2-(4-amidino-phenyl)-5-[[2-carboxy-1-[[1-carboxy-2-(4-hydroxy-phenyl)-ethyl]-aminocarbonyl]-ethyl]-aminocarbonyl]-1-methyl-benzimidazole

(10) 2-(4-amidino-phenyl)-5-[[2-carboxy-1-[[l-carboxy-2-(4-methoxy-phenyl)-ethyl]-aminocarbonyl]-ethyl]-aminocarbonyl]-1-methyl-benzimidazole

(11) 2-(4-amidino-phenyl)-5-[[2-carboxy-1-[[2-(4-methoxy-phenyl)-ethyl]-aminocarbonyl]-ethyl]-aminocarbonyl]-1-methyl -benzimidazole

EXAMPLE 16

2-(4-Cyano-phenyl)-5-[(2-methoxycarbonyl-ethyl)-aminocarbonyl]-1-(3-thiomorpholino-propyl)-benzimidazole 48.6 g of 3-amino-4-(3-thiomorpholino-propylamino)-benzoic acid-[N-(2-methoxycarbonyl-ethyl)-amide]-hydrochloride are dissolved in 500 ml of glacial acetic acid with heating, 19.5 g of 4-cyano-benzoylchloride are added, the mixture is heated for one hour over a steam bath and a further 2 hours at a bath temperature of 120° C. The mixture is evaporated down in vacuo and the residue is purified by chromatography on silica gel (eluant:methylene chloride/methanol/conc. ammonia=9:1:0 to 8:2:0.2). Yield: 33.7 g (58% of theory), $R_f$ value: 0.84 (silica gel; methylene chloride/methanol/conc. ammonia=19:1:0.1, after developing three times)

The following compounds are obtained analogously:
(1) 2-(4-cyano-phenyl)-1-[2-(3,4-dimethoxy-phenyl)-ethyl]-5-[(2-methoxycarbonyl-ethyl)-aminocarbonyl]-benzimidazole The acylation with 4-cyano-benzoylchloride is initially carried out in methylene chloride with the addition of N-ethyl-diisopropylamine. After the solvent has been evaporated off the residue is taken up in glacial acetic acid and heated to 100° C. for 1.5 hours. $R_f$ value: 0.36 (silica gel; ethyl acetate/ethanol/conc. ammonia=50:2:0.1)

(2) 2-(4-cyano-phenyl)-5-[(2-methoxycarbonyl-ethyl)-aminocarbonyl]-1-(3-pyridylmethyl)-benzimidazole The same procedure is used as in (1) with 3 hours of heating in glacial acetic acid $R_f$ value: 0.40 (silica gel; ethyl acetate/ethanol=8:2)

(3) 2-(4-cyano-phenyl)-5-[(2-methoxycarbonyl-ethyl)-aminocarbonyl]-1-n-tetradecyl-benzimidazole The same procedure is used as in (1) $R_f$ value: 0.60 (silica gel; ethyl acetate/ethanol/conc. ammonia=50:2:0.02)

(4) 2-(4-cyano-phenyl)-5-[(2-methoxycarbonyl-ethyl)-aminocarbonyl]-1-(3-methoxycarbonyl-propyl)-benzimidazole The same procedure is used as in (1) using triethylamine as auxiliary base. A 3:1 mixture of tetrahydrofuran and methylene chloride is used as solvent. $R_f$ value: 0.68 (silica gel; methylene chloride/methanol=37:3)

(5) 1-benzyl-2-(4-cyano-phenyl)-5-[(2-methoxycarbonyl-ethyl)-aminocarbonyl]-benzimidazole The same procedure is used as in (4). $R_f$ value: 0.77 (silica gel; methylene chloride/methanol=9: 1)

(6) 2-(4-cyano-phenyl)-5-[(2-methoxycarbonyl-ethyl)-aminocarbonyl]-1-(4-phenyl-butyl)-benzimidazole The same procedure is used as in (1). $R_f$ value: 0.61 (silica gel; ethyl acetate/ethanol=50:2)

(7) 1-[2-(4-amino-3,5-dibromo-phenyl)-ethyl]-2-(4-cyano-phenyl)-5-[(2-methoxycarbonyl-ethyl)-aminocarbonyl]-benzimidazole The same procedure is used as in (1).

Melting point: 168°–170° C., $R_f$ value: 0.66 (silica gel; ethyl acetate/ethanol=8:2)

(8) 2-(4-cyano-phenyl)-1-(3,3-diphenyl-propyl)-5-[(2-methoxycarbonyl-ethyl)-aminocarbonyl]-benzimidazole Melting point: 157°–159° C., $R_f$ value: 0.65 (silica gel; ethyl acetate/ethanol=9:1)

(9) 2-(4-cyan-phenyl)-5-[(2-methoxycarbonyl-pyrrolidino)-carbonyl]-1-methyl-benzimidazole The same procedure is used as in (1)

melting point: 174°–176° C. $R_f$ value: 0.36 (silica gel; ethyl acetate/ethanol=9:1)

(10) 2-(4-cyan-phenyl)-5-[(3-methoxycarbonyl-piperidino)-carbonyl]-1-methyl-benzimidazole The same procedure is used as in (1)

melting point: 185°–186° C. $R_f$ value: 0.43 (silica gel; ethyl acetate/ethanol=9:1)

(11) 2-(4-cyan-phenyl)-6-[(2-methoxycarbonyl-ethyl)-aminocarbonyl]-3-methyl-imidazo[4,5-b]pyridine melting point: 195°–197° C. $R_f$ value: 0.51 (silica gel; ethyl acetate/ethanol=9:1)

EXAMPLE 17

2-(4-Aminomethyl-phenyl)-1-(3-amino-propyl)-5-[(2-carboxy-ethyl)-aminocarbonyl]-benzimidazole-hydrogen acetate 0.8 g of 2-(4-aminomethyl-phenyl)-1-(3-amino-propyl)-5-[(2-methoxycarbonyl-ethyl)-aminocarbonyl]-benzimidazole are left to stand for 20 hours at ambient temperature in 10 ml of 48% hydrobromic acid. The mixture is concentrated by evaporation in vacuo and the residue is purified by chromatography on silica gel (eluant:n-butanol/glacial acetic acid/water=4:1:1 to 4:2:2). Yield: 0.6 g (67% of theory), $R_f$ value: 0.66 (Reversed Phase Plate RP18; methanol/5% sodium chloride solution/conc. hydrobromic acid=6:10:0.01)

The following compounds are obtained analogously:

(1) 2-(4-aminomethyl-phenyl)-5-[(2-carboxy-ethyl)-aminocarbonyl]-1-methyl-benzimidazole-dihydrobromide Melting point: sintering from 220° C. $R_f$ value: 0.87 (Reversed Phase Plate RP18; methanol/5% sodium chloride solution=6:4)

(2) 2-(4-amidino-phenyl)-5-[(2-carboxy-ethyl)-aminocarbonyl]-1-[2-(3,4-dimethoxy-phenyl)-ethyl]-benzimidazole-dihydrobromide $R_f$ value: 0.72 (Reversed Phase Plate RP18; methanol/5% sodium chloride solution=6:4)

(3) 2-(4-amidino-phenyl)-5-[(2-carboxy-ethyl)-aminocarbonyl]-1-(3-pyridylmethyl)-benzimidazole-dihydrobromide $R_f$ value: 0.73 (Reversed Phase Plate RP18; methanol/5% sodium chloride solution=6:4)

(4) 2-(4-aminomethyl-phenyl)-5-[(2-carboxy-ethyl)-aminocarbonyl]-1-n-tetradecyl-benzimidazole-dihydrobromide $R_f$ value: 0.05 (Reversed Phase Plate RP18; methanol/5% sodium chloride solution=6:4)

(5) 2-(4-aminomethyl-phenyl)-5-[(2-carboxy-ethyl)-aminocarbonyl]-1-[2-(3,4-dimethoxy-phenyl)-ethyl]-benzimidazole-dihydrobromide $R_f$ value: 0.67 (Reversed Phase Plate RP18; methanol/5% sodium chloride solution=6:4)

(6) 2-(4-amidino-phenyl)-5-[(2-carboxy-ethyl)-aminocarbonyl]-1-n-tetradecyl-benzimidazole-dihydrobromide $R_f$ value: 0.01 (Reversed Phase Plate RP18; methanol/5% sodium chloride solution=6:4)

(7) 2-(4-amidino-phenyl)-5-[(2-carboxy-ethyl)-aminocarbonyl]-1-(4-phenyl-butyl)-benzimidazole-dihydrobromide $R_f$ value: 0.08 (Reversed Phase Plate RP18; methanol/5% sodium chloride solution=6:4)

(8) 2-(4-amidino-phenyl)-1-[2-(4-amino-3,5-dibromo-phenyl)-ethyl]-5-[(2-carboxy-ethyl)-aminocarbonyl]-benzimidazole-dihydrobromide Melting point: above 225° C. $R_f$ value: 0.57 (Reversed Phase Plate RP18; methanol/5% sodium chloride solution=6:4)

(9) 2-(4-amidino-phenyl)-5-[(2-carboxy-ethyl)-aminocarbonyl]-1-(3,3-diphenyl-propyl)-benzimidazole-dihydrobromide $R_f$ value: 0.71 (silica gel; n-butanol/glacial acetic acid/water =3:1:1)

(10) 2-(4-amidino-phenyl)-5-[(3-carboxy-piperidino)-carbonyl]-1-methyl-benzimidazole-dihydrobromide $R_f$ value: 0.49 (Reversed-Phase-Plate RP18; methanol/5% sodium chloride solution=6:4)

(11) 2-(4-amidino-phenyl)-5-[(3-carboxy-pyrrolidino)-carbonyl]-1-methyl-benzimidazole-dihydrobromide

(12) 2-(4-amidino-phenyl)-5-[(2-carboxy-pyrrolidino)-carbonyl]-1-methyl-benzimidazole-dihydrobromide $R_f$ value: 0.46 (Reversed-Phase-Plate RP18; methanol/5% sodium chloride solution=6:4)

(13) 2-(4-amidino-phenyl)-6-[(2-carboxy-ethyl)-aminocarbonyl]-3-methyl-imidazo[4,5-b]pyridine-dihydrobromide $R_f$ value: 0.74 (Reversed-Phase-Plate RP18; methanol/5% sodium chloride solution=6:4)

EXAMPLE 18

2-(4-Cyano-phenyl)-5-[(2-methoxycarbonyl-ethyl)-aminocarbonyl]-1-methyl-benzimidazole 4.7 g of 3-amino-4-methylamino-benzoic acid-[N-(2-methoxycarbonyl-ethyl)-amide] are first stirred at ambient temperature with 40 ml of phosphorusoxychloride, then 3.1 g of 4-cyano-benzoylchloride are added and the mixture is heated to 90° C. for 8 hours. The phosphorusoxychloride is distilled off in vacuo, the residue is stirred into 500 ml of water at 30° C. and neutralised by the addition of sodium bicarbonate in batches. The precipitate is suction filtered and extracted with ethyl acetate. The ethyl acetate phases are evaporated down, the residue is combined with the precipitate and purified by chromatography on silica gel (eluant:ethyl acetate/ethanol=100:1 to 100:5). The product obtained is decocted with ethyl acetate for final purification. Yield: 1,86 g (27% of theory), $R_f$ value: 0.51 (silica gel; ethyl acetate/ethanol=9:1)

EXAMPLE 19

2-(4-Cyano-phenyl)-5-[(2-methoxycarbonyl-ethyl)-aminocarbonyl]-6-(N-methoxycarbonylmethyl-N-methyl-amino)-1-methyl-benzimidazole 5.0 g of 2-(4-cyano-phenyl)-5-[(2-methoxycarbonyl-ethyl)-aminocarbonyl]-1-methyl-6-methylamino-benzimidazole are dissolved in 20 ml of dimethylformamide in the warm and 2.3 ml of N-ethyl-di-isopropylamine are added. 1.2 ml of methyl bromoacetate are added dropwise and the mixture is heated for 5 hours over a steam bath. A further 1.2 ml of N-ethyl-diisopropylamine and 0.6 ml of methyl bromoacetate are added and the mixture is heated for a further 3 hours. After the solvent is evaporated off in vacuo, stirred for 2 hours at ambient temperature with 50 ml of water, suction filtered and the residue is dried and triturated with ethyl acetate. Yield: 3.2 g (54% of theory), Melting point: 174°–176° C. $R_f$ value: 0.34 (silica gel; methylene chloride/methanol=19:1, after developing three times)

The following compound is obtained analogously:
(1) 8-(4-cyan-phenyl)-3,9-dimethyl-1-(4-ethoxycarbonyl-butyl)-xanthine Dimethylsulfoxide was used as solvent and potassium carbonate as base, the reaction mixture was heated to 80° C. for four hours.

melting point: 148°–150° C. $R_f$ value: 0.33 (silica gel; ethyl acetate)

EXAMPLE 20

2-(4-Benzyloxycarbonylamidino-phenyl)-1-(4-phenyl-butyl)-5-[(2-pivaloyloxymethyloxycarbonyl-ethyl)-aminocarbonyl]-benzimidazole Prepared by reacting 2-(4-benzyloxycarbonylamidino-phenyl)-5-[(2-carboxy-ethyl)-aminocarbonyl]-1-(4-phenyl-butyl)-benzimidazole with pivaloyloxymethylchloride in dimethylsulphoxide in the presence of potassium carbonate with the addition of potassium iodide at ambient temperature.

The following compounds are obtained analogously:
(1) 2-(4-benzyloxycarbonylamidino-phenyl)-5-[[2-[(1-ethoxycarbonyloxy-ethyl)-oxycarbonyl]-ethyl]-aminocarbonyl]-1-(4-phenyl-butyl)-benzimidazole
(2) 2-(4-benzyloxycarbonylamidino-phenyl)-5-[(2-cyclohexyloxycarbonyloxymethyloxycarbonyl-ethyl)-aminocarbonyl]-1-(4-phenyl-butyl)-benzimidazole
(3) 5-[(2-acetoxymethyloxycarbonyl-ethyl)-aminocarbonyl]-2-(4-benzyloxycarbonylamidino-phenyl)-1-(4-phenyl-butyl)-benzimidazole

EXAMPLE 21

2-(4-Diethylphosphorylamidino-phenyl)-5-[(2-methoxycarbonyl-ethyl)-aminocarbonyl]-1-(4-phenyl-butyl)-benzimidazole Prepared by reacting 2-(4-amidino-phenyl)-5-[(2-methoxycarbonyl-ethyl)-aminocarbonyl]-1-(4-phenyl-butyl)-benzimidazole with diethylphosphorylcyanide in dimethylformamide.

EXAMPLE 22

2-(4-Benzyloxycarbonylamidino-phenyl)-5-[(1,2-bis-benzyloxycarbonyl-ethyl)-aminocarbonyl]-1-methyl-benzimidazole Prepared from 2-(4-benzyloxycarbonylamidino-phenyl)-1-methyl-benzimidazole-4-carboxylic acid and dibenzyl aspartate with the addition of 2-(1H-benztriazol-1-yl)-1,1,3,3-tetramethyluronium-tetrafluoroborate in tetrahydrofuran.

The following compounds are obtained analogously:
(1) 2-(4-benzyloxycarbonylamidino-phenyl)-5-[[2-benzyloxycarbonyl-1-[(1-benzyloxycarbonyl-2-phenyl-ethyl)-aminocarbonyl]-ethyl]-aminocarbonyl]-1-methyl-benzimidazole
(2) 2-(4-benzyloxycarbonylamidino-phenyl)-5-[[2-benzyloxycarbonyl-1-[(1-benzyloxycarbonyl-2-methyl-propyl)-aminocarbonyl]-ethyl]-aminocarbonyl]-1-methyl-benzimidazole
(3) 2-(4-benzyloxycarbonylamidino-phenyl)-5-[[2-benzyloxycarbonyl-1-[(1-benzyloxycarbonyl-2-(4-benzyloxy-phenyl)-ethyl]-aminocarbonyl]-ethyl]-aminocarbonyl]-1-methyl-benzimidazole
(4) 2-(4-benzyloxycarbonylamidino-phenyl)-5-[[2-benzyloxycarbonyl-1-[[1-benzyloxycarbonyl-2-(4-methoxy-phenyl)-ethyl]-aminocarbonyl]-ethyl]-aminocarbonyl]-1-methyl-benzimidazole
(5) 5-[[2-benzyloxycarbonyl-1-[[2-(4-methoxy-phenyl)-ethyl]-aminocarbonyl]-ethyl]-aminocarbonyl]-2-(4-benzyloxycarbonyl-amidino-phenyl)-1-methyl-benzimidazole

EXAMPLE 23

2-[4-(1-Amino-cyclopropyl)-phenyl]-5-[(2-methoxycarbonyl-ethyl)-aminocarbonyl]-1-methyl-benzimidazole Prepared from 2-[4-(1-tert.butyloxycarbonylamino-cyclopropyl)-phenyl]-5-[(2-methoxycarbonyl-ethyl)-aminocarbonyl]-1-methyl-benzimidazole by treating with trifluoroacetic acid in methylene chloride at ambient temperature.

The following compound is obtained analogously:
(1) 2-[4-(1-amino-cyclopentyl)-phenyl]-5-[(2-methoxycarbonyl-ethyl)-aminocarbonyl]-1-methyl-benzimidazole

EXAMPLE 24

2-(1-Amino-5-indanyl)-5-[(2-methoxycarbonyl-ethyl)-aminocarbonyl]-1-methyl-benzimidazole Prepared from 2-(1-hydroxyimino-5-indanyl)-5-[(2-methoxycarbonyl-ethyl)-aminocarbonyl]-1-methyl-benzimidazole by reduction with 5 bars of hydrogen in a 50:1 mixture of methanol and methanolic hydrochloric acid at ambient temperature in the presence of 10% palladium/charcoal.

The following compound is obtained analogously:
(1) 2-(1-amino-1,2,3,4-tetrahydro-6-naphthyl)-5-[(2-methoxycarbonyl-ethyl)-aminocarbonyl]-1-methyl-benzimidazole

EXAMPLE 25

2-[4-(2-Amino-2-propyl)-phenyl]-5-[(2-methoxycarbonyl-ethyl)-aminocarbonyl]-1-methyl-benzimidazole Prepared from 2-[4-(2-aminocarbonyl-2-propyl)-phenyl]-5-[(2-methoxycarbonyl-ethyl)-aminocarbonyl]-1-methyl-benzimidazole by treating with [bis(trifluoroacetoxy)-iodo]benzene in acetonitrile/water at ambient temperature.

EXAMPLE 26

2-(4-Amidino-phenyl)-1-methyl-5-[[2-[[2-(2-oxo-1-pyrrolidinyl)-ethyl]-oxycarbonyl]-ethyl]-aminocarbonyl]-benzimidazole Prepared from 2-(4-amidino-phenyl)-1-methyl-5-[(2-carboxyethyl)-aminocarbonyl]-1-methyl-benzimidazole by heating to 60° C. for 36 hours in 1-(2-hydroxy-ethyl)-2-pyrrolidone and excess trimethylchlorosilane.

The following compounds are obtained analogously:
(1) 2-(4-amidino-phenyl)-1-methyl-5-[[2-[(2-phenyl-ethyl)-oxycarbonyl]-ethyl]-aminocarbonyl]-benzimidazole
(2) 2-(4-amidino-phenyl)-1-(4-phenyl-butyl)-5-[[2-[(3-pyridyl) methyloxycarbonyl]-ethyl]-aminocarbonyl]-benzimidazole

EXAMPLE 27

Dry ampoule containing 2.5 mg of active substance per 1 ml

Composition

| Active substance | 2.5 mg |
|---|---|
| Mannitol | 50.0 mg |
| Water for injections ad | 1.0 ml |

Preparation

The active substance and mannitol are dissolved in water. After transferring the solution to the ampoule, it is freeze-dried.

At the point of use, the solution is made up with water for injections.

EXAMPLE 28

Dry ampoule containing 35 mg of active substance per 2 ml

Composition

| Active substance | 35.0 mg |
|---|---|
| Mannitol | 100.0 mg |
| Water for injections ad | 2.0 ml |

Preparation

The active substance and mannitol are dissolved in water. After transferring the solution to the ampoule, it is freeze-dried.

At the point of use, the solution is made up with water for injections.

EXAMPLE 29

Tablet containing 50 mg of active substance

Composition

| (1) Active substance | 50.0 mg |
|---|---|
| (2) Lactose | 98.0 mg |
| (3) Corn starch | 50.0 mg |
| (4) Polyvinylpyrrolidone | 15.0 mg |
| (5) Magnesium stearate | 2.0 mg |
| | 215.0 mg |

Preparation (1), (2) and (3) are mixed together and granulated with an aqueous solution of (4). (5) is added to the dried granules. From this mixture, compressed tablets are produced, biplanar, facetted on both sides and notched on one side. Diameter of tablets: 9 mm.

EXAMPLE 30

Tablet containing 350 mg of active substance

Composition

| (1) Active substance | 350.0 mg |
|---|---|
| (2) Lactose | 136.0 mg |
| (3) Corn starch | 80.0 mg |
| (4) Polyvinylpyrrolidone | 30.0 mg |
| (5) Magnesium stearate | 4.0 mg |
| | 600.0 mg |

Preparation (1), (2) and (3) are mixed together and granulated with an aqueous solution of (4). (5) is added to the dried granules. From this mixture, compressed tablets are produced, biplanar, facetted on both sides and notched on one side. Diameter of tablets: 12 mm.

EXAMPLE 31

Capsules containing 50 mg of active substance

Composition

| (1) Active substance | 50.0 mg |
|---|---|
| (2) Dried corn starch | 58.0 mg |
| (3) Powdered lactose | 50.0 mg |
| (4) Magnesium stearate | 2.0 mg |
| | 160.0 mg |

Preparation (1) is triturated with (3). This triturate is added to the mixture of (2) and (4), with thorough mixing. This powdered mixture is packed into size 3 hard gelatin oblong capsules in a capsule filling machine.

EXAMPLE 32

Capsules containing 350.0 mg of active substance

Composition

| (1) Active substance | 350.0 mg |
|---|---|
| (2) Dried corn starch | 46.0 mg |
| (3) Powdered lactose | 30.0 mg |
| (4) Magnesium stearate | 4.0 mg |
| | 430.0 mg |

Preparation (1) is triturated with (3). This triturate is added to the mixture of (2) and (4), with thorough mixing.

This powdered mixture is packed into size 0 hard gelatin oblong capsules in a capsule filling machine.

We claim:

1. A condensed 5-membered heterocyclic compound of the formula

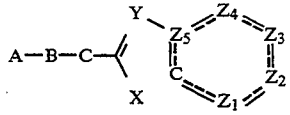

wherein (a) X represents an $NR_2$ group, and Y represents a nitrogen atom or an NO group; and
  (i) one of $Z_1$ to $Z_4$ represents a methine group substituted by a -D-E-F-G group, a second one of $Z_1$ to $Z_4$ represents a methine group substituted by $R_1$, the remaining two of $Z_1$ to $Z_4$ each represent a methine group, and $Z_5$ represents a carbon atom; or
  (ii) one of $Z_1$ to $Z_4$ represents a methine group substituted by a -D-E-F-G group, a second one of $Z_1$ to $Z_4$ represents a methine group substituted by $R_1$, a third one of $Z_1$ to $Z_4$ represents a methine group, a fourth one of $Z_1$ to $Z_4$ represents a nitrogen atom, and $Z_5$ represents a carbon atom; or (iii) one of $Z_1$ to $Z_4$ represents a methine group substituted by a -D-E-F-G group, a second one of $Z_1$ to $Z_4$ represents a methine group substituted by $R_1$, the remaining two of $Z_1$ to $Z_4$ each represent a nitrogen atom, and $Z_5$ represents a carbon atom, or (iv) one of $Z_1$ and $Z_3$ represents an imino group substituted by a -D-E-F-G group, the other one of $Z_1$ and $Z_3$ represents an imino group substituted by $R_1$, $Z_2$ and $Z_4$ each represent a carbonyl group, and $Z_5$ represents a carbon atom, or one of $Z_2$ and $Z_4$ represents an imino group substituted by a -D-E-F-G group, the other one of $Z_2$ and $Z_4$ represents an imino group substituted by $R_1$, $Z_1$ and $Z_3$ each represent a carbonyl group, and $Z_5$ represents a carbon atom;

(v) one of $Z_1$ and $Z_3$ represents an imino group substituted by a -D-E-F-G group, the other one of $Z_1$ and $Z_3$ represents a nitrogen atom, $Z_2$ represents a methine group substituted by $R_1$, $Z_4$ represents a carbonyl group, and $Z_5$ represents a carbon atom;

(b) X and $Z_5$ each represents a nitrogen atom, Y represents a methine group, one of $Z_1$ to $Z_4$ represents a methine group substituted by a -D-E-F-G group, a second one of $Z_1$ to $Z_4$ represents a methine group substituted by $R_1$, and the remaining two of $Z_1$ to $Z_4$ each represent a methine group;

R 1 represents a hydrogen, fluorine, chlorine or bromine atom, or an alkyl, aralkyl, aryl, heteroaryl, $R_3O-$, $(R_3)_2N-$, $R_4CO-NR_3-$, alkylsulphonyl$-NR_3-$, arylsulphonyl$-NR_3-$, $R_3S-$, $R_3SO-$, $R_3SO_2-$ or $R_5$ group, wherein $R_3$ represents a hydrogen atom, a $C_{1-6}$-alkyl group, an aryl, heteroaryl, aralkyl, carboxyalkyl or alkoxycarbonylalkyl group, $R_4$ represents a hydrogen atom, an alkyl or alkoxy group each having 1 to 6 carbon atoms, or an aryl, heteroaryl or aralkyl group having 1 to 6 carbon atoms in the alkyl moiety and $R_5$ represents an azetidino, pyrrolidino, hexamethyleneimino or heptamethyleneimino group or a piperidino group in which the methylene group in the 4-position may be replaced by an oxygen atom, by a sulphenyl, sulphinyl or sulphonyl group or by an imino group substituted by an $R_3$, $R_4CO-$, alkylsulphonyl or arylsulphonyl group, wherein $R_3$ and $R_4$ are as hereinbefore defined, $R_2$ represents a hydrogen atom, a straight-chained or branched $C_{1-15}$-alkyl group, a straight-chained or branched $C_{3-10}$-alkenyl or alkynyl group in which the double or triple bond cannot be directly joined to the nitrogen atom, a cycloalkyl or cycloalkylalkyl group each having 3 to 7 carbon atoms in the cycloalkyl moiety, an aryl or heteroaryl group, a $C_{2-6}$-alkyl group which is substituted from the $\beta$-position to the nitrogen atom of the $NR_2$ group by an $R_3O-$, $(R_3)_2N-$, $R_4CO-NR_3-$, alkylsulphonyl-$NR_3-$, arylsulphonyl-$NR_3-$, alkylsulphenyl, alkylsulphinyl, alkylsulphonyl or $R_5$ group, or a $C_{1-6}$-alkyl group which is substituted by one or two aryl groups, or by a heteroaryl, $R_6OCO-$, $(R_3)_2NCO-$, $R_5CO-$, $R_3O-CO$-alkylene-$NR_3-CO-$, $(R_3)_2N-CO$-alkylene-$NR_3-CO-$ or $R_5CO$-alkylene-$NR_3-CO-$group wherein $R_3$ and $R_5$ are as hereinbefore defined and $R_6$ represents a hydrogen atom, a $C_{1-6}$-alkyl group, a $C_{5-7}$-cycloalkyl group or an aralkyl group, A represents a cyano group, an amino group, a straight-chained or branched $C_{1-4}$-aminoalkyl group, an amidino, guanidino or guanidinoalkyl group, whilst in the above-mentioned amino, aminoalkyl, amidino, guanidino or guanidinoalkyl groups, at one of the nitrogen atoms one or two hydrogen atoms may be replaced by one or two $C_{1-4}$-alkyl groups or a hydrogen atom may be replaced by a $C_{2-5}$-(alkoxycarbonyl) group, by a $C_{4-6}$-(alkenyloxycarbonyl) group, by a $C_{2-5}$-(alkylcarbonyl) group, by an arylcarbonyl, aryloxycarbonyl, aralkoxycarbonyl, alkanoyloxymethoxy-carbonyl, cycloalkanoyloxymethoxycarbonyl, aralkanoyloxymethoxycarbonyl, aroyloxymethoxycarbonyl, phosphono, dialkylphosphoryl or O-alkyl-phosphono group in which the alkanoyl moieties may each contain 2 to 7 carbon atoms and the cycloalkanoyl moieties may each contain a total of 4 to 8 carbon atoms and the methoxy moiety may be substituted by a $C_{3-6}$-cycloalkyl group, by an aralkyl, aryl or alkyl group or by two alkyl groups, which may also form a 5- or 6-membered ring together with the methylene carbon atom, or, if B denotes a cyclic imine having 4 to 7 ring members, A may also denote a hydrogen atom or an alkyl group, each of which is bound to the imino nitrogen, B represents a phenylene group which may be mono- or disubstituted by fluorine, chlorine or bromine atoms, by alkyl, hydroxy, alkoxy, alkylsulphenyl, alkylsulphinyl, alkylsulphonyl, nitro, amino, alkylamino, dialkylamino, alkylcarbonylamino, alkylsulphonylamino or trifluoromethyl groups, wherein the substituents may be identical or different and at the same time one or two methine groups in the abovementioned phenylene groups may be replaced by one or two nitrogen atoms, or B represents a $C_{3-7}$-cycloalkylene group, whilst in a 4- or 5-membered cycloalkylene ring one ring member may denote a nitrogen atom and in a 6- or 7-membered cycloalkylene ring one or two ring members may each denote a nitrogen atom and at the same time linkage to carbon atoms of adjacent groups may be effected by means of such optionally present nitrogen atoms, or B is an indanylene or 1,2,3,4-tetrahydronaphthylene group wherein the saturated ring is bound to the group A and the aromatic ring is bound to the group C or to the condensed 5-membered heterocyclic group, C denotes a bond, an alkylene, arylene, $-O$-alkylene, $-S$-alkylene, $-NH$-alkylene, $-N(alkyl)$-alkylene, -alkylene-NH$-$, -alkylene$-N(alkyl)-$, $-SO$-alkylene or $-SO_2$-alkylene group, D denotes a bond or an alkylene group, E denotes a $C_{1-7}$-alkylene group, an alkenylene or alkynylene group each having 2 to 7 carbon atoms, whilst the double or triple bond may not be bound directly to a nitrogen atom of the -$Z_1$-$Z_2$-$Z_3$-$Z_4$- group, or, if E is not directly bound to a nitrogen atom of the -$Z_1$-$Z_2$-$Z_3$-$Z_4$- group, E may represent an $-O-$, $-S-$, $-SO-$, $-SO_2-$, $-NR_3-$, $-N(-$ $COR_4$)—, —CO—, —$NR_3$—CO—, —CO—$NR_3$—, —$SO_2$—$NR_3$—, alkylsulphonylimino or arylsulphonylimino group, wherein $R_3$ and $R_4$ are defined as hereinbefore, or a $C_{4-7}$-cycloalkylene group, whilst in a 4- or 5-membered cycloalkylene ring one ring member may denote a nitrogen atom and in a 6- or 7-membered cycloalkylene ring one or two ring members may each denote a nitrogen atom and additionally a methylene group adjacent to a nitrogen atom may be replaced by a carbonyl group, whilst at the same time linkage to carbon atoms of adjacent groups may be effected via any nitrogen atoms present, F denotes a bond, a straight-chained or branched $C_{1-6}$-alkylene group, a straight-chained or branched alkenylene or alkynylene group each having 2 to 6 carbon atoms, wherein the double or triple bond may not directly adjoin a heteroatom or a triple bond of group E, and the above-mentioned alkylene, alkenylene and alkynylene groups may each be substituted by an aryl, —$COOR_6$,—$CON(R_3)_2$ or —CO—$N(R_3)$-alkyl group, whilst the groups $R_3$ and $R_6$ are defined as hereinbefore and the alkyl moiety of the —CO—$N(R_3)$-alkyl group, which may contain 1 to 6 carbon atoms, may additionally be substituted by the groups $R_7$ and $R_8$, whilst $R_7$ and $R_8$, which may be identical or different, each represent a hydrogen atom, an aryl or a —$COOR_6$ group, wherein $R_6$ is defined as hereinbefore, or F is a cycloalkylene, alkylene-cycloalkylene or cycloalkylene-alkylene group each having 4 to 6 carbon atoms in the cycloalkylene moiety, wherein a CH group located in the ring is replaced by a nitrogen atom and the linking to the adjacent group E may be effected via the nitrogen atom, if the bond is effected via a carbon atom of group E, whilst if D denotes a bond, E denotes an oxygen atom and F is an alkyl group, A cannot be an amino or acylamino group directly bound to a phenyl ring, and if at the same time X is a sulfur atom and Y is a nitrogen atom, the group A-B-C cannot be a 4-acetamino-piperazino group, and G denotes a carbonyl group not bound to a heteroatom of group E, which may be substituted by a hydroxy group, by an arylalkenyloxy group having 3 to 4 carbon atoms in the alkenyl moiety, by a $C_{1-8}$-alkoxy group (wherein a $C_{1-5}$-alkoxy group may be substituted by an aryl group or an alkoxy group having 1 to 3 carbon atoms may be substituted in the 1-, 2- or 3-position by a heteroaryl or cycloalkyl group having 4 to 8 carbon atoms or, in the 2- or 3-position, by a pyrrolidin-2-on-1-yl, morpholino, thiomorpholino or 1-oxido-thiomorpholino group), by a $C_{4-8}$-cycloalkoxy group optionally substituted by 1 to 3 alkyl groups, by a benzocycloalkoxy, benzocycloalkyl-alkoxy, bicycloalkoxy or bicycloalkylalkoxy group, (having 4 to 8 carbon atoms in the cycloalkyl moiety and 6 to 8 carbon atoms in the bicycloalkyl moiety and optionally substituted by 1 to 3 methyl groups), by an alkanoyloxymethoxy group having a total of 2 to 7 carbon atoms in the alkanoyl moiety, by a cycloalkanoyloxy-methoxy group having a total of 4 to 8 carbon atoms in the cycloalkanoyl moiety, by an alkoxycarbonyloxymethoxy group having 1 to 6 carbon atoms in the alkyl moiety, by a cycloalkoxycarbonyloxymethoxy group having 3 to 7 carbon atoms in the cycloalkyl moiety, by an aroyloxymethoxy, aralkanoyloxymethoxy, aryloxycarbonyloxymethoxy or aralkoxycarbonyloxymethoxy group (wherein the methoxy moiety in each case may be substituted by a $C_{1-6}$-alkyl group, by a $C_{3-7}$-cycloalkyl group or by an aralkyl or aryl group), or G represents a sulpho-, phosphono-, O-alkylphosphono- or tetrazol-5-yl group, whilst unless otherwise specified the above-mentioned alkyl, alkylene or alkoxy moieties may each contain 1 to 3 carbon atoms, and the term "aryl group" denotes a phenyl group optionally mono-, di- or trisubstituted by fluorine, chlorine, bromine or iodine atoms or by alkyl, trifluoromethyl, nitro, amino, alkylamino, dialkylamino, alkanoylamino, alkylsulphonylamino, aminosulphonyl, alkylaminosulphonyl, dialkylaminosulphonyl, hydroxy, alkoxy, aralkoxy, carboxy, alkoxycarbonyl, aminocarbonyl, alkylaminocarbonyl, dialkylaminocarbonyl, alkylsulphenyl, alkylsulphinyl or alkylsulphonyl groups, wherein the substituents may be identical or different, or a naphthyl group, and the term "heteroaryl group" denotes a 5-membered heteroaromatic ring which contains an imino group, an oxygen or sulfur atom, one to two nitrogen atoms and an oxygen or sulfur atom, or an imino group and one to three nitrogen atoms, or a 6-membered heteroaromatic ring which contains 1, 2 or 3 nitrogen atoms, whilst fused on to the above-mentioned rings may be a phenyl ring and additionally the above-mentioned rings may be mono- or disubstituted by a fluorine, chlorine or bromine atom, by an alkyl, alkoxy, hydroxy, amino, dialkylamino, alkylcarbonylamino, alkylsulphonylamino or trifluoromethyl group or by a $C_{1-4}$-alkylamino group, or a tautomer or pharmaceutically acceptable salt thereof.

2. A compound in accordance with claim 1, wherein A, B, C, D, E, F, G, $R_1$ and $R_2$ are as defined in claim 1, and wherein:

(a) X represents a $NR_2$ group, and Y represents a nitrogen atom or an NO group; and (i) one of $Z_1$ to $Z_4$ represents a methine group substituted by a -D-E-F-G group, a second one of $Z_1$ to $Z_4$ represents a methine group substituted by $R_1$, the remaining two of $Z_1$ to $Z_4$ each represent a methine group, and $Z_5$ represents a carbon atom; or (ii) one of $Z_1$ to $Z_4$ represents a methine group substituted by a -D-E-F-G group, a second one of $Z_1$ to $Z_4$ represents a methine group substituted by $R_1$, a third one of $Z_1$ to $Z_4$ represents a methine group, a fourth one of $Z_1$ to $Z_4$ represents a nitrogen atom, and $Z_5$ represents a carbon atom; or (iv) one of $Z_1$ and $Z_3$ represents an imino group substituted by a -D-E-F-G group, the other one of $Z_1$ and $Z_3$ represents an imino group substituted by $R_1$, $Z_2$ and $Z_4$ each represent a carbonyl group, and $Z_5$ represents a carbon atom, or one of $Z_2$ and $Z_4$ represents an imino group substituted by a -D-E-F-G group, the other one of $Z_2$ and $Z_4$ represents an imino group substituted by $R_1$, $Z_1$ and $Z_3$ each represent a carbonyl group, and $Z_5$ represents a carbon atom;

(b) X and $Z_5$ each represents a nitrogen atom, Y represents a methine group, one of $Z_1$ to $Z_4$ represents a methine group substituted by a -D-E-F-G group, a second one of $Z_1$ to $Z_4$ represents a methine group substituted by $R_1$, and the remaining two of $Z_1$ to $Z_4$ each represent a methine group;

or a tautomer or pharmaceutically acceptable salt thereof.

3. A compound in accordance with claim 2, wherein:

$R_1$ is a hydrogen atom or a methyl, methoxy, methylamino, dimethylamino, N-butyloxycarbonyl-methylamino, N-isobutyloxycarbonyl-methylamino, N-carboxymethyl-amino, N-carboxymethyl-methylamino, N-methoxycarbonyl-methylamino or N-methoxycarbonylmethyl-methylamino group, $R_2$ is a hydrogen atom, a straight-chained or branched $C_{1-14}$-alkyl group, a $C_{1-3}$-alkyl group which is substituted by a carboxy or methoxycarbonyl group, a $C_{1-4}$-alkyl group which is substituted by a phenyl group optionally mono- or disubstituted by bromine atoms, amino or methoxy groups, or which is substituted by two phenyl groups or by a pyridyl group, a $C_{2-3}$-alkyl group substituted in the 2- or 3-position by an amino or piperidino group wherein the methylene group in the 4-position is replaced by an imino, benzylimino, sulphenyl, sulphinyl or sulphonyl group, A represents an aminomethyl or amidino group, wherein, at one of the nitrogen atoms, a hydrogen atom may be replaced by a methoxycarbonyl group, B represents a phenylene group, C represents a bond or an -O-methylene group, D represents a bond, E represents a $C_{3-4}$-alkylene group, or, if E is not directly bound to a nitrogen atom of the $Z_1$-$Z_2$-$Z_3$-$Z_4$ group, E may represent an —O—, —NH—CO— or —CO—NH-group, F represents a bond or a $C_{1-3}$-alkylene group and G represents a carboxy group, an alkoxycarbonyl group having a total of 2 to 5 carbon atoms or a cyclohexyloxy group, or a tautomer or pharmaceutically acceptable salt thereof.

4. 2-(4-Amidino-phenyl)-5-[(2-carboxy-ethyl)-aminocarbonyl]-1-methyl-benzimidazole or a pharmaceutically acceptable salt thereof.

5. 8-(4-Amidino-phenyl)-1-(4-carboxy-butyl)-3,9-dimethyl-xanthine or pharmaceutically acceptable salt thereof.

6. 2-(4-Amidino-phenyl)-6-[(2-carboxy-ethyl)-aminocarbonyl]-3-methyl-imidazo[4,5-c]pyridine or pharmaceutically acceptable salt thereof.

7. A method for treating or preventing diseases selected from the group consisting of venous and arterial thrombosis, cerebrovascular diseases, lung embolism, cardiac infarction or arteriosclerosis, in a warm blooded animal, which comprises administering to said animal a therapeutically effective amount of a compound in accordance with claim 1, 2, 3, 4, 5 or 6.

8. A compound selected from the group consisting of:

(a) 2-(4-amidino-phenyl)-5-[(2-carboxy-ethyl)-aminocarbonyl]-1-methyl-benzimidazole, (b) 2-(4-amidino-phenyl)-1-benzyl-5-[(2-carboxy-ethyl)-aminocarbonyl]-benzimidazole, (c) 2-(4-amidino-phenyl)-5-[(2-carboxy-ethyl)-aminocarbonyl]-1-(3-thiomorpholino-propyl)-benzimidazole, (d) 2-(4-amidino-phenyl)-5-[(2-carboxy-ethyl)-aminocarbonyl]-1-[3-(S-oxido-thiomorpholino)-propyl]-benzimidazole, (e) 2-(4-amidino-phenyl)-5-[(2-carboxy-ethyl)-aminocarbonyl]-1-[3-(S,S-dioxido-thiomorpholino)-propyl]-benzimidazole, (f) 2-(4-amidino-phenyl)-1-(3-amino-propyl)-5-[(2-carboxyethyl)-aminocarbonyl]-benzimidazole, (g) 2-(4-amidino-phenyl)-5-[(2-carboxy-ethyl)-aminocarbonyl]-1-methyl-benzimidazol-3-oxide, (h) 2-(4-amidino-phenyl)-1-[2-(4-benzyl-piperazino)-ethyl]-5-[(2-carboxy-ethyl)-aminocarbonyl]-benzimidazole, (i) 2-(4-amidino-phenyl)-5-[(2-carboxy-ethyl)-aminocarbonyl]-1-methyl-6-methylamino-benzimidazole, (j) 2-(4-amidino-phenyl)-5-[(2-carboxy-ethyl)-aminocarbonyl]-6-(N-carboxymethyl-methylamino)-1-methyl-benzimidazole, (k) 2-(4-amidino-phenyl)-5-[(2-carboxy-ethyl)-aminocarbonyl]-1-(2-piperazino-ethyl)-benzimidazole, (l) 2-(4-amidino-phenyl)-5-[(2-carboxy-ethyl)-aminocarbonyl]-1-[2-(3,4-dimethoxy-phenyl)-ethyl]-benzimidazole, (m) 2-(4-amidino-phenyl)-5-[(2-carboxy-ethyl)-aminocarbonyl]-1-(3-pyridylmethyl)-benzimidazole, (n) 2-(4-aminomethyl-phenyl)-5-[(2-carboxy-ethyl)-aminocarbonyl]-1-[2-(3,4-dimethoxy-phenyl)-ethyl]-benzimidazole, (o) 2-(4-amidino-phenyl)-5-[(2-carboxy-ethyl)-aminocarbonyl]-1-(4-phenyl-butyl)-benzimidazole, (p) 2-(4-amidino-phenyl)-1-[2-(4-amino-3,5-dibromo-phenyl)-ethyl]-5-[(2-carboxy-ethyl)-aminocarbonyl]-benzimidazole, (q) 2-(4-amidino-phenyl)-5-[(2-methoxycarbonyl-ethyl)-aminocarbonyl]-1-methyl-benzimidazole, (r) 2-(4-amidino-phenyl)-5-[(2-methoxycarbonyl-ethyl)-aminocarbonyl]-1-(3-thiomorpholino-propyl)-benzimidazole, (s) 2-(4-amidino-phenyl)-5-[(2-methoxycarbonyl-ethyl)-aminocarbonyl]-1-(4-phenyl-butyl)-benzimidazole, (t) 2-(4-amidino-phenyl)-1-[2-(4-amino-3,5-dibromo-phenyl)-ethyl]-5-[(2-methoxycarbonyl-ethyl)-aminocarbonyl]-benzimidazole, (u) 2-(4-amidino-phenyl)-1-[2-(3,4-dimethoxy-phenyl)-ethyl]-5-[(2-isopropyloxycarbonyl-ethyl)-aminocarbonyl]-benzimidazole, (v) 8-(4-amidino-phenyl)-1-(4-carboxy-butyl)-3,9-dimethyl-xanthine, (w) 2-(4-amidino-phenyl)-6-[(2-carboxy-ethyl)-aminocarbonyl]-3-methyl-imidazo[4,5]pyridine, and the tautomers and pharmaceutically acceptable salts thereof.

* * * * *